United States Patent [19]

Baschang et al.

[11] 4,423,038

[45] Dec. 27, 1983

[54] PHOSPHORYL COMPOUNDS, PHARMACEUTICAL PREPARATIONS CONTAINING SUCH COMPOUNDS, AND THEIR USE

[75] Inventors: Gerhard Baschang, Bettingen, Switzerland; Albert Hartmann, Grenzach, Fed. Rep. of Germany; Oskar Wacker, Basel, Switzerland; Lajos Tarcsay, Grenzach-Wyhlen, Fed. Rep. of Germany

[73] Assignee: Ciba-Geigy Corporation, Ardsley, N.Y.

[21] Appl. No.: 340,680

[22] Filed: Jan. 19, 1982

[30] Foreign Application Priority Data

Jan. 23, 1981 [CH] Switzerland .................... 439/81

[51] Int. Cl.³ .................... A61K 37/02; C07C 103/52
[52] U.S. Cl. ............................. 424/177; 260/112.5 R
[58] Field of Search ................. 424/177; 260/112.5 R

[56] References Cited

U.S. PATENT DOCUMENTS

| | | | |
|---|---|---|---|
| 4,082,735 | 4/1978 | Jones et al. | 260/112.5 R |
| 4,082,736 | 4/1978 | Jones et al. | 260/112.5 R |
| 4,101,536 | 7/1978 | Yamamura et al. | 260/112.5 R |
| 4,153,684 | 5/1979 | Audibert et al. | 260/112.5 R |
| 4,235,771 | 11/1980 | Adams et al. | 260/112.5 R |
| 4,256,735 | 3/1981 | Durette et al. | 260/112.5 R |
| 4,272,524 | 6/1981 | Chedid et al. | 260/112.5 R |
| 4,317,771 | 3/1982 | Shiba et al. | 260/112.5 R |
| 4,323,559 | 4/1982 | Audibert et al. | 260/112.5 R |
| 4,323,560 | 4/1982 | Baschang et al. | 260/112.5 R |

FOREIGN PATENT DOCUMENTS 6068  12/1979  European Pat. Off. .

OTHER PUBLICATIONS

P. Dulmor et al, Annual Reports in Medicinal Chemistry, 14, 146, 155, 156 and 165 (1979).
R. K. Jain, Tetrahedron Letters, 22, 2317–2320 (1981).
Chadid et al., Proc. Natl. Acad. Sci., USA, vol 74, 2089–2093 (1977).

Primary Examiner—Delbert R. Phillips
Assistant Examiner—F. T. Moezie
Attorney, Agent, or Firm—Irving N. Feit

[57] ABSTRACT

There are described hexopyranose compounds of the formula I and salts thereof having immunomodulatory action, which can be used, for example, in the form of pharmaceutical preparations, and also together with antibiotics, and processes for their manufacture.

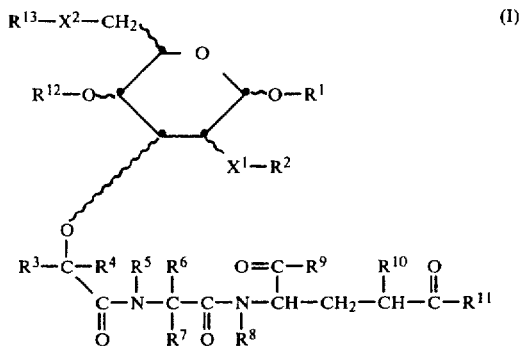

The variables are as described in the disclosure.

The invention relates to the above-mentioned compounds as immunomodulators, especially as immunostimulants, their use as pharmacologically active substances, especially their use as immunomodulators, particularly as immunostimulants, and their use for the manufacture of pharmaceutical preparations, and to pharmaceutical preparations containing these compounds.

24 Claims, No Drawings

PHOSPHORYL COMPOUNDS, PHARMACEUTICAL PREPARATIONS CONTAINING SUCH COMPOUNDS, AND THEIR USE

The present invention relates to phosphoryl compounds, especially hexopyranose compounds, of the formula I,

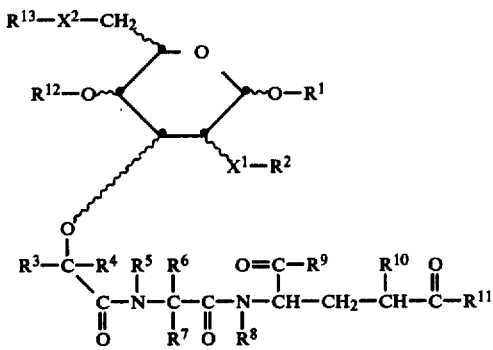
(I)

in which
each of
X$^1$ and X$^2$, independently of the other, represents a group of the formula —O— or —N(R$^{14}$)—, R$^{14}$ representing hydrogen or lower alkyl,
each of
R$^1$, R$^2$, R$^{12}$ and R$^{13}$, independently of one another, represents a radical of the formula Ia

(Ia)

in which n represents 0 or 1, Z$^1$ represents carbonyl or thiocarbonyl, Y$^1$ represents unsubstituted or substituted alkylene which may be interrupted by iminocarbonyl or oxycarbonyl, X$^3$ represents a group of the formula —O— or —N(R$^{14}$)—, wherein R$^{14}$ has the meaning given above, and A$^1$ represents a radical of the formula Ib,

(Ib)

in which R$^{15}$ represents an aliphatic or cycloaliphatic radical having at least 7 carbon atoms, or A$^1$ represents a group of the formula Ic,

(Ic)

in which R$^{16}$ represents hydrogen and R$^{17}$ represents 2-hydroxyethyl or 1,2-dihydroxyethyl, wherein at least one hydroxy group is esterified or etherified by a radical having at least 7 carbon atoms, or wherein each of R$^{16}$ and R$^{17}$, independently of the other, represents esterified or etherified hydroxymethyl, the esterifying or etherifying radicals having at least 7 carbon atoms, or
each of
R$^1$, R$^2$, R$^{12}$ and R$^{13}$, independently of one another, represents hydrogen, acyl other than a radical of the formula Ia in which n represents 1, or a radical that can be removed under physiological conditions,
each of
R$^3$, R$^4$, R$^5$, R$^7$ and R$^8$, independently of one another, represents hydrogen or lower alkyl,
R$^6$ represents hydrogen or lower alkyl that is unsubstituted or substituted by a group of the formula Id,

(Id)

in which m represents 0 or 1, E represents a group of the formula —O—, —S— or —N(R$^{14}$)—, R$^{14}$ having the meaning given above, Z$^2$ represents carbonyl or thiocarbonyl, Y$^2$ represents unsubstituted or substituted alkylene which may be interrupted by iminocarbonyl or oxycarbonyl, X$^4$ represents a group of the formula —O— or —N(R$^{14}$)—, R$^{14}$ having the meaning given above, and A$^2$ represents a radical of the formula Ib or Ic; or by free or etherified hydroxy or mercapto, by esterified hydroxy or mercapto other than a group of the formula Id, by free amino or substituted amino other than a group of the formula Id, by free, esterified or amidated carboxy, by cycloalkyl, by carbocyclic aryl or by nitrogen-containing heteroaryl having 5 or 6 ring members in the heterocyclic ring, or
R$^5$ and R$^6$ together represent unsubstituted or substituted 1,3- or 1,4-lower alkylene,
each of
R$^9$ and R$^{11}$, independently of the other, represents a radical of the formula Ie, $$-X^5-Y^3-X^6-A^3 \qquad (Ie)$$

in which X$^5$ represents a group of the formula —O—, —S— or —N(R$^{14}$)—, and X$^6$ represents a group of the formula —O— or —N(R$^{14}$)—, in each case R$^{14}$ having the meaning given above, Y$^3$ represents unsubstituted or substituted alkylene which may be interrupted by iminocarbonyl or oxycarbonyl, and A$^3$ represents a radical of the formula Ib or Ic, or free hydroxy or mercapto, etherified hydroxy or mercapto other than a radical of the formula Ie, or free amino, or substituted amino other than a radical of the formula Ie, and
R$^{10}$ represents hydrogen or free, esterified or amidated carboxy,
it being possible for free functional groups to be present in protected form, with the proviso that the compounds of the formula I have at least one radical A$^1$, A$^2$ or A$^3$, and with the further proviso that in compounds of the formula I in which at least one of the radicals R$^9$ and R$^{11}$ represents a group of the formula Ie, the pyranose ring is other than a D-glucopyranose ring, or R$^1$ is other than hydrogen, or X$^1$ is other than the radical of the formula —N(R$^{14}$)— and R$^2$ is other than acyl, or R$^{12}$ is other than hydrogen, or the radical of the formula —X$^2$— R$^{13}$ is other than hydroxy, or R$^4$ is other than hydrogen, or R$^6$ is other than hydrogen or than lower alkyl that is unsubstituted or substituted by free or etherified hydroxy or mercapto, by esterified hydroxy or mercapto other than a group of the formula Id, or by free amino or substituted amino other than a group of the formula Id, by cycloalkyl, by carbocyclic aryl or by nitrogen-containing heteroaryl having 5 or 6 ring members in the heterocyclic ring, or $R^7$ is other than hydrogen, and salts of such compounds.

The invention relates also to the above-mentioned compounds as immunomodulators, especially as immunostimulants, their use as pharmacologically active substances, especially their use as immunomodulators, particularly as immunostimulants, and their use for the manufacture of pharmaceutical preparations, and to pharmaceutical preparations containing these compounds.

Acyl, for example as $R^1$, $R^2$, $R^{12}$ and $R^{13}$, is especially the acyl radical of an organic carboxylic acid, especially an aliphatic, but also a cycloaliphatic, cycloaliphatic-aliphatic, aromatic or araliphatic carboxylic acid, which may have, for example, up to 90 carbon atoms.

Aliphatic carboxylic acids are, inter alia, alkanecarboxylic acids that are unsubstituted or substituted, for example, by hydroxy or etherified or esterified hydroxy, such as lower alkoxy or lower alkanoyloxy, by unsubstituted or substituted amino, such as lower alkylamino, di-lower alkylamino, or by acylamino, for example alkanoylamino, and corresponding alkene- or alkyne-carboxylic acids that may have one or more double or triple bonds. These acids may contain, for example, up to 90 carbon atoms, $R^2$ as the radical of an aliphatic carboxylic acid, in the case when $X^1$ represents a group of the formula $-N(R^{14})-$, preferably representing the acyl radical of an unsubstituted or hydroxy-substituted lower alkanecarboxylic acid.

Cycloaliphatic carboxylic acids may be monocyclic or polycyclic and as a cycloaliphatic radical contain monocyclic or polycyclic cycloalkyl that is unsubstituted or is substituted, for example by hydroxy, and corresponding cycloalkenyl.

In cycloaliphatic-aliphatic radicals, the cycloaliphatic moiety and the aliphatic moiety have the meanings given above; such radicals are especially monocyclic or polycyclic cycloalkyl-lower alkyl.

Aromatic and araliphatic carboxylic acids are, inter alia, benzoic or phenyl-lower alkanecarboxylic acids that are unsubstituted or substituted, for example by lower alkyl, hydroxy, lower alkoxy or halogen.

Groups that can be removed under physiological conditions are especially organic silyl groups, especially aliphatically substituted silyl groups, such as tri-lower alkylsilyl.

Substituents of alkylene, which is represented by the radicals $Y^1$, $Y^2$ and $Y^3$, are, inter alia, hydroxy, esterified or etherified hydroxy, such as acyloxy, for example lower alkanoyloxy, or lower alkoxy, amino or substituted amino, such as lower alkylamino, di-lower alkylamino or acylamino, for example lower alkanoylamino. In an alkylene radical that is interrupted by iminocarbonyl or oxycarbonyl, there may be one or more, for example two, such groups and these may be present as groups of the formula $-N(R^{14})-C(=O)-$ or $-O-C(=O)-$, and as groups of the formula $-C(=O)-N(R^{14})-$ or $-C(=O)-O-$, and $R^{14}$ has the meaning given above and preferably represents hydrogen. An alkylene radical formed by the groups $R^5$ and $R^6$ and having 3 or 4 carbon atoms in the chain may be substituted, for example by hydroxy, which may be acylated, for example by a group of the formula Ia.

An aliphatic radical having at least 7 carbon atoms that is the group $R^{15}$ or etherifies a hydroxy group in a radical $R^{16}$ or $R^{17}$ is especially a corresponding unsubstituted or substituted alkyl radical but may also represent a corresponding unsaturated radical, such as an unsubstituted or substituted alkenyl radical having one or more double bonds, such radicals having, for example, from 7 up to and including 90 carbon atoms, preferably from 7 up to and including 30 carbon atoms. Substituents of such aliphatic radicals are, for example, hydroxy, etherified or esterified hydroxy, such as lower alkoxy or lower alkanoyloxy and/or unsubstituted or substituted amino, such as lower alkylamino, di-lower alkylamino or alkanoylamino.

A corresponding cycloaliphatic radical that is the group $R^{15}$ or a radical etherifying a hydroxy group in a radical $R^{16}$ or $R^{17}$ is especially monocyclic or polycyclic cycloalkyl, also corresponding cycloalkenyl, which may contain one or more double bonds. Such radicals contain at least 7, and preferably from 7 to 30, carbon atoms, and may, in addition, be substituted, for example by hydroxy, etherified or esterified hydroxy, such as lower alkoxy or lower alkanoyloxy, or by unsubstituted or substituted amino, such as lower alkylamino, di-lower alkylamino or alkanoylamino.

Etherified hydroxy or substituted amino as a radical $R^9$ or $R^{11}$ is, for example, lower alkoxy, or, for example, lower alkylamino, in which lower alkyl may be substituted.

A radical esterifying a hydroxy group in a radical $R^{16}$ or $R^{17}$ is especially an acyl radical of an organic carboxylic acid, especially of the above-mentioned aliphatic and cycloaliphatic, cycloaliphatic-aliphatic, aromatic or araliphatic carboxylic acids, preferably having from 7 to 90 carbon atoms.

Etherified hydroxy or mercapto or esterified hydroxy or mercapto other than a radical of the formula Id as substituent of lower alkyl $R^6$ is, for example, lower alkoxy, acyloxy, such as alkanoyloxy, wherein alkanoyl contains up to 90, for example from 7 to 30, carbon atoms and may optionally be substituted, for example by hydroxy, or is halogen, lower alkylthio or acylthio, such as alkanoylthio, wherein alkanoyl contains up to 90, for example from 7 to 30, carbon atoms. Substituted amino other than a radical of the formula Id as substituent of a lower alkyl group $R^6$ is, for example, lower alkylamino, guanylamino or acylamino, such as alkanoylamino, wherein alkanoyl may contain up to 90, for example up to 30, carbon atoms. Esterified carboxy as substituent of a lower alkyl radical $R^6$ is preferably carboxy esterified by an aliphatic radical, such as alkyl having up to 30 carbon atoms, that is to say, for example, corresponding alkoxycarbonyl, whilst corresponding amidated carboxy, is, for example, aminocarbonyl or lower alkylaminocarbonyl, wherein lower alkyl may be substituted, for example by carboxy, alkoxycarbonyl or aminocarbonyl. Esterified or amidated carboxy in a radical $R^6$ may also be a radical of the formula

(Ida)

in which m, E, $Y^2$, $X^4$ and $A^2$ have the meanings given above.

Aryl as substituent of a lower alkyl group $R^6$ is especially phenyl that is unsubstituted or substituted, for example by lower alkyl, hydroxy or etherified or esterified hydroxy, such as lower alkoxy, or halogen, whilst nitrogen-containing heteroaryl having 5 or 6 ring members in the heterocyclic ring as corresponding substituent of $R^6$ is monocyclic or bicyclic heteroaryl containing one or two nitrogen atoms as ring members.

Etherified mercapto as radical $R^9$ or $R^{11}$ is especially lower alkylthio, whilst in a lower alkylamino radical $R^9$ or $R^{11}$ the lower alkyl group may be substituted, for example by carboxy, lower alkoxycarbonyl or aminocarbonyl.

Esterified carboxy $R^{10}$ is especially lower alkoxycarbonyl, whilst amidated carboxyl $R^{10}$ may be carbamoyl or N-lower alkylcarbamoyl, wherein lower alkyl may be substituted, for example by carboxy, lower alkoxycarbonyl or aminocarbonyl.

In compounds of the formula I having free functional groups, such as hydroxy, mercapto, amino and carboxyl, such groups may be present in protected form. In this case, hydroxy and mercapto are preferably protected in acylated or etherified form, whilst amino is preferably protected in acylated form and carboxy in esterified form.

In the context of the present description, the general terms used above have the following meanings, radicals and compounds that are termed "lower" containing up to and including 7, preferably up to and including 4, carbon atoms:

Alkyl is, for example, lower alkyl, such as methyl, ethyl, n-propyl, isopropyl, n-butyl, tributyl, sec.-butyl or tert.-butyl, also n-pentyl, neopentyl, n-hexyl or n-heptyl, or higher alkyl, such as straight-chain or branched octyl, nonyl, decyl, undecyl, dodecyl, tridecyl, tetradecyl, pentadecyl, hexadecyl, heptadecyl, nonadecyl or heneicosyl, and also higher alkyl of the triacontyl, tetracontyl, pentacontyl, hexacontyl, heptaconyl, octacontyl or nonacontyl series.

Lower alkoxy is, for example, methoxy, ethoxy, n-propoxy, isopropoxy, n-butoxy, isobutoxy or tert.-butoxy.

Alkanoyloxy is lower or higher alkanoyloxy, lower alkanoyloxy being, for example, formyloxy, acetoxy, propionyloxy or butyryloxy, whilst higher alkanoyloxy is, for example, lauroyloxy, myristinoyloxy, palmitoyloxy, stearoyloxy or behenoyloxy. Alkanoyloxy substituted by hydroxy, for example higher alkanoyloxy, is, inter alia, mycoloyloxy.

Lower alkylamino is, for example, methylamino, ethylamino, n-propylamino or isopropylamino. Di-lower alkylamino is, for example, dimethylamino, diethylamino or di-isopropylamino. Alkanoylamino is lower alkanoylamino, for example formylamino, acetylamino or propionylamino, or higher alkanoylamino, for example lauroylamino, palmitoylamino, stearoylamino or behenoylamino.

An alkanecarboxylic acid is, for example, a lower alkanecarboxylic acid, such as acetic acid, propionic acid, butyric acid or caproic acid, or a higher alkanecarboxylic acid, such as lauric acid, myristic acid, palmitic acid, stearic acid or behenic acid, whilst, for example, an alkanoic acid substituted by hydroxy may be, inter alia, mycolic acid.

Alkene- and alkyne-carboxylic acids are, inter alia, lower alkene- and lower alkyne-carboxylic acids, such as acrylic acid, crotonic acid or tetrolic acid, or higher alkene- and higher alkyne-carboxylic acids, such as undecylenic acid, oleic acid or elaidic acid. The acyl radical of a lower alkanecarboxylic acid, which is the group $R^2$ in the case when $X^1$ represents the radical of the formula $-N(R^{14})-$, is especially acetyl or hydroxyacetyl, and propionyl.

Cycloalkyl is, for example, cyclopentyl, cyclohexyl or adamantyl, whilst cycloalkenyl may be, for example, 1-cyclohexenyl, and cycloalkyl-lower alkyl may be, for example, 3-cholanylmethyl or the acyl radical of cholanic acid.

Phenyl-lower alkanecarboxylic acids are, for example, phenylacetic acid or phenylpropionic acid, which may be substituted, for example as stated.

Halogen is preferably halogen having an atomic number of up to 35 and represents especially chlorine, also fluorine or bromine.

Tri-lower alkylsilyl is especially trimethylsilyl.

Alkylene is straight-chain or branched and is especially lower alkylene, for example methylene, ethylene, 1,2-propylene, 1,3-propylene or 1,6-hexylene, also higher alkylene, such as 1,11-undecylene.

Alkenyl is lower alkenyl, for example allyl or methallyl, or higher alkenyl, for example decenyl.

Lower alkylthio is, for example, methylthio or ethylthio.

In an alkanoylthio radical, the alkanoyl radical represents lower alkanoyl, for example acetyl, propionyl, butyryl or hexanoyl, but may also represent higher alkanoyl, for example lauroyl, myristinoyl, palmitoyl, stearoyl or behenoyl.

Alkoxycarbonyl is lower alkoxycarbonyl, for example methoxycarbonyl, ethoxycarbonyl or tert.-butoxycarbonyl, or higher alkoxycarbonyl, for example dodecyloxycarbonyl, tetradecyloxycarbonyl, hexadecyloxycarbonyl or heneicosyloxycarbonyl.

Lower alkylaminocarbonyl is, for example, methylaminocarbonyl or ethylaminocarbonyl, also carboxy-, lower alkoxycarbonyl- or carbamoyl-lower alkylaminocarbonyl, such as carboxymethylaminocarbonyl, 1-carboxyethylaminocarbonyl, methoxycarbonylmethylaminocarbonyl or carbamoylmethylaminocarbonyl.

Nitrogen-containing heteroaryl having 5 or 6 ring members in the heterocyclic ring is, for example, imidazolyl, such as 4-imidazolyl, or indolyl, such as 3-indolyl.

In the compounds of the formula I having free functional groups, such as carboxyl, amino, hydroxy or mercapto, such groups may, as described above, be in protected form, there being used as protecting groups the protecting groups customarily used in peptide, penicillin, cephalosporin and sugar chemistry.

Such protecting groups can be removed readily, that is to say, without undesired side-reactions taking place, for example by solvolysis, reduction or photolysis.

Protecting groups of this type and the manner in which they are removed are described, for example, in "Protective Groups in Organic Chemistry", (Plenum Press, London, New York, 1973), in Schröder and Lübke, "The Peptides", vol. I, (Academic Press, London, New York 1965), and in Houben-Weyl, "Methoden der organischen Chemie", vol. 15/1, (4th edition, Georg Thieme Verlag, Stuttgart 1974).

Thus carboxyl groups are usually protected in esterified form and contain as esterifying groups especially lower alkyl groups branched in the 1-position or suitably substituted in the 1- or 2-position. Preferred carboxyl groups protected in esterified form are, inter alia, tert.-lower alkoxycarbonyl, for example tert.-butoxycarbonyl; arylmethoxycarbonyl having one or two aryl radicals, these being phenyl radicals optionally substituted, for example, by lower alkyl, lower alkoxy, hydroxy, halogen and/or nitro: such as benzyloxycarbonyl that is unsubstituted or substituted, for example as indicated above, for example benzyloxycarbonyl, 4-nitrobenzyloxycarbonyl or 4-methoxybenzyloxycarbonyl, or diphenylmethoxycarbonyl that is unsubstituted or substituted, for example as indicated above, for example diphenylmethoxycarbonyl or di-(4methoxyphenyl)-methoxycarbonyl; aroylmethoxycarbonyl, for example phenacyloxycarbonyl, in which the aroyl group is benzoyl that is unsubstituted or substituted, for example by halogen; 2-halo-lower alkoxycarbonyl, for example 2,2,2-trichloroethoxycarbonyl, 2-bromoethoxycarbonyl or 2-iodoethoxycarbonyl; or 2-(tri-substituted silyl)-ethoxycarbonyl, in which each of the substituents represents, independently of one another, an aliphatic, araliphatic, cycloaliphatic or aromatic hydrocarbon radical having, for example, up to 15 carbon atoms and being unsubstituted or substituted, for example by lower alkyl, phenyl, lower alkoxy, halogen and/or nitro, such as corresponding unsubstituted or substituted lower alkyl, phenyl-lower alkyl, cycloalkyl or phenyl: for example 2-tri-lower alkylsilylethoxycarbonyl, such as 2-trimethylsilylethoxycarbonyl or 2-(di-n-butyl-methyl-silyl)-ethoxycarbonyl, or 2-triarylsilylethoxycarbonyl, such as 2-triphenylsilylethoxycarbonyl.

Further protected carboxyl groups in esterified form are corresponding silyloxycarbonyl groups, especially organic silyloxycarbonyl groups. In these, the silicon atom contains as substituent preferably lower alkyl, especially methyl, also lower alkoxy, for example methoxy, and/or halogen, for example chlorine. Suitable silyl protecting groups are especially tri-lower alkylsilyl, especially trimethylsilyl and dimethyl-tert.butylsilyl.

Preferred carboxyl groups in protected form are tert.-lower alkoxycarbonyl, such as tert.-butoxycarbonyl, and especially benzyloxycarbonyl or diphenylmethoxycarbonyl that is unsubstituted or substituted, for example as mentioned above.

A protected amino group may be, for example, in the form of a readily cleavable acylamino group, or in the form of an arylmethylamino or azido group.

In a corresponding acylamino group, acyl is, for example, the acyl radical of an organic carboxylic acid having, for example, up to 18 carbon atoms, especially of an alkanecarboxylic acid that is preferbly substituted, for example by halogen or aryl, or of a carbonic acid semiester. Such acyl groups are, for example, lower alkanoyl, such as formyl or acetyl; halo-lower alkanoyl, such as 2-haloacetyl, especially 2-chloro-, 2-bromo-, 2-iodo-, 2,2,2-trifluoro- or 2,2,2-trichloro-acetyl; or lower alkoxycarbonyl branched in the 1-position of the lower alkyl radical or suitably substituted in the 1- or 2-position, especially tert.-lower alkoxycarbonyl, for example tert.-butoxycarbonyl; arylmethoxycarbonyl having one or two aryl radicals that are unsubstituted or are phenyl that is substituted, for example, by lower alkyl, especially tert.-lower alkyl, lower alkoxy, hydroxy, halogen and/or nitro: such as unsubstituted or substituted benzyloxycarbonyl, for example benzyloxycarbonyl or 4-nitrobenzyloxycarbonyl, or diphenylmethoxycarbonyl, for example benzhydroxycarbonyl or di-(4-methoxyphenyl)-methoxycarbonyl; aroylmethoxycarbonyl, for example phenacyloxycarbonyl, in which the aroyl group is benzoyl that is unsubstituted or substituted, for example, by halogen; 2-halo-lower alkoxycarbonyl, for example 2,2,2-trichloroethoxycarbonyl, 2-bromoethoxycarbonyl or 2-iodoethoxycarbonyl; or 2-(trisubstituted silyl)-ethoxycarbonyl, such as, for example, 2-tri-lower alkylsilylethoxycarbonyl, such as 2-trimethylsilylethoxycarbonyl, or 2-(di-n-butylmethylsilyl)-ethoxycarbonyl, or 2-triarylsilylethoxycarbonyl, such as 2-triphenylsilylethoxycarbonyl.

An arylmethylamino group is a mono-, di- or, especially, a tri-arylmethylamino group in which the aryl radicals are especially unsubtituted or substituted phenyl radicals. Such groups are, for example, benzylamino, diphenylmethylamino and especially tritylamino.

Amino groups may also contain organic silyl groups as protecting groups. Suitable silyl protecting groups are especially tri-lower alkylsilyl, especially trimethylsilyl and dimethyl-tert.-butyl-silyl.

Preferred amino-protecting groups are acyl radicals of carbonic acid semiesters, especially tert.-butoxycarbonyl, benzyloxycarbonyl that is unsubstituted or substituted, for example as indicated, for example benzyloxycarbonyl or 4-nitrobenzyloxycarbonyl, or diphenylmethoxycarbonyl, or 2-halo-lower alkoxycarbonyl, such as 2,2,2-trichloroethoxycarbonyl, also trityl or formyl.

Hydroxy- and mercapto-protecting groups are, for example, acyl radicals, such as lower alkanoyl that is unsubstituted or substituted, for example by halogen, such as 2,2-dichloroacetyl, or especially the acyl radicals of carbonic acid semiesters mentioned in connection with the amino-protecting groups, especially 2,2,2-trichloroethoxycarbonyl, and also etherifying groups that can readily be removed, such as tert.-lower alkyl, for example tert.-butyl, 2-oxa- or 2-thia-aliphatic or 2-oxa- or 2-thia-cycloaliphatic hydrocarbon radicals, especially 1-lower alkoxy-lower alkyl or 1-lower alkylthio-lower alkyl, for example methoxymethyl, 1-methoxyethyl, 1-ethoxyethyl, 1-methylthiomethyl, 1-methylthioethyl or 1-ethylthioethyl, or 2-oxa- or 2-thiacycloalkyl having from 5 to 7 ring atoms, for example 2-tetrahydrofuryl or 2-tetrahydropyranyl, or corresponding thia analogues, and unsubstituted or substituted 1-phenyl-lower alkyl, such as unsubstituted or substituted benzyl, diphenylmethyl or trityl, there coming into consideration as substituents of the phenyl radicals, for example, halogen, lower alkoxy and/or nitro.

Hydroxy and mercapto groups may also be protected in the form of corresponding organic silyloxy or silylthio groups. Suitable silyl protecting groups are especially tri-lower alkylsilyl, especially trimethylsilyl, or dimethyl-tert.-butyl-silyl.

In this case, two free functional groups may also be protected by a common protecting group that can readily be removed. Thus, for example, hydroxy groups represented by the radicals $R^{12}$—O— and $R^{13}$—$X^2$— may be protected by a methylene radical that is unsubstituted or, preferably, substituted, for example by lower alkyl, such as methyl, or aryl, such as phenyl: such as methylene, isopropylidene, propylidene or benzylidene.

The hexopyranose compounds of the formula I may be in the form of isomeric mixtures or pure isomers.

They may thus have the L- or DL-configuration in the sugar moiety, but have preferably the D-configuration. Furthermore, the hexopyranose moiety may be that of any hexose, but is preferably that of an allose, galactose or mannose, but especially of a glucose. That is to say, the compounds of the present invention are especially corresponding allo-, galacto- or mannopyranose compounds, but especially corresponding glucopyranose compounds having preferably the D-configuration.

The radical of the formula —C(R³)(R⁴)—C(=O)— linked to the oxygen atom, in the case when one of the groups R³ and R⁴ is other than hydrogen, is preferably in optically active form and has especially the D-configuration, whilst the radical of the amino acid of the formula —N(R⁵)—C(R⁶)(R⁷)—C(=O)—, in the case when one of the radicals R⁶ and R⁷ is other than hydrogen, is likewise preferably in optically active form, especially in the L-configuration, and the terminal α-aminoglutaric acid radical is preferably in optically active form, especially in the D-configuration. Furthermore, the optionally substituted 1-hydroxy group of the formula —O—R¹ may have the α- or the β-configuration; the novel compounds of the formula I may, however, also be in the form of a mixture of the 1-α- and 1-β-isomers.

In the compounds of the formula I, the proton bonded to phosphorus via an oxygen atom can readily be replaced by a cation, that is to say, the compounds form salts. The compounds of the formula I may be in the form of a mixture of the free compounds and their salts; the invention relates also to the latter. The invention relates especially to pharmaceutically acceptable, non-toxic salts of compounds of the formula I. These are especially metal or ammonium salts, such as alkali metal and alkaline earth metal salts, for example sodium, potassium, magnesium or calcium salts, and ammonium salts, or salts with suitable organic amines, such as lower alkylamines, for example triethylamine. Compounds of the formula I having basic groups, for example amino groups, are in the form of internal salts but, when there are more basic than acidic groups in a molecule of the formula I, they may also form acid addition salts with external acids, such as salts with inorganic acids, such as mineral acids, for example hydrochloric, sulphuric or phosphoric acid, or organic carboxylic or sulphonic acids, for example acetic, maleic, fumaric, tartaric, citric, methanesulphonic or 4-toluenesulphonic acid. For isolation or purification it is also possible to use pharmaceutically unacceptable salts. Only the pharmaceutically acceptable, non-toxic salts are used therapeutically, however, and these are therefore preferred.

The novel compounds of the present invention have a number of valuable pharmacological properties, especially a pronounced immunomodulating, for example immunopotentiating, action.

Thus in vivo, these compounds considerably increase the ability of mice to form antibodies, which can be demonstrated by the following experimental procedure:

NMRI mice are immunised by intraperitoneal injection of 10 μg of precipitate-free bovine-serum-albumin (BSA) on day 0. 9, 15 and 29 days later, serum samples are taken and examined for their content of anti-BSA antibodies using a passive haemagglutination technique. In the dose used, soluble BSA is subimmunogenic for the recipient animals, that is to say, it is unable to initiate any, or is able to initiate only a very insignificant, production of antibodies. Additional treatment of the mice with immunopotentiating substances before or after the administration of antigen results in an increase in the antibody titre in the serum. The effect of the treatment is expressed by the score value achieved, that is to say, by the sum of $\log_2$ titre differences on the three days on which blood samples were taken.

In this test, on intraperitoneal or subcutaneous administration of from 0.5 to 5 mg/kg on five successive days after immunisation with BSA, the compounds of the formula I are able significantly to increase the antibody production against BSA.

Manifestations of the cell-imparted immunity can also be potentiated in vivo by the mentioned compounds as can be demonstrated by the following experiment:

Whereas sensitisation of guinea pigs with BSA in incomplete Freund's adjuvant results only in humoral antibody formation, the admixture of the phosphorylmuramyl peptides according to the invention in a dose range of from 5 to 50 μg to the antigen-oil emulsion induces delayed hypersensitivity to BSA; three weeks after immunisation, intracutaneous injection of BSA in these animals results in a local inflammatory reaction with erythemia and thickening of the skin, which reaches its maximum within 24 to 48 hours. These delayed reactions correspond quantitatively and qualitatively to those normally obtained by immunisation with BSA in complete Freund's adjuvant (that is, with the addition of mycobacteria). The $ED_{50}$ values (μg/animal) required for the induction of a difference in the reaction volume of 200 μl, [erythemia area×increase in skin thickness] in treated and untreated animals 24 hours after induction) are from approximately 10 to approximately 20 μg for the compounds according to the present invention.

Special emphasis should be given also to the ability of the compounds of the present invention, by administration together with BSA in liposomes (egg lecithin: cholesterol 4:1; 4 mg/animal) and without the toxic mineral oil component, to induce in guinea pigs a delayed hypersensitivity to BSA. Quantitatively and qualitatively these delayed reactions are likewise identical to those obtained by immunisation with BSA in complete Freund's adjuvant. The $ED_{50}$ values are 100 to 300 μg per animal.

The novel compounds of the present invention are effective also in the following experimental procedure:

Balb/c mice are immunised by intraperitoneal injection of $2 \times 10^4$ P815 mastocytoma cells on day 0. On day 15 the splenocytes of the animals immunised in this manner are examined in vitro for the presence of cytotoxic T-lymphocytes directed against P815 mastocytoma cells. For this purpose, the P815 target cells are labelled with $^{51}Cr$ and the extent of the cytotoxic reaction is ascertained by measuring the radioactivity in the culture supernatant. In the dose used, the P815 mastocytoma cells are sub-immunogenic for the recipient mice, that is to say, they induce no, or only a very insignificant, formation of cytotoxic T-cells. Simultaneous intraperitoneal administration of from 1 to 50 μg of the compounds of the present invention results in a significant increase in the formation of cytotoxic T-cells (by a factor of 10 to 30 compared with untreated mice).

The immunopotentiating properties of the novel compounds of the present invention can also be demonstrated in mice in the case of the induction of specific immunotolerance to transplant antigens by immunisation with autoblasts to which an adjuvant has been added:

In a mixed lymphocyte culture, splenolymphocytes of the prospective transplant recipient (C57 B1/6J mice) are incubated with irradiated splenocytes of the prospective transplant donor (CBA/J mice). T-lymphocytes having specific receptors for the histocompatibility antigens of the donor proliferate and become blast cells; these can be separated from the other cells by sedimentation. The specific blast cells express the relevant idiotypic specificities of the membrane receptors and, admixed with complete Freund's adjuvant (CFA), are injected into the prospective transplant recipients (C57 B1/6J) as autoimmunogens for the induction of specific tolerance to the relevant transplant antigens. The immunisation is carried out four times at intervals of four weeks with autologous anti-CBA/J T-lymphoblasts. Adsorbates of T-autoblasts with the novel compounds of the formula (I) ($10^9$ blast cells are suspended in a solution of 20 mg of substance in 20 ml of PBS; after a two-hour incubation period the cells are centrifuged and washed twice with PBS) are able to induce specific immunotolerance in the absence of CFA, the adsorbates being as effective as the lymphoblasts in CFA.

The compounds of the present invention are also able, in concentrations of from approximately 0.5 to approximately 100 µg/ml in splenocyte cultures of normal mice, to induce the formation of antibody-producing cells (an increase in the 19S-plaque-forming cells by a factor of 10 to 30 above the control value [in the absence of the stimulating substance]). Thus in the presence of the novel compounds, for example specific antibodies against sheep erythrocytes are formed, without sheep erythrocytes being added to the cultures for the immunisation. On the other hand, when compared with a normally thymus-dependent antigen (sheep erythrocytes), the mentioned substances, in the same concentration range, are also able to increase the immunological reactivity of T-cell-depleted splenocyte cultures (of congenitally athymic nu/nu mice) (by a factor of 10 to 30 compared with untreated control cultures). The mentioned compounds, however, in vitro directly or indirectly induce not only proliferation and synthesis of B-lymphocytes (i.e. of potential antibody-forming cells), but also impart effects to T-lymphocytes (to which regulatorily active promoter and suppressor cells and also cytotoxic effector cells belong). Thus, for example, the novel compounds in a concentration range of from approximately 1 to approximately 20 µg/ml are able to potentiate considerably (up to 10 times) the reactivity of cortisone-resistant thymus cells compared with allogenic irradiated stimulator lymphocytes.

The above-mentioned effects are probably indirectly brought about as a result of the fact that the compounds of the present invention activate macrophages, which in turn promote the reactivity of T- and B-lymphocytes. In fact, it can be shown that the mentioned compounds, even in small concentrations (0.5 to 10 µg/ml), liberate large amounts of "colony stimulating activity" (CSA) from mouse-macrophages (induction of up to 150 to 200 colonies within 7 days from $10^5$ bone marrow cells of mice after the addition of 20% supernatant liquor from macrophage cultures incubated for 24 hours with the substance, compared with 0 to 5 colonies on the addition of supernatant liquors of untreated macrophage cultures). CSA is a biological mediator which is necessary for the differentiation of bone marrow parent cells to macrophages and polymorphonuclear leucocytes. The novel compounds in this way cause an increased supply of cells that are of prime importance for non-specific resistance and for the induction, amplification and expression of specific (lymphocyte-induced) immuno-reactions.

The immunopotentiating action of the novel compounds can also be demonstrated in vivo: the injection of a compound of the present invention results within 3 to 9 hours in a great increase in the CSA concentration in the serum (up to 120 colonies per $10^5$ bone marrow cells of mice after the addition of serum extracted with chloroform [5% final concentration] compared with 0 to 5 colonies in untreated animals). Correspondingly, by administration of the same compounds in vivo the ability of mice to form antibodies is considerably potentiated.

The immunopotentiating properties of the novel compounds of the present invention can also be demonstrated in tumour models, for example the Ehrlich ascites tumour in mice.

An intraperitoneal injection of $10^6$ syngenic Ehrlich ascites tumour cells in Balb/c mice leads on average in 18 days to the death of the animals. If the mice are injected intraperitoneally with $10^7$ (group 1), $10^6$ (group 2) and $10^5$ (group 3) ascites tumour cells which have been charged in vitro with the novel compounds of the formula I ($10^9$ ascites tumour cells are suspended in a solution of 40 mg of the test substance in 20 ml of phosphate-buffered physiological common salt solution (PBS) and after a two-hour incubation at 37° C. the cells are centrifuged and washed twice with PBS; the cells incorporate the test compound into their membrane during this treatment) then in 18 days no tumour growth has occurred. On the 19th day, $10^6$ native Ehrlich ascites tumour cells are administered intraperitoneally to each of the animals. The following effects are observed:

group 1: 8 of the 10 animals survive the 80th day,
group 2: 6 of the 10 animals survive the 80th day,
group 3: the animals die, like the control animals, after 18 days.

The compounds according to the present invention are in addition of low toxicity: even intraperitoneal administration five times at a dosage of 100 mg/kg/day on five successive days were tolerated by the mice apparently without symptoms. Because the doses required for immunostimulation are very small, the therapeutic scope of the novel compounds is very large.

The novel compounds according to the present invention can thus considerably increase the cellular and especially the humoral immunity, both in admixture with the antigen itself (adjuvant effect in the narrower sense) and when administered separately at a different time and at a different site from the antigen injection (systemic immunopotentiation).

The novel compounds according to the present invention may thus be used as adjuvants in admixture with vaccines to improve the success of vaccination and to improve the protection, imparted by humoral antibodies and/or cellular immunity, against infection by bacterial, viral or parasitic causative organisms.

Finally, the novel compounds in admixture with various antigens are suitable as adjuvants in the experimental and industrial manufacture of antisera for therapy and diagnostics and in the induction of immunologically activated lymphocyte populations for cell transfer processes.

Furthermore, the novel compounds can also be used, without simultaneous administration of antigens, to promote immune reactions in humans and animals that are already progressing subliminally. The compounds are accordingly particularly suitable for stimulating the body's defence mechanism, for example in the case of chronic and acute infections or in the case of selective (antigen-specific) immunological defects, and in hereditary and also in acquired general (i.e. not antigen-specific) immunological defective conditions, such as occur in old age, in the course of serious primary diseases and especially after therapy with ionising radiation or with hormones having an immunosuppressive action. The mentioned compounds can thus be administered preferably also in combination with antibiotics, chemotherapeutic agents, or other medicines. Finally, the described novel compounds are also suitable for the general prophylaxis of infectious diseases in humans and animals.

The invention relates also to the combination of the novel compounds according to the invention with antibiotics which causes an increase in the antibiotic activity. For this purpose an effective or subeffective dose of the antibiotic is used, depending on the nature of the latter, for example from approximately 20 to approximately 750 mg per individual dose.

The compounds of the present invention are used in individual doses of approximately 0.1 mg to approximately half the amount of the antibiotic, preferably from 0.5 to 10 mg. The novel compound can be administered up to 24 hours before or after, in many cases up to 7 days before, the antibiotic, but is preferably administered at approximately the same time as the antibiotic.

The antibiotics are administered in the usual manner, such as subcutaneously, intravenously or orally, whilst the novel compounds are usually administered subcutaneously, especially if they are administered separately from the antibiotics.

In this method, individual antibiotics, as well as antibiotic mixtures, may be used. Antibiotic preparations which are characterised in that they contain one or more of the afore-mentioned antibiotics and at least one compound of the present invention contain the usual amounts of antibiotics, for example between 20 and 1000 mg, preferably between approximately 200 and 500 mg, and from 0.1 mg up to half the amount of the antibiotic, preferably from 0.5 to 10 mg, of the muramyl peptide of the formula I. Especially when these preparations are to be administered orally, they may also contain the usual amounts of pharmacological carriers, extenders and/or diluents.

The high antibiotic effect of a combination treatment can be exhibited by "in vivo" tests which are carried out on various types of animals, especially mammals, such as mice. For this purpose, the animals are infected with a lethal or sub-lethal dose of a pathogenic microorganism and then the said new combination preparation or the individual doses of novel compound and antibiotic, are administered. The effect is ascertained as $ED_{50}$, which is that dose at which 50% of the animals survive.

Surprisingly, it has now been found that infection by pathogenic bacilli, especially of gram-negative bacteria which are more difficult to influence, such as, for example, strains of Aerobacter, Brucella, Escherichia, Klebsiella, Malleomyces, Neisseria, Pasteurella, Proteus, Pseudomonas, Shigella and Vibrio, but also of gram-positive bacteria, such as Actinomycetes, Clostridia, Corynebacteria, Diplococci, Mycobacteria or Staphylococci, or of fungi, such as *Candida albicans, Cryptococcus neoformans, Plastomyces dermatitides* or *Hystoplasma capsulatum*, is inhibited to an increased extent.

Of the antibiotics suitable for combination with the compounds according to the invention, especially those from the following groups may be mentioned: β-lactam antibiotics, aminoglycosides, tetracyclines, macrolides, lincomycins, polyene antibiotics, polypeptide antibiotics, anthracyclines, chloramphenicols, thiamphenicols, cycloserines, fusidic acids or rifamycins.

Penicillins, cephalosporins, penems, nocardicines, thienamycins and clavulanic acids may be mentioned as the preferred antibiotics of the β-lactams.

Penicillin antibiotics are especially amoxycillin, ampicillin, carbenicillin, cloxacillin, cyclacillin, dicloxacillin, mecillinam, methicillin, penicillin G, penicillin V, pivampicillin, sulbenicillin, azlocillin, ticarcillin, mezlocillin, pivmecillinam or 6-(4-endoazatricyclo[5.2.2.0$^{2,6}$]undec-8-enyl)-methyleneaminopenicillanic acid.

From the cephalosporin group, there may be mentioned, for example: cefaclor, cefazaflur, cefazolin, cefadroxil, cefoxitin, cefuroxim, cephacetril, cephalexin, cephaloglycin, cephaloridines, cephalotin, cefamandol, cephanon, cephapirin, cefatrizin, cephradin, cefroxadin (7β-[D-2-amino-2-(1,4-cyclohexadienyl)-acetamido]-3-methoxy-3-cephem-4-carboxylic acid), cefsulodin, cefotaxim, cefotiam, ceftezol or cefazedon.

Of the nocardicines, for example nocardicine A may be mentioned, and of the thienamycins and clavulanic acids, for example thienamycin and clavulanic acid may be mentioned.

Of the aminoglycosides, there may be mentioned especially streptomycins, for example streptomycin and streptomycin A, neomycins, for example neomycin B, tobramycins, for example tobramycin or dibekacin, kanamycins (for example mixtures of kanamycin A, B and C), as well as amicacins, gentamycins (for example mixtures of gentamycin A, $C_1$, $C_2$ or $C_{1a}$), or sisomicins, such as sisomicin or netilmicin, and also lividomycin, ribocamycin and paromomycin.

As tetracyclines, especially tetracycline, doxycycline, chlorotetracycline, oxytetracycline and methacycline are to be mentioned.

As macrolides there are to be mentioned, for example, maridomycin, spiramycins, such as spiramycin I, II and III, erythromycins, for example erythromycin, oleandomycins, for example oleandomycin and tetraacetyloleandomycin, and as lincomycins, for example lincomycin and clindamycin.

As polyene antibiotics there are to be mentioned especially amphotericin B and its methyl esters or nystalin.

As polypeptide antibiotics, special mention should be made, for example, of colistin, gramicidin S, polymyxin B, virginamycin, tyrothricin, viomycin or vancomycin.

As rifamycins there come into consideration especially rifamycin S, rifamycin SV or rifamycin B or the semisynthetic derivatives thereof, especially rifampicin.

The present invention relates especially to (a) compounds of the formula I in which $X^1$ and $X^2$ have the meanings given above, $R^1$ represents a radical of the formula Ia in which n, $Z^1$, $Y^1$, $X^3$ and $A^1$ have the meanings given above, each of $R^2$, $R^{12}$ and $R^{13}$, independently of one another, represents hydrogen, acyl other than a radical of the formula Ia in which n represents 1, or a group that can be removed under physiological conditions, $R^3$, $R^4$, $R^5$, $R^7$, $R^8$ and $R^{10}$ have the meanings given above, $R^6$ represents hydrogen or lower alkyl that is unsubstituted or substituted by free or etherified hydroxy or mercapto, by esterified hydroxy or mercapto other than a corresponding group of the formula Id or by free amino or substituted amino other than a corresponding group of the formula Id, by free, esterified or amidated carboxy, by cycloalkyl, by carbocyclic aryl or by nitrogen-containing heteroaryl having 5 or 6 ring members in the heterocyclic ring, or $R^5$ and $R^6$ together represent unsubstituted or substituted 1,3- or 1,4-lower alkylene, and in which each of $R^9$ and $R^{11}$, independently of the other, represents free hydroxy or mercapto, etherified hydroxy or mercapto other than a radical of the formula Ie, or free amino or substituted amino other than a radical of the formula Ie, it being possible for free functional groups to be in protected form, or salts, especially pharmaceutically acceptable salts, of such compounds.

The present invention relates likewise especially to (b) compounds of the formula I in which $X^1$ and $X^2$ have the meanings given above, $R^2$ represents a radical of the formula Ia in which n, $Z^1$, $Y^1$, $X^3$ and $A^1$ have the meanings given above, each of $R^1$, $R^{12}$ and $R^{13}$, independently of one another, represents hydrogen, acyl other than a radical of the formula Ia in which n represents 1, or a group that can be removed under physiological conditions, $R^3$, $R^4$, $R^5$, $R^7$, $R^8$ and $R^{10}$ have the meanings given above, $R^6$ represents hydrogen or lower alkyl that is unsubstituted or substituted by free or etherified hydroxy or mercapto, by esterified hydroxy or mercapto other than a corresponding group of the formula Id, by free amino or substituted amino other than a corresponding group of the formula Id, by free, esterified or amidated carboxy, by cycloalkyl, by carbocyclic aryl or by nitrogen-containing heteroaryl having 5 or 6 ring members in the heterocyclic ring, or $R^5$ and $R^6$ together represent unsubstituted or substituted 1,3- or 1,4-lower alkylene, and in which each of $R^9$ and $R^{11}$, independently of the other, represents free hydroxy or mercapto, etherified hydroxy or mercapto other than a radical of the formula Ie, or free amino or substituted amino other than a radical of the formula Ie, it being possible for free functional groups to be in protected form, or salts, especially pharmaceutically acceptable salts, of such compounds.

The present invention relates also especially to (c) compounds of the formula I in which $X^1$ and $X^2$ have the meanings given above, $R^{13}$ represents a radical of the formula Ia in which n, $Z^1$, $Y^1$, $X^3$ and $A^1$ have the meanings given above, each of $R^1$, $R^2$ and $R^{12}$, independently of one another, represents hydrogen, acyl other than a radical of the formula Ia in which n represents 1, or a group that can be removed under physiological conditions, $R^3$, $R^4$, $R^5$, $R^7$, $R^8$ and $R^{10}$ have the meanings given above, $R^6$ represents hydrogen or lower alkyl that is unsubstituted or substituted by free or etherified hydroxy or mercapto, by esterified hydroxy or mercapto other than a corresponding group of the formula Id, by free amino or substituted amino other than a corresponding group of the formula Id, by free, esterified or amidated carboxy, by cycloalkyl, by carbocyclic aryl or by nitrogen-containing heteroaryl having 5 or 6 ring members in the heterocyclic ring, or $R^5$ and $R^6$ together represent unsubstituted or substituted lower alkylene having 3 or 4 carbon atoms in the chain, and in which each of $R^9$ and $R^{11}$, independently of the other, represents free hydroxy or mercapto, etherified hydroxy or mercapto other than a radical of the formula Ie, or free amino or substituted amino other than a radical of the formula Ie, it being possible for free functional groups to be in protected form, or salts, especially pharmaceutically acceptable salts, of such compounds.

The present invention relates also especially to (d) compounds of the formula I in which $X^1$ and $X^2$ have the meanings given above, each of $R^1$, $R^2$, $R^{12}$ and $R^{13}$, independently of one another, represents hydrogen, acyl other than a radical of the formula Ia in which n represents 1, or a group that can be removed under physiological conditions, $R^3$, $R^4$, $R^5$, $R^7$, $R^8$ and $R^{10}$ have the meanings given above, $R^6$ represents lower alkyl substituted by a radical of the formula Id, in which m, E, $Z^2$, $Y^2$, $X^4$ and $A^2$ have the meanings given above, or $R^6$ represents lower alkyl substituted by a group of the formula Ida in which m, E, $Y^2$, $X^4$ and $A^2$ have the meanings given above, and in which each of $R^9$ and $R^{11}$, independently of the other, represents free hydroxy or mercapto, etherified hydroxy or mercapto other than a radical of the formula Ie, or free amino or substituted amino other than a radical of the formula Ie, it being possible for free functional groups to be in protected form, or salts, especially pharmaceutically acceptable salts, of such compounds.

The invention includes especially hexopyranose compounds, particularly D-glucopyranose compounds of the formula I, in which $X^1$ and $X^2$ have the meanings given above, each of $R^1$, $R^2$, $R^{12}$ and $R^{13}$, independently of one another, represents hydrogen, the acyl radical of an aliphatic, cycloaliphatic, aromatic or araliphatic carboxylic acid, especially of an alkanecarboxylic acid having up to 90 carbon atoms that is unsubstituted or substituted, for example by hydroxy, amino and/or by alkanoylamino, such as higher alkanoylamino, a tri-lower alkylsilyl group or a radical of the formula Ia in which n and $X^3$ have the meanings given above, $Z^1$ represents thiocarbonyl or, preferably, carbonyl, $Y^1$ represents lower alkylene which may be interrupted by iminocarbonyl or oxycarbonyl, and $A^1$ represents a radical of the formula Ib or Ic, in which $R^{15}$ represents an aliphatic radical having at least 7 carbon atoms, $R^{16}$ represents hydrogen and $R^{17}$ represents 2-hydroxyethyl or 1,2-dihydroxyethyl, in which at least one hydroxy group is etherified by an aliphatic radical having at least 7 and up to 90 carbon atoms or is esterified by a corresponding aliphatic acyl radical, or each of $R^{16}$ and $R^{17}$, independently of the other, represents hydroxymethyl etherified by an aliphatic radical having at least 7 and up to 90 carbon atoms or esterified by a corresponding aliphatic acyl radical, $R^3$, $R^4$, $R^5$, $R^7$ and $R^8$ have the meanings given above, $R^6$ represents hydrogen or lower alkyl that is unsubstituted or substituted by a radical of the formula Id in which m, E and $X^4$ have the meanings given above, $Z^2$ represents thiocarbonyl or, especially, carbonyl, $Y^2$ represents lower alkylene which may be interrupted by iminocarbonyl or oxycarbonyl, and $A^2$ represents a radical of the formula Ib or Ic in which $R^{15}$ represents an aliphatic radical having at least 7 carbon atoms, $R^{16}$ represents hydrogen and $R^{17}$ represents 2-hydroxyethyl or 1,2-dihydroxyethyl, in which at least one hydroxy group is esterified by an aliphatic radical having at least 7 and up to 90 carbon atoms or by a corresponding aliphatic acyl radical, or each of $R^{16}$ and $R^{17}$, independently of the other, represents hydroxymethyl etherified by an aliphatic radical having at least 7 and up to 90 carbon atoms or esterified by a corresponding aliphatic acyl radical, or $R^6$ represents lower alkyl substituted by hydroxy or mercapto, by hydroxy or mercapto etherified by an aliphatic radical containing up to 90 carbon atoms, by hydroxy or mercapto that is esterified by an aliphatic acyl radical containing up to 90 carbon atoms and is other than the group of the formula Id, by amino, by amino that is substituted by an acyl radical containing up to 90 carbon atoms and is other than a radical of the formula Id, by free carboxy, by lower alkoxycarbonyl, by carbamoyl, by lower alkylaminocarbonyl, by carboxy-lower alkylaminocarbonyl or by amidated carboxyl of the formula Ida, by phenyl that is unsubstituted or substituted by hydroxy, lower alkoxy or halogen, or by imidazolyl or indolyl, or $R^5$ and $R^6$ together represent 1,3- or 1,4-lower alkylene, each of $R^9$ and $R^{11}$, independently of the other, represents hydroxy, lower alkoxy, amino, lower alkylamino, carboxyl-lower alkylamino, or a radical of the formula Ie, in which $X^5$ and $X^6$ have the meanings given above, $Y^3$ represents lower alkylene which may be interrupted by iminocarbonyl or oxycarbonyl, and $A^3$ represents a radical of the formula Ib or Ic, in which $R^{15}$ represents an aliphatic radical having at least 7 carbon atoms, $R^{16}$ represents hydrogen and $R^{17}$ represents 2-hydroxyethyl or 1,2-dihydroxyethyl, in which at least one hydroxy group is etherified by an aliphatic radical having at least 7 and up to 90 carbon atoms or is esterified by a corresponding aliphatic acyl radical, or each of $R^{16}$ and $R^{17}$, independently of the other, represents hydroxymethyl etherified by an aliphatic radical having at least 7 and up to 90 carbon atoms or esterified by a corresponding aliphatic acyl radical, and $R^{10}$ represents hydrogen, carboxy, lower alkoxycarbonyl, carbamoyl, lower alkylaminocarbonyl or carboxy-lower alkylaminocarbonyl, it being possible for free functional groups to be in protected form, with the proviso that the compounds of the formula I have at least one radical $A^1$, $A^2$ or $A^3$, and with the further proviso that in compounds of the formula I in which at least one of the radicals $R^9$ and $R^{11}$ represents a group of the formula Ie, the pyranose ring is other than a D-glucopyranose ring, or $R^1$ is other than hydrogen, or $X^1$ is other than the radical of the formula $—N(R^{14})—$ and $R^2$ is other than the acyl radical of an aliphatic, cycloaliphatic, aromatic or araliphatic carboxylic acid having up to 90 carbon atoms, especially of an alkanecarboxylic acid that is unsubstituted or substituted, for example, by hydroxy, amino and/or alkanoylamino, such as higher alkanoylamino, or $R^{12}$ is other than hydrogen, or the radical of the formula $—X^2—R^{13}$ is other than hydroxy, or $R^4$ is other than hydrogen, or $R^6$ is other than hydrogen or than lower alkyl that is unsubstituted or substituted by free hydroxy or mercapto, by hydroxy or mercapto etherified by an aliphatic radical containing up to 90 carbon atoms, by esterified hydroxy or mercapto other than a group of the formula Id, by free amino or amino that is substituted by an acyl radical containing up to 90 carbon atoms and is other than a group of the formula Id, by free carboxy, by lower alkylaminocarbonyl, by phenyl that is unsubstituted or substituted by hydroxy, lower alkoxy or halogen, or by imidazolyl or indolyl, or $R^7$ is other than hydrogen, and salts, especially pharmaceutically acceptable salts, of such compounds.

The invention relates especially to the hexopyranose compounds mentioned under (a), (b), (c) and (d), especially D-glucopyranose compounds of the formula I in which $X^1$, $X^2$, $R^1$, $R^2$, $R^3$, $R^4$, $R^5$, $R^6$, $R^7$, $R^8$, $R^9$, $R^{10}$, $R^{11}$, $R^{12}$ and $R^{13}$ have the meanings given in the preceding paragraphs, and salts, especially the pharmaceutically acceptable salts, of such compounds.

The invention relates more especially to D-glucopyranose compounds of the formula If

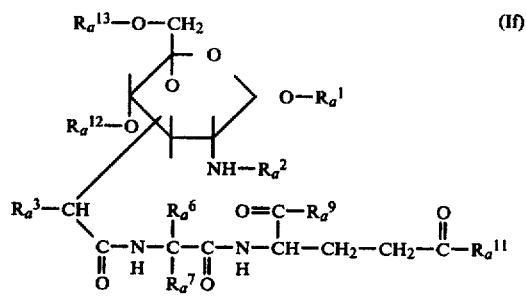

in which $R_a^1$ represents hydrogen, lower alkanoyl or a group of the formula Ia in which n represents 1, $Z^1$ represents carbonyl, $Y^1$ represents lower alkylene which may be interrupted by iminocarbonyl, $X^3$ represents a group of the formula $—O—$ or $—NH—$, and $A^1$ represents a radical of the formula Ib or Ic, in which $R^{15}$ represents an alkyl radical having from 7 to 30 carbon atoms that is unsubstituted or substituted by hydroxy, amino and/or alkanoylamino having up to 30 carbon atoms, $R^{16}$ represents hydrogen and $R^{17}$ represents 2-hydroxyethyl or 1,2-dihydroxyethyl, the hydroxy groups in a radical $R^{17}$ being etherified by an alkyl radical having from 7 to 30 carbon atoms that is unsubstituted or substituted by hydroxy, amino and/or alkanoylamino having up to 30 carbon atoms or being esterified by an alkanoyl radical having from 7 to 90 carbon atoms that is unsubstituted or substituted by hydroxy, amino and/or alkanoylamino having up to 30 carbon atoms, or each of $R^{16}$ and $R^{17}$, independently of the other, represents hydroxymethyl in which the hydroxy group is etherified by an alkyl radical having from 7 to 30 carbon atoms that is unsubstituted or substituted by hydroxy, amino and/or alkanoylamino having up to 30 carbon atoms or is esterified by an alkanoyl radical having from 7 to 90 carbon atoms that is unsubstituted or substituted by hydroxy, amino and/or alkanoylamino having up to 30 carbon atoms, $R_a^2$ represents lower alkanoyl, hydroxy-lower alkanoyl, benzoyl or a group of the formula Ia, in which n, $Z^1$, $Y^1$, $X^3$ and $A^1$ have the meanings given above, $R_a^{12}$ represents hydrogen or lower alkanoyl, $R_a^{13}$ represents hydrogen, alkanoyl or hydroxyalkanoyl having up to 90 carbon atoms, alkanoylaminoalkanoyl having up to 30 carbon atoms or a group of the formula Ia in which n, $Z^1$, $Y^1$, $X^3$ and $A^1$ have the meanings given above, $R_a^3$ and $R_a^7$ represent hydrogen or methyl, $R_a^6$ represents hydrogen or lower alkyl that is unsubstituted or substituted by free hydroxy or mercapto, lower alkoxy, lower alkylthio, alkanoyloxy or hydroxyalkanoyloxy having up to 90 carbon atoms, phenyl, imidazolyl, indolyl or by a group of the formula Id, in which m represents 1, E represents a group of the formula $—O—$ or $—S—$, $Z^2$ represents carbonyl, $Y^2$ represents lower alkylene which may be interrupted by iminocarbonyl, $X^4$ represents a group of the formula $—O—$, and $A^2$ represents a radical of the formula Ib or Ic, in which $R^{15}$ represents an alkyl radical having from 7 to 30 carbon atoms that is unsubstituted or substituted by hydroxy, amino and/or alkanoylamino having up to 30 carbon atoms, $R^{16}$ represents hydrogen and $R^{17}$ represents 2-hydroxyethyl or 1,2-dihydroxyethyl, the hydroxy groups in a radical $R^{17}$ being etherified by an alkyl radical having from 7 to 30 carbon atoms that is unsubstituted or substituted by hydroxy, amino and/or alkanoylamino having up to 30 carbon atoms or being esterified by an alkanoyl radical having from 7 to 90 carbon atoms that is unsubstituted or substituted by hydroxy, amino and/or alkanoylamino having up to 30 carbon atoms, or each of $R^{16}$ and $R^{17}$, independently of the other, represents hydroxymethyl in which the hydroxy group is etherified by an alkyl radical having from 7 to 30 carbon atoms that is unsubstituted or substituted by hydroxy, amino and/or alkanoylamino having up to 30 carbon atoms, or is esterified by an alkanoyl radical having from 7 to 90 carbon atoms that is unsubstituted or substituted by hydroxy, amino and/or alkanoylamino having up to 30 carbon atoms, and each of the radicals $R_a{}^9$ and $R_a{}^{11}$, independently of the other, represents hydroxy, lower alkoxy, amino, lower alkylamino, carboxy-lower alkylamino or a radical of the formula Ie in which $X^5$ represents a group of the formula —O— or —NH—, $Y^3$ represents lower alkylene which may be interrupted by iminocarbonyl, $X^6$ represents a group of the formula —O—, and $A^3$ represents a radical of the formula Ib or Ic, in which $R^{15}$ represents an alkyl radical having from 7 to 30 carbon atoms that is unsubstituted or substituted by hydroxy, amino and/or alkanoylamino having up to 30 carbon atoms, $R^{16}$ represents hydrogen and $R^{17}$ represents 2-hydroxyethyl or 1,2-dihydroxyethyl, the hydroxy groups in a radical $R^{17}$ being etherified by an alkyl radical having from 7 to 30 carbon atoms that is unsubstituted or substituted by hydroxy, amino and/or alkanoylamino having up to 30 carbon atoms, or being esterified by an alkanoyl radical having from 7 to 90 carbon atoms that is unsubstituted or substituted by hydroxy, amino and/or alkanoylamino having up to 30 carbon atoms, or each of $R^{16}$ and $R^{17}$, independently of the other, represents hydroxymethyl in which the hydroxy group is etherified by an alkyl radical having from 7 to 30 carbon atoms that is unsubstituted or substituted by hydroxy, amino and/or alkanoylamino having up to 30 carbon atoms, or is esterified by an alkanoyl radical having from 7 to 90 carbon atoms that is unsubstituted or substituted by hydroxy, amino and/or alkanoylamino having up to 30 carbon atoms, $R_a{}^9$ preferably represents one of the amino groups and $R_a{}^{11}$ preferably represents hydroxy, with the proviso that the compounds have at least one, and preferably only one, radical $A^1$, $A^2$ or $A^3$, and with the further proviso that in compounds of the formula I in which at least one of the radicals $R^9$ and $R^{11}$ represents a group of the formula Ie, $R_a{}^1$ is other than hydrogen, or $R_a{}^2$ is other than lower alkanoyl, hydroxy-lower alkanoyl or benzoyl, or $R_a{}^{12}$ is other than hydrogen, or $R_a{}^{13}$ is other than hydrogen, or $R_a{}^6$ is other than hydrogen or than lower alkyl that is unsubstituted or substituted by free hydroxy or mercapto, by lower alkoxy, lower alkylthio, alkanoyloxy or hydroxyalkanoyloxy having up to 90 carbon atoms, phenyl, imidazolyl or by indolyl, or $R_a{}^7$ is other than hydrogen, and salts, especially pharmaceutically acceptable salts, thereof.

The invention relates especially to the D-glucopyranose compounds of the formula I mentioned under (a), (b), (c) and (d) in which $X^1$ represents a group of the formula —NH—, $X^2$ represents a group of the formula —O—, $R^4$, $R^5$, $R^8$ and $R^{10}$ represent hydrogen, and $R^1$, $R^2$, $R^3$, $R^6$, $R^7$, $R^9$, $R^{11}$, $R^{12}$ and $R^{13}$ have the meanings given in the foregoing section for the radicals $R_a{}^1$, $R_a{}^2$, $R_a{}^3$, $R_a{}^6$, $R_a{}^7$, $R_a{}^9$, $R_a{}^{11}$, $R_a{}^{12}$ and $R_a{}^{13}$, respectively, and salts thereof, especially pharmaceutically acceptable salts.

The invention relates especially to the novel compounds of the formula I described in the Examples, and salts thereof, especially pharmaceutically acceptable salts.

Unless otherwise stated, the terms used hereinafter for the substituents have the meanings given above.

The novel compounds of the formula I and their salts may be obtained according to methods that are known per se.

They may thus be obtained if a compound of the formula II

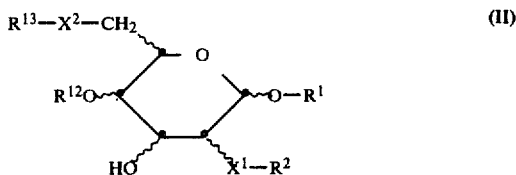

in which functional groups which may be present, with the exception of the free hydroxy group in the 4-position of the pyranose moiety, may be in protected form, or a metal compound thereof, is reacted with a compound of the formula III

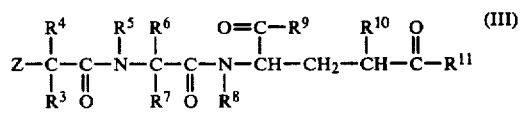

in which Z represents a reactive esterified hydroxy group, and functional groups which may be present therein may be protected by protecting groups, protecting groups which may be present are removed and, if desired, a resulting compound of the formula I is converted into a different compound of the formula I and/or, if desired, a resulting salt is converted into the free compound or into a different salt and/or, if desired, a resulting free compound is converted into a salt and/or, if desired, a resulting mixture of isomers is separated into the individual isomers.

A reactive esterified hydroxy group is especially a hydroxy group esterified by a strong inorganic or organic acid, especially a hydroxy group esterified by a hydrohalic acid, such as hydrochloric, hydrobromic or, especially, hydriodic acid, or by an aliphatic or aromatic sulphonic acid, such as methanesulphonic acid or p-toluenesulphonic acid.

A metal compound is especially a corresponding alkali metal derivative, for example a sodium or potassium derivative. It may be manufactured, for example, by treating a compound of the formula II with a suitable metal base, such as a corresponding alkali metal compound, such as sodium hydride, sodium amide or butyl-lithium.

Protecting groups for functional groups which may be present are, for example, the protecting groups mentioned above.

The starting materials used are known or may be manufactured in a manner known per se, for example analogously to the processes described herein.

The novel compounds may also be obtained if a compound of the formula IV

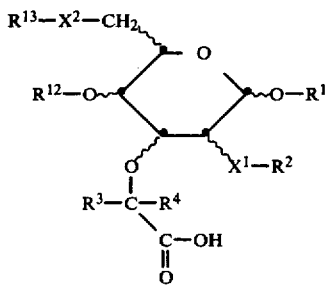

(IV)

in which functional groups which may be present, with the exception of the free carboxyl group, may be in protected form, or a reactive carboxyl derivative thereof, is reacted with a compound of the formula V

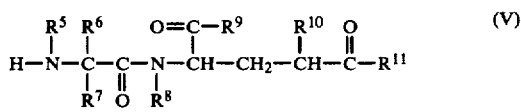

(V)

in which free functional groups which may be present, with the exception of the amino group of the formula $HN(R^5)$—, may be in protected form, or with a reactive derivative thereof, and protecting groups which may be present are removed and, if desired, the above-mentioned additional process steps are carried out.

Reactive carboxyl derivatives are especially reactive activated esters or reactive anhydrides, and also reactive cyclic amides of corresponding acids of the formula IV; in this case reactive derivatives of acids of the formula IV may also be formed in situ.

Activated esters of acids are especially esters that are unsaturated at the linking carbon atom of the esterifying radical, for example those of the vinyl ester type, such as actual vinyl esters (which may be obtained, for example, by transesterifying a corresponding ester with vinyl acetate; activated vinyl ester method), carbamoylvinyl esters (which may be obtained, for example, by treating the corresponding acid with an isoxazolium reagent; 1,2-oxazolium or Woodward method), or 1-lower alkoxyvinyl esters (which may be obtained, for example, by treating the corresponding acid with a lower alkoxyacetylene; ethoxyacetylene method), or esters of the amidino type, such as N,N'-di-substituted amidino esters (which may be obtained, for example, by treating the corresponding acid with a suitable N,N'-di-substituted carbodiimide, for example N,N'-dicyclohexylcarbodiimide; carbodiimide method), or N,N-di-substituted amidino esters (which may be obtained, for example, by treating the corresponding acid with an N,N-di-substituted cyanamide; cyanamide method), suitable aryl esters, especially phenyl esters suitably substituted by substituents that attract electrons (which may be obtained, for example, by treating the corresponding acid with a suitably substituted phenol, for example 4-nitrophenol, 4-methylsulphonylphenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl ester method), cyanomethyl esters (which may be obtained, for example, by treating the corresponding acid with chloroacetonitrile in the presence of a base; cyanomethyl ester method), thio esters, especially phenylthio esters optionally substituted, for example, by nitro (which may be obtained, for example, by treating the corresponding acid with thiophenols optionally substituted, for example by nitro, inter alia with the aid of the anhydride or carbodiimide method; activated thiol ester method), or amino or amido esters (which may be obtained, for example, by treating the corresponding acid with an N-hydroxyamino or N-hydroxyamido compound, for example N-hydroxysuccinimide, N-hydroxypiperidine, N-hydroxyphthalimide or 1-hydroxybenztriazole, for example according to the anhydride or carbodiimide method; activated N-hydroxy ester method).

Anhydrides of acids of the formula IV may be symmetric and, preferably, mixed anhydrides of these acids, thus, for example, anhydrides with inorganic acids, such as acid halides, especially acid chlorides (which may be obtained, for example, by treating the corresponding acid with thionyl chloride, phosphorus pentachloride or oxalyl chloride; acid chloride method), azides (which may be obtained, for example, from a corresponding acid ester via the corresponding hydrazide and by treating the hydrazide with nitrous acid; azide method), anhydrides with carbonic acid semi-derivatives, such as with corresponding esters, for example carbonic acid lower alkyl semi-esters (which may be obtained, for example, by treating the corresponding acid with halo-, such as chloroformic acid lower alkyl esters or with a 1-lower alkoxycarbonyl-2-lower alkoxy-1,2-dihydroquinoline, for example 1-lower alkoxycarbonyl-2-ethoxy-1,2-dihydroquinoline; mixed O-alkyl carbonic acid anhydrides method), or anhydrides with dihalogenated, especially dichlorinated, phosphoric acid (which may be obtained, for example, by treating the corresponding acid with phosphorus oxychloride; phosphorus oxychloride method), or anhydrides with organic acids, such as mixed anhydrides with organic carboxylic acids (which may be obtained, for example, by treating the corresponding acid with an optionally substituted lower alkane- or phenylalkane-carboxylic acid halide, for example phenylacetic acid, pivalic acid or trifluoroacetic acid chloride; mixed carboxylic acid anhydrides method), or with organic sulphonic acids (which may be obtained, for example, by treating a salt, such as an alkali metal salt, of the corresponding acid with a suitable organic sulphonic acid halide, such as lower alkane- or aryl-, for example methane- or p-toluene-sulphonic acid chloride; mixed sulphonic acid anhydrides method) and symmetric anhydrides (which may be obtained, for example, by condensation of the corresponding acid in the presence of a carbodiimide or of 1-diethylaminopropine; symmetric anhydrides method).

Suitable cyclic amides are especially amides with five-membered diazacycles of aromatic character, such as amides with imidazoles, for example imidazole (which may be obtained, for example, by treating the corresponding acid with N,N'-carbonyldiimidazole; imidazolide method), or pyrazoles, for example 3,5-dimethylpyrazole (which may be obtained, for example via the acid hydrazide by treatment with acetyl acetone; pyrazolide method).

The amino group present in a starting material of the formula V and participating in the reaction is preferably in free form, especially if the carboxy group in the reactant of the formula IV is in reactive form; alternatively, however, it may be self-derivatised, for example it may be activated by reaction with a phosphite, such as diethyl chlorophosphite, 1,2-phenylene chlorophosphite, ethyl dichlorophosphite, ethylene chlorophosphite or tetraethyl pyrophosphite, or, for example, it may be in the form of an organic silylamino group, such as a tri-lower alkylsilylamino group, especially a trimethylsilylamino group.

In this case, the optionally derivatised amino group in a starting material of the formula V is preferably acylated by treatment with an anhydride, especially with a mixed anhydride, or with an activated ester or a cyclic amide of an acid of the formula IV. As already mentioned, derivatives of acids of the formula IV may be formed also in situ. Thus, for example, N,N'-disubstituted amidino esters may be formed in situ by reacting a mixture of the starting material of the formula V and the acid of the formula IV in the presence of a suitable N,N'-disubstituted carbodiimide, for example, N,N'-dicyclohexylcarbodiimide. It is also possible to form amino or amido esters of acids of the formula IV in the presence of the starting material of the formula V to be acylated by reacting a mixture of the corresponding acid and amino starting materials in the presence of an N,N'-disubstituted carbodiimide, for example N,N'-dicyclohexylcarbodiimide, and an N-hydroxyamine or N-hydroxyamide, for example N-hydroxysuccinimide, optionally in the presence of a suitable base, for example 4-dimethylaminopyridine.

Protecting groups of functional groups which may be present are, for example, the protecting groups mentioned above.

The acylation reaction may be carried out in a manner known per se, the reaction conditions being dependent primarily on the type of acylating agent used, customarily in the presence of a suitable solvent or diluent or a mixture thereof, and, if necessary, in the presence of a condensation agent which, for example when using an anhydride as acylating agent, may optionally also be an acid-binding agent, while cooling or heating, for example in a temperature range of from approximately $-30°$ to approximately $+150°$ C., in a closed reaction vessel and/or under an inert gas atmosphere, for example a nitrogen atmosphere.

The starting materials used are known or may be manufactured in a manner known per se. Thus, for example, a compound of the formula II can be reacted with a 2-halo-2-$R^3$-2-$R^4$-acetic acid, in which the carboxyl group may be in protected form, and, if desired, the carboxyl-protecting group can be removed.

A further method for the manufacture of the novel compounds consists in reacting a compound of the formula VI

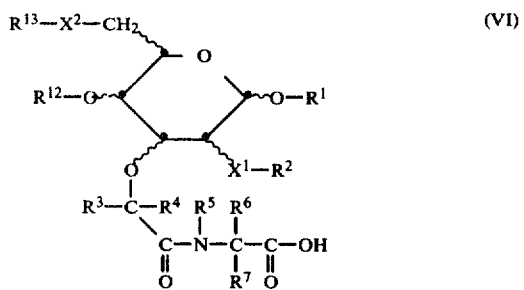

in which free functional group which may be present, with the exception of the free carboxyl group, may be in protected form, or a reactive carboxyl derivative thereof, with a compound of the formula VII

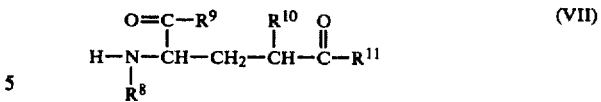

in which free functional groups which may be present, with the exception of the amino group of the formula HN($R^8$)—, are in protected form, or with a reactive derivative thereof, and removing protecting groups which may be present and, if desired, carrying out the above-mentioned additional process steps.

The condensation may be carried out analogously to the foregoing process, wherein reactive carboxyl derivatives of acids of the formula VI, for example acid anhydrides, acid amides and activated esters; reactive derivatives of the amino compound VII, for example derivatives obtainable by reaction with a phosphite; and protecting groups of free functional groups which may be present are preferably the derivatives and protecting groups mentioned above.

The starting materials may be manufactured in a manner known per se, for example by reacting a compound of the formula II in which free functional groups which may be present, with the exception of the hydroxy group, may be in protected form, with a compound of the formula VIII

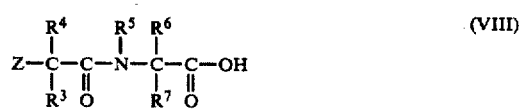

in which Z has the meaning given above and any functional groups present may be in protected form, or reacting a compound of the formula IV in which free functional groups which may be present, with the exception of the carboxy group, may be in protected form, or a reactive carboxyl derivative thereof, with a compound of the formula IX

in which free functional groups, with the exception of the amino group of the formula HN($R^5$)—, may be in protected form, or with a reactive derivative thereof. The reactions may be carried out, for example, in the manner described above.

Compounds of the formula I in which at least one of the radicals $R^1$, $R^2$, $R^{12}$ and $R^{13}$ represents a group of the formula Ia in which n represents 1, and $Z^1$, $Y^1$, $X^3$ and $A^1$ have the meanings given above, and each of the other radicals, independently of one another, represents hydrogen, acyl other than a radical of the formula Ia, a group that can be removed under physiological conditions or a radical of the formula Ia, may be manufactured, for example, if a compound of the formula I in which at least one of the groups $R^1$, $R^2$, $R^{12}$ and $R^{13}$ represents hydrogen and each of the others, independently of one another, represents hydrogen, acyl other than a radical of the formula Ia, a group that can be removed under physiological conditions or a radical of the formula Ia, and in which the remaining substituents $R^3$, $R^4$, $R^5$, $R^6$, $R^7$, $R^8$, $R^9$, $R^{10}$, $R^{11}$, $X^1$ and $X^2$ have the meanings given above, it being possible for free functional groups which may be present, with the exception of the group(s) participating in the reaction, to be in protected form, or a reactive derivative thereof, is reacted with an acid of the formula HO—$Z^1$—$Y^1$—$X^3$—$A^1$ (X), in which $Z^1$, $Y^1$, $X^3$ and $A^1$ have the meanings given above, it being possible for free functional groups which may be present, with the exception of the acid group of the formula HO—$Z^1$—, to be in protected form, or with a reactive acid derivative thereof, and protecting groups which may be present in a resulting compound of the formula I are removed and, if desired, additional process steps are carried out.

In starting materials having at least one free hydroxy group participating in the reaction, for example in the 1-position of the sugar moiety, this may also be in the form of a reactive esterified hydroxy group, especially in the form of a hydroxy group esterified by an inorganic acid, for example in the form of halogen, such as chlorine, bromine or iodine, or in the form of a hydroxy group esterified by a strong organic acid, such as a corresponding sulphonic acid, for example in the form of lower alkylsulphonyloxy, especially methylsulphonyloxy, or arylsulphonyloxy, especially p-methylphenylsulphonyloxy, or it may be activated by removing the proton with a strong base, that is to say, it may be in the form of a metal oxy group, for example an alkali metal oxy group.

An amino group, participating in the reaction, in a starting material may be converted, for example by reaction with a phosphite, for example according to the phosphite or phosphorazo method, into a reactive phosphorus-substituted amino group, or by reaction with, for example, phosgene, into a reactive isocyanate group.

Protecting groups for functional groups which may be present are, for example, the protecting groups mentioned above.

The acylation of the free hydroxy and/or amino group in a starting compound of the formula I used in the present process variant may be carried out, for example, according to the acylation process described above, that is to say, preferably with a suitable derivative of an acid of the formula X that may be formed in situ, it being possible to use as derivative of such an acid also a salt, such as a metal salt, for example an alkali metal salt, such as a sodium or potassium salt, or an ammonium salt.

Depending on whether an optionally derivatised hydroxy group or amino group in a starting material is acylated, one or the other derivative of an acid of the formula X is more suitable as acylating agent. Whilst an optionally derivatised amino group in a starting material can be acylated preferably by treatment with an anhydride, especially a mixed anhydride, but also with an activated ester or a cyclic amide of an acid of the formula X, there is used for the acylation of the optionally derivatised hydroxy group in a starting material especially activated esters, especially amino or amido esters, and also anhydrides, especially mixed anhydrides of acids of the formula X. Starting materials having a hydroxy group in reactive esterified form are customarily reacted with a salt of an acid of the formula X.

The starting materials are known or may be manufactured in a manner known per se.

Compounds of the formula I in which at least one of the radicals $R^1$, $R^2$, $R^{12}$ and $R^{13}$ represents a group of the formula Ia in which n represents 1, $Y^1$ represents unsubstituted or substituted alkylene which is interrupted by iminocarbonyl or oxycarbonyl, and $Z^1$, $X^3$ and $A^1$ have the meanings given above, and each of the other radicals, independently of one another, represents hydrogen, acyl other than a radical of the formula Ia, a group that can be removed under physiological conditions or a radical of the formula Ia, or salts thereof, may be manufactured, for example, by reacting a compound of the formula I in which at least one of the groups $R^1$, $R^2$, $R^{12}$ and $R^{13}$ represents a radical of the formula —$Z^1$—$Y_a^1$—$R_x$ (Iaa), and each of the other radicals, independently of one another, represents hydrogen, acyl other than a radical of the formula Ia, a group that can be removed under physiological conditions or a radical of the formula Ia, with a compound of the formula —$R_y$—$Y_b^1$—$X^3$—$A^1$ (XI), wherein $Z^1$, $X^3$ and $A^1$ have the meanings given above, and each of $Y_a^1$ and $Y_b^1$, independently of the other, represents unsubstituted or substituted alkylene, and wherein one of the groups $R_x$ and $R_y$ represents hydroxy or amino of the formula —NH($R^{14}$) that is free or present in reactive derivatised form, and the other represents carboxy that is free or present in reactive derivatised form, whilst the remaining substituents $R^1$, $R^2$, $R^3$, $R^4$, $R^5$, $R^6$, $R^7$, $R^8$, $R^9$, $R^{10}$, $R^{11}$, $X^1$ and $X^2$ have the meanings given above, it being possible for free functional groups, with the exception of the functional groups participating in the reaction, to be in protected form, and removing any protecting groups present in a resulting compound of the formula I and, if desired, carrying out additional process steps.

A hydroxy group $R_x$ or $R_y$ is preferably in free form but may alternatively be in derivatised form, for example, as described above, in the form of a reactive esterified hydroxy group, and also in the form of a metal oxy group, such as an alkali metal oxy group, for example a sodium oxy or potassium oxy group. A derivatised amino group $R_x$ or $R_y$ may be, for example, as described above, a phosphorus-substituted amino group.

A carboxyl group $R_x$ or $R_y$ is preferably present in reactive derivatised form, especially in one of the above-described reactive, anhydridised, activated esterified or cyclically amidated forms, and also in salt form, for example in alkali metal salt form.

Protecting groups for functional groups which may be present in the starting materials are, for example, the protecting groups mentioned above.

The reaction is carried out, for example, as described above.

The starting materials may be manufactured according to methods known per se, for example analogously to the processes described herein.

Compounds of the formula I in which at least one of the radicals $R^1$, $R^2$, $R^{12}$ and $R^{13}$ represents a group of the formula Ia in which n represents 1 and $Z^1$, $Y^1$, $X^3$ and $A^1$ have the meanings given above, and each of the other radicals, independently of one another, represents hydrogen, acyl other than a radical of the formula Ia, a group that can be removed under physiological conditions or a radical of the formula Ia, or salts thereof, may be manufactured, for example, by reacting a compound of the formula I in which at least one of the groups $R^1$, $R^2$, $R^{12}$ and $R^{13}$ represents a radical of the formula $Z^1$—$Y^1$—$X^3$—H (Iab), in which $Z^1$, $Y^1$ and $X^3$ have the meanings given above, and each of the others, independently of one another, represents hydrogen, acyl other than a radical of the formula Ia, a group that can be removed under physiological conditions or a radical of the formula Ia, or a reactive derivative thereof, with a compound of the formula XII or XIII

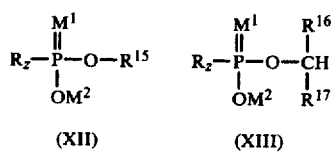

(XII)        (XIII)

in which $R_z$ represents hydroxy which is optionally present in reactive derivatised form, $=M^1$ represents a pair of electrons or oxo, and $M^2$ represents hydrogen or a removable group, and $R^{15}$, $R^{16}$ and $R^{17}$ have the meanings given above, if necessary in the presence of an oxidising agent, wherein in the starting materials the remaining substituents $R^3$, $R^4$, $R^5$, $R^6$, $R^7$, $R^8$, $R^9$, $R^{10}$, $R^{11}$, $X^1$ and $X^2$ have the meanings given above and free functional groups, with the exception of the groups participating in the reaction, may be in protected form, and removing protecting groups in a resulting compound of the formula I and, if desired, carrying out additional process steps.

If $=M^1$ represents a pair of electrons and $M^2$ represents hydrogen, the compounds of the formulae XII and XIII may also be in the form of tautomers of the formulae XIIa and XIIIa

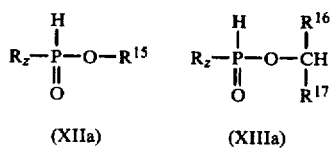

(XIIa)        (XIIIa)

respectively.

The group $R_z$ in the starting materials of the formulae XII and XIII may, in addition to a hydroxy group, which may be present also in a salt form, for example as a metal oxy group, such as an alkali metal oxy group, for example a sodium oxy or potassium oxy group, also represent etherified hydroxy, such as lower alkoxy, for example methoxy or ethoxy, or phenoxy, or esterified hydroxy, such as hydroxy esterified by a strong acid, for example halogen, such as chlorine.

A removable group $M^2$ forms, together with the oxy group, an etherified hydroxy group, especially lower alkoxy, for example methoxy or ethoxy, and also phenoxy.

In a starting material having a group of the formula Iab, the hydroxy or amino group of the formula $-X^3-H$ may be in reactive derivatised form. If the group of the formula $-X^3-H$ represents hydroxy, this may be, for example, in the form of a reactive esterified hydroxy group, such as one of the groups of this type mentioned above, or alternatively in the form of a metal oxy group, such as an alkali metal oxy group, for example a sodium oxy or potassium oxy group. A reactive derivatised amino group is, for example, an amino group substituted by phosphorus as described above.

Protecting groups for functional groups which may be present in the starting materials are, for example, the protecting groups mentioned above.

The reaction is carried out in a manner known per se, preferably in the presence of an acid-binding agent, such as pyridine, tri-lower alkylamine, for example trimethylamine or triethylamine, or in the presence of an imidazole or an inorganic base, such as sodium or potassium hydroxide, or in the presence of an alkali metal alkoxide, such as sodium or potassium alkoxide, there being used as solvent preferably an aprotic solvent, such as dimethyl sulphoxide or acetonitrile.

If in a starting material of the formula XII or XIII the group $=M^1$ represents a pair of electrons, the reaction is carried out in the presence of a suitable, especially a weak, oxidising agent, for example a peracid, such as perbenzoic acid, or an alkyl hydroperoxide.

The removal of a removable group $M^2$ is customarily carried out together with the removal of other protecting groups, preferably by hydrogenolysis or by acid hydrolysis.

The starting materials are known and may be manufactured in a manner known per se, for example analogously to any one of the processes described herein.

Compounds of the formula I in which at least one of the radicals $R^1$, $R^2$, $R^{12}$ and $R^{13}$ represents a group of the formula Ia in which n represents 1 and $Z^1$, $Y^1$, $X^3$ and $A^1$ have the meanings given above, and each of the other radicals, independently of one another, represents hydrogen, acyl other than a radical of the formula Ia, a group that can be removed under physiological conditions or a radical of the formula Ia, or salts thereof, may be manufactured, for example, by reacting a compound of the formula I in which at least one of the groups $R^1$, $R^2$, $R^{12}$ and $R^{13}$ represents a radical of the formula

in which $R_z$ represents hydroxy which is optionally present in reactive derivatised form, $=M^1$ represents a pair of electrons or oxo, and $M^2$ represents hydrogen or a removable group, and $Z^1$, $Y^1$ and $X^3$ have the meanings given above, and each of the other groups, independently of one another, represents hydrogen, acyl other than a radical of the formula Ia, a group that can be removed under physiological conditions or a radical of the formula Ia, with a compound of the formula XIV or XV

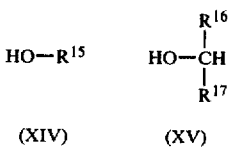

(XIV)        (XV)

in which $R^{15}$, $R^{16}$ and $R^{17}$ have the meanings given above, or with a derivative thereof, if necessary in the presence of an oxidising agent, wherein in the starting materials the remaining substituents $R^3$, $R^4$, $R^5$, $R^6$, $R^7$, $R^8$, $R^9$, $R^{10}$, $R^{11}$, $X^1$ and $X^2$ have the meanings given above and free functional groups, with the exception of the groups participating in the reaction, may be in protected form, and removing any protecting groups present in a resulting compound of the formula I and, if desired, carrying out additional process steps.

If $=M^1$ represents a pair of electrons, and $M^2$ represents hydrogen, the phosphorus group in a radical of the formula Iac may also be in tautomeric form as a group of the formula

The group $R_z$ may, in addition to hydroxy, also represent hydroxy that is present in salt form, or reactive etherified or esterified hydroxy, as described above.

A removable group $M^2$ represents a radical etherifying an organic hydroxy group and is especially lower alkyl, such as methyl or ethyl, and also phenyl.

In a derivative of a compound of the formula XIV or XV, the hydroxy group is in reactive derivatised form, for example in the form of a reactive esterified hydroxy group or in the form of a metal oxy group, for example an alkali metal oxy group.

Protecting groups for functional groups which may be present in the starting materials are, for example, the protecting groups mentioned above.

The reaction is carried out in a manner known per se, for example as described above, and, in the case when in a starting material $=M^1$ represents a pair of electrons, the operation is carried out in the presence of an oxidising agent, for example one of those mentioned above.

The starting materials may be manufactured in a manner known per se, for example analogously to the processes described herein.

Compounds of the formula I in which at least one of the radicals $R^1$, $R^2$, $R^{12}$ and $R^{13}$ represents a group of the formula Ia in which n represents 0 and $A^1$ has the meaning given above, and each of the other radicals, independently of one another, represents hydrogen, acyl other than a radical of the formula Ia, a group that can be removed under physiological conditions or a radical of the formula Ia, or salts thereof, may be manufactured, for example, by reacting a compound of the formula I in which at least one of the groups $R^1$, $R^2$, $R^{12}$ and $R^{13}$ represents hydrogen, and each of the other radicals, independently of one another, represents hydrogen, acyl other than a radical of the formula Ia, a group that can be removed under physiological conditions or a radical of the formula Ia, or a derivative thereof, with a compound of the formula XII or XIII in which $R_z$ represents hydroxy which is optionally present in reactive form, $=M^1$ represents a pair of electrons of oxo, and $M^2$ represents hydrogen or a removable group, and $R^{15}$, $R^{16}$ and $R^{17}$ have the meanings given above, if necessary in the presence of an oxidising agent, wherein in the starting materials the remaining substituents $R^3$, $R^4$, $R^5$, $R^6$, $R^7$, $R^8$, $R^9$, $R^{10}$, $R^{11}$, $X^1$ and $X^2$ have the meanings given above and free functional groups, with the exception of the groups participating in the reaction, may be in protected form, and removing any protecting groups present in a resulting compound of the formula I and, if desired, carrying out additional process steps.

In a starting material having at least one hydroxy group of the formula $-O-R^1$, $-X^1-R^2$, $-O-R^{12}$ or $-X^2-R^{13}$, or having an amino group of the formula $-X^1-R^2$ or $-X^2-R^{13}$, such a group may be in reactive derivatised form; a hydroxy group may be, for example, in the form of a reactive esterified hydroxy group or in the form of a metal oxy group, for example an alkali metal oxy group, and in amino group may be, for example, in phosphorus-substituted form (which can be formed, for example, by treatment with a phosphite).

If in a starting material of the formula XII or XIII $=M^1$ represents a pair of electrons and $M^2$ represents hydrogen, the compound may be present in the tautomeric form of the formula XIIa or XIIIa, respectively.

The group $R_z$ may, in addition to hydroxy, also be in the form of hydroxy that is present in salt form, or in the form of reactive etherified or esterified hydroxy, as described above.

A removable group $M^2$ represents an organic radical etherifying a hydroxy group and is especially lower alkyl, such as methyl or ethyl, and also phenyl.

Protecting groups for functional groups which may be present in the starting materials are, for example, the protecting groups mentioned above.

The reaction is carried out in a manner known per se, for example as described above, and, in the case when $=M^1$ represents a pair of electrons, the operation is carried out in the presence of an oxidising agent, for example one of those mentioned above.

The starting materials may be manufactured in a manner known per se, for example analogously to the processes described herein.

Compounds of the formula I in which $R^6$ represents lower alkyl that is substituted by a radical of the formula Id in which m represents 1 and the groups E, $Z^2$, $Y^2$, $X^4$ and $A^2$ have the meanings given above, or salts thereof, may be manufactured, for example, by reacting a compound of the formula I in which $R^6$ represents lower alkyl that is substituted by a group of the formula $-E-H$ (Idb), in which E has the meaning given above, or a reactive derivative thereof, with an acid of the formula $HO-Z^2-Y^2-X^4-A^2$ (XVI), in which $Z^2$, $Y^2$, $X^4$ and $A^2$ have the meanings given above, or with a reactive derivative thereof, wherein in the starting materials the remaining substituents $R^1$, $R^2$, $R^3$, $R^4$, $R^5$, $R^7$, $R^8$, $R^9$, $R^{10}$, $R^{11}$, $R^{12}$, $R^{13}$, $X^1$ and $X^2$ have the meanings given above and functional groups which may be present, with the exception of the groups participating in the reaction, may be in protected form, and removing any protecting groups in a resulting compound of the formula I and, if desired, carrying out additional process steps.

In a derivative of a starting material having a group of the formula Idb, a corresponding hydroxy group is in derivatised form, for example, as described above, in the form of a reactive hydroxy group, or in salt form, for example in the form of a metal oxy group, such as an alkali metal oxy group, for example a sodium oxy or potassium oxy group, whilst a corresponding mercapto group may be derivatised inn analogous manner. A derivatised amino group of the formula Idb is, for example, an amino group substituted by phosphorus as described above.

A reactive derivatised acid group of the formula $HO-Z^2-$ (Idc) is especially a corresponding activated ester or anhydride group, but may also be a corresponding cyclic acid amide group, it being possible to form these reactive derivatised groups also in situ. Examples of such reactive groups are, for example, the radicals described above.

Protecting groups for functional groups which may be present in the starting materials are, for example, the protecting groups mentioned above.

The reaction is carried out in a manner known per se, for example as described above.

The starting materials are known or may be manufactured in a manner known per se.

Compounds of the formula I in which $R^6$ represents lower alkyl that is substituted by a radical of the formula Id in which m represents 1, $Y^2$ represents unsubstituted or substituted alkylene which is interrupted by iminocarbonyl or oxycarbonyl, and the groups E, $Z^2$, $X^4$ and $A^2$ have the meanings given above, or salts thereof, may be manufactured by reacting a compound of the formula I in which $R^6$ represents lower alkyl that is substituted by the group $-E-Z^2-Y_a^2-R_x$ (Idc) with a compound of the formula $R_y-Y_b^2-X^4-A^2$ (XVII), wherein each of $Y_a^2$ and $Y_b^2$, independently of the other, represents unsubstituted or substituted alkylene, and wherein one of the groups $R_x$ and $R_y$ represents hydroxy or amino of the formula $-NH(R^{14})$ that is free or present in reactive derivatised form, and the other represents carboxy that is free or present in reactive derivatised form, and E, $Z^2$, $X^4$ and $A^2$ have the meanings given above, whilst the remaining substituents of the starting materials $R^1$, $R^2$, $R^3$, $R^4$, $R^5$, $R^7$, $R^8$, $R^9$, $R^{10}$, $R^{11}$, $R^{12}$, $R^{13}$, $X^1$ and $X^2$ have the meanings given above, and functional groups which may be present, with the exception of the groups participating in the reaction, may be in protected form, removing any protecting groups present in a resulting compound of the formula I and, if desired, carrying out additional process steps.

A hydroxy group $R_x$ or $R_y$ may be in derivatised form, for example, as described above, in the form of a reactive esterified hydroxy group, and also in the form of a metal oxy group, such as an alkali metal oxy group, for example a sodium oxy or potassium oxy group. A derivatised amino group $R_x$ or $R_y$ may be, for example, an amino group substituted by phosphorus as described above.

A carboxyl group $R_x$ or $R_y$ is preferably in reactive derivatised form, especially in one of the reactive, anhydridised, activated esterified or cyclically amidated forms described above, and also in salt form, for example in alkali metal salt form.

Protecting groups for functional groups which may be present in the starting materials are, for example, the protecting groups mentioned above.

The reaction is carried out in manner known per se, for example as described above.

The starting materials may be manufactured in a manner known per se, for example analogously to the processes described.

Compounds of the formula I in which $R^6$ represents lower alkyl that is substituted by a radical of the formula Id in which m represents 1 and the groups E, $Z^2$, $Y^2$, $X^4$ and $A^2$ have the meanings given above, or salts thereof, may be manufactured, for example, by reacting a compound of the formula I in which $R^6$ represents lower alkyl that is substituted by a group of the formula $-E-Z^2-Y^2-X^4-H$ (Idd), in which E, $Z^2$, $Y^2$ and $X^4$ have the meanings given above, or a reactive derivative thereof, with a compound of the formula XII or XIII in which $R_z$ represents hydroxy which is optionally present in reactive derivatised form, $=M^1$ represents a pair of electrons or oxo, and $M^2$ represents hydrogen or a removable group, and $R^{15}$, $R^{16}$ and $R^{17}$ have the meanings given above, if necessary in the presence of an oxidising agent, wherein in the starting materials the remaining substituents $R^1$, $R^2$, $R^3$, $R^4$, $R^5$, $R^7$, $R^8$, $R^9$, $R^{10}$, $R^{11}$, $R^{12}$, $R^{13}$, $X^1$ and $X^2$ have the meanings given above and functional groups which may be present, with the exception of the groups participating in the reaction, may be in protected form, and removing any protecting groups present in a resulting compound of the formula I and, if desired, carrying out additional process steps.

If $=M^1$ represents a pair of electrons and $M^2$ represents hydrogen, the compounds of the formulae XII and XIII may also be in the form of tautomers of the formulae XIIa and XIIIa, respectively.

The group $R_z$ may, in addition to hydroxy, also represent hydroxy that is present in salt form or reactive etherified or esterified hydroxy, as described above.

A removable group $M^2$ represents a radical etherifying an organic hydroxy group and is especially lower alkyl, such as methyl or ethyl, and also phenyl.

In a starting material having a group of the formula Idd, the hydroxy or amino group of the formula $-X^4-H$ may be in reactive derivatised form. If the group of the formula $-X^4-H$ represents hydroxy, this may be, for example, in the form of a reactive esterified hydroxy group, such as one of the groups of this type mentioned above, or alternatively in the form of a metal oxy group, such as an alkali metal oxy group, for example a sodium oxy or potassium oxy group, whilst a corresponding derivatised amino group may be, for example, an amino group substituted by phosphorus, such as one of those mentioned above.

Protecting groups for functional groups which may be present in the starting materials are, for example, the protecting groups mentioned above.

The reaction is carried out in a manner known per se, for example as described above, and if in a starting material $=M^1$ represents a pair of electrons, the operation is carried out in the presence of an oxidising agent, for example one of those mentioned above.

The starting materials may be manufactured in a manner known per se, for example analogously to the processes described herein.

Compounds of the formula I in which $R^6$ represents lower alkyl that is substituted by a radical of the formula Id in which m represents 1 and the groups E, $Z^2$, $Y^2$, $X^4$ and $A^2$ have the meanings given above, or salts thereof, may be manufactured, for example, by reacting a compound of the formula I in which $R^6$ represents lower alkyl that is substituted by a group of the formula

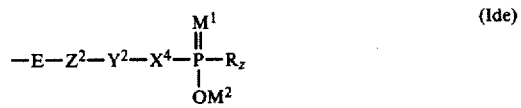
(Ide)

in which $R_z$ represents hydroxy which is optionally present in reactive derivatised form, $=M^1$ represents a pair of electrons or oxo, and $M^2$ represents hydrogen or a removable group, and E, $Z^2$, $Y^2$ and $X^4$ have the meanings given above, with a compound of the formula XIV or XV in which $R^{15}$, $R^{16}$ and $R^{17}$ have the meanings given above, or with a derivative thereof, if necessary in the presence of an oxidising agent, wherein in the starting materials the remaining substituents $R^1$, $R^2$, $R^3$, $R^4$, $R^5$, $R^7$, $R^8$, $R^9$, $R^{10}$, $R^{11}$, $R^{12}$, $R^{13}$, $X^1$ and $X^2$ have the meanings given above and free functional groups, with the exception of the groups participating in the reaction, may be in protected form, and removing any protecting groups present in a resulting compound of the formula I and, if desired, carrying out additional process steps.

If $=M^1$ represents a pair of electrons and $M^2$ represents hydrogen, the phosphorus group in a radical of the formula Ide may also be in tautomeric form as a group of the formula

The group $R_z$ may, in addition to hydroxy, also represent hydroxy that is present in salt form or reactive etherified or esterified hydroxy, as described above.

A removable group $M^2$ represents a radical etherifying an organic hydroxy group and is especially lower alkyl, such as methyl or ethyl, and also phenyl.

In a derivative of a compound of the formula XIV or XV, the hydroxy group is in reactive derivatised form, for example in the form of a reactive esterified hydroxy group or in the form of a metal oxy group, for example an alkali metal oxy group.

Protecting groups for functional groups which may be present in the starting materials are, for example, the protecting groups mentioned above.

The reaction is carried out in a manner known per se, for example as described above, and if in a starting material $=M^1$ represents a pair of electrons, the operation is carried out in the presence of an oxidising agent, for example one of those mentioned above.

The starting materials may be manufactured in a manner known per se, for example analogously to the processes described herein.

Compounds of the formula I in which $R^6$ represents lower alkyl that is substituted by a radical of the formula Id in which m represents 0 and $A^2$ has the meaning given above, or salts thereof, may be manufactured, for example, by reacting a compound of the formula I in which $R^6$ represents lower alkyl that is substituted by a group of the formula Idb in which E has the meaning given above, or a reactive derivative thereof, with a compound of the formula XII or XIII in which $R_z$ represents hydroxy which is optionally present in reactive form, $=M^1$ represents a pair of electrons or oxo, and $M^2$ represents hydrogen or a removable group, and $R^{15}$, $R^{16}$ and $R^{17}$ have the meanings given above, if necessary in the presence of an oxidising agent, wherein in the starting materials the remaining substituents $R^1$, $R^2$, $R^3$, $R^4$, $R^5$, $R^7$, $R^8$, $R^9$, $R^{10}$, $R^{11}$, $R^{12}$, $R^{13}$, $X^1$ and $X^2$ have the meanings given above and free functional groups, with the exception of the groups participating in the reaction, may be in protected form, and removing any protecting groups present in a resulting compound of the formula I and, if desired, carrying out additional process steps.

In a starting material having a hydroxy or amino group of the formula Idb, such a group may be in reactive derivatised form; a hydroxy group may be, for example, in the form of a reactive esterified hydroxy group or in the form of a metal oxy group, for example an alkali metal oxy group, and an amino group may be, for example, in phosphorus-substituted form (which can be formed, for example, by treatment with a phosphite).

If in a starting material of the formula XII or XIII $=M^1$ represents a pair of electrons and $M^2$ represents hydrogen, the compound may be in the tautomeric form of the formula XIIa or XIIIa, respectively.

The group $R_z$ may, in addition to hydroxy, also be in the form of hydroxy that is present in salt form, or in the form of reactive etherified or esterified hydroxy, as described above.

A removable group $M^2$ represents an organic radical etherifying a hydroxy group and is especially lower alkyl, such as methyl or ethyl, and also phenyl.

Protecting groups for functional groups which may be present in the starting materials are, for example, the protecting groups mentioned above.

The reaction is carried out in a manner known per se, for example as described above, and if in a starting material $=M^1$ represents a pair of electrons, the operation is carried out in the presence of an oxidising agent, for example one of those mentioned above.

The starting materials may be manufactured in a manner known per se, for example analogously to the processes described herein.

Compounds of the formula I in which one of the groups $R^9$ and $R^{11}$ represents a radical of the formula Ie in which $X^5$, $Y^3$, $X^6$ and $A^3$ have the meanings given above, and the other represents free hydroxy or mercapto, etherified hydroxy or mercapto other than a radical of the formula Ie, or free amino or substituted amino other than a radical of the formula Ie, or a group of the formula Ie, or salts thereof, may be manufactured, for example, by reacting a compound of the formula I in which one of the groups $R^9$ and $R^{11}$ represents hydroxy or mercapto and the other represents free hydroxy or mercapto, etherified hydroxy or mercapto other than a radical of the formula Ie, free amino or substituted amino other than a radical of the formula Ie, or a radical of the formula Ie, or a reactive acid derivative thereof, with a compound of the formula XVIII

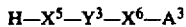 (XVIII), in which $X^5$, $Y^3$, $X^6$ and $A^3$ have the meanings given above, or with a reactive derivative thereof, wherein in the starting materials the remaining substituents $R^1$, $R^2$, $R^3$, $R^4$, $R^5$, $R^6$, $R^7$, $R^8$, $R^{10}$, $R^{12}$, $R^{13}$, $X^1$ and $X^2$ have the meanings given above and functional groups which may be present, with the exception of the groups participating in the reaction, may be in protected form, and removing any protecting groups present in a resulting compound of the formula I and, if desired, carrying out additional process steps.

The acid group in a starting material is preferably in reactive derivatised form, especially in one of the reactive, anhydridised, activated esterified or cyclically amidated forms described above, and also in salt form, for example in alkali metal salt form.

In a reactive derivative of a compound of the formula XVIII, a hydroxy group represented by the group of the formula $H-X^5-$ is in derivatised form, for example, as described above, in the form of a reactive esterified hydroxy group, or in salt form, for example in the form of a metal oxy group, such as an alkali metal oxy group, for example a sodium oxy or potassium oxy group, whilst a corresponding mercapto group is derivatised in analogous manner. A corresponding amino group is, for example, an amino group substituted by phosphorus as described above.

Protecting groups for functional groups which may be present in the starting materials are, for example, the protecting groups mentioned above.

The reaction is carried out in a manner known per se, for example as described above.

The starting materials are known or may be manufactured in a manner known per se.

Compounds of the formula I in which one of the groups $R^9$ and $R^{11}$ represents a radical of the formula Ie in which $Y^3$ represents unsubstituted or substituted alkylene which is interrupted by iminocarbonyl or oxycarbonyl, and in which $X^5$, $X^6$ and $A^3$ have the meanings given above, and the other represents free hydroxy or mercapto, etherified hydroxy or mercapto other than a radical of the formula Ie, free amino or substituted amino other than a radical of the formula Ie, or a group of the formula Ie, or salts thereof, may be manufactured, for example, by reacting a compound of the formula I in which one of the groups $R^9$ and $R^{11}$ represents a radical of the formula $-X^5-$ $-Y_a^3-R_x$ (Iea) with a compound of the formula $R_y-Y_b^3-X^6-A^3$ (XIX) in which one of the groups $R_x$ and $R_y$ represents hydroxy or amino of the formula $-NH(R^{14})$ that is free or present in reactive derivatised form, and the other represents carboxy that is free or present in reactive derivatised form, each of $Y_a^3$ and $Y_b^3$, independently of the other, represents unsubstituted or substituted alkylene and $X^5$, $X^6$ and $A^3$ have the meanings given above, wherein in the starting materials the remaining substituents $R^1$, $R^2$, $R^3$, $R^4$, $R^5$, $R^6$, $R^7$, $R^8$, $R^{10}$, $R^{12}$, $R^{13}$, $X^1$ and $X^2$ have the meanings given above, and functional groups which may be present, with the exception of groups participating in the reaction, may be in protected form, and removing any protecting groups present in a resulting compound of the formula I and, if desired, carrying out additional process steps.

A hydroxy group $R_x$ or $R_y$ may be in derivatised form, for example, as described above, in the form of a reactive esterified hydroxy group, also in the form of a metal oxy group, such as an alkali metal oxy group, for example a sodium oxy or potassium oxy group. A derivatised amino group $R_x$ or $R_y$ may be, for example, an amino group substituted by phosphorus as described above.

A carboxyl group $R_x$ or $R_y$ is preferably in reactive derivatised form, especially in one of the reactive, anhydridised, activated esterified or cyclically amidated forms described above, and also in salt form, for example in alkali metal salt form.

Protecting groups for functional groups which may be present in starting materials are, for example, the protecting groups mentioned above.

The reaction is carried out in a manner known per se, for example as described above.

The starting materials are known or may be manufactured in a manner known per se.

Compounds of the formula I in which one of the groups $R^9$ and $R^{11}$ represents a radical of the formula Ie in which $X^5$, $Y^3$, $X^6$ and $A^3$ have the meanings given above, and the other represents free hydroxy or mercapto, etherified hydroxy or mercapto other than a radical of the formula Ie, free amino or substituted amino other than a radical of the formula Ie, or a group of the formula Ie, or salts thereof, may be manufactured, for example, by reacting a compound of the formula I in which one of the groups $R^9$ and $R^{11}$ represents a radical of the formula $-X^5-Y^3-X^6-H$ (Ieb) in which $X^5$, $Y^3$ and $X^6$ have the meanings given above, and the other represents free hydroxy or mercapto, etherified hydroxy or mercapto other than a radical of the formula Ie, free amino or substituted amino other than a radical of the formula Ie, or a group of the formula Ie or Ieb, or a reactive derivative thereof, with a compound of the formula XII or XIII, in which $R_z$ represents hydroxy that is optionally present in reactive derivatised form, $=M^1$ represents a pair of electrons or oxo, and $M^2$ represents hydrogen or a removable group, and $R^{15}$, $R^{16}$ and $R^{17}$ have the meanings given above, if necessary in the presence of an oxidising agent, wherein in the starting materials the remaining substituents $R^1$, $R^2$, $R^3$, $R^4$, $R^5$, $R^6$, $R^7$, $R^8$, $R^{10}$, $R^{12}$, $R^{13}$, $X^1$ and $X^2$ have the meanings given above and functional groups which may be present, with the exception of the groups participating in the reaction, may be in protected form, and removing any protecting groups present in a resulting compound of the formula I and, if desired, carrying out additional process steps.

If $=M^1$ represents a pair of electrons and $M^2$ represents hydrogen, the compounds of the formulae XII and XIII may also be in the form of tautomers of the formulae XIIa and XIIIa, respectively.

The group $R_z$ may, in addition to hydroxy, also represent hydroxy that is present in salt form or reactive etherified or esterified hydroxy, as described above.

A removable group $M^2$ represents a radical etherifying an organic hydroxy group and is especially lower alkyl, such as methyl or ethyl, and also phenyl.

In a starting material having a group of the formula Ieb, the hydroxy or amino group of the formula $-X^6-H$ may be in reactive derivatised form. If the group of the formula $-X^6-H$ represents hydroxy, this may be, for example, in the form of a reactive esterified hydroxy group, such as one of the groups of this type mentioned above, or alternatively in the form of a metal oxy group, such as an alkali metal oxy group, for example a sodium oxy or potassium oxy group. A corresponding amino group may be, for example, in phosphorus-substituted form.

Protecting groups for functional groups which may be present in the starting materials are, for example, the protecting groups mentioned above.

The reaction is carried out in a manner known per se, for example as described above, and if in a starting material $=M^1$ represents a pair of electrons, the operation is carried out in the presence of an oxidising agent, for example one of those mentioned above.

The starting materials may be manufactured in a manner known per se, for example analogously to the processes described herein.

Compounds of the formula I in which one of the groups $R^9$ and $R^{11}$ represents a radical of the formula Ie in which $X^5$, $Y^3$, $X^6$ and $A^3$ have the meanings given above, and the other represents free hydroxy or mercapto, etherified hydroxy or mercapto other than a radical of the formula Ie, free amino or substituted amino other than a radical of the formula Ie, or a group of the formula Ie, or salts thereof, may be manufactured, for example, by reacting a compound of the formula I in which one of the groups $R^9$ and $R^{11}$ represents a radical of the formula

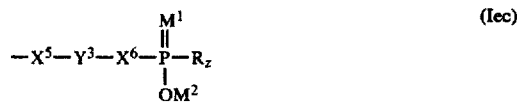

(Iec)

in which $R_z$ represents hydroxy which is optionally present in reactive derivatised form, $=M^1$ represents a pair of electrons or oxo, and $M^2$ represents hydrogen or a removable group, and $X^5$, $Y^3$ and $X^6$ have the meanings given above, and the other represents free hydroxy or mercapto, etherified hydroxy or mercapto other than a radical of the formula Ie, free amino or substituted amino other than a radical of the formula Ie, or a group of the formula Ie or Iec, with a compound of the formula XIV or XV, in which $R^{15}$, $R^{16}$ and $R^{17}$ have the meanings given above, or with a derivative thereof, if necessary in the presence of an oxidising agent, wherein in the starting materials the remaining substituents $R^1$, $R^2$, $R^3$, $R^4$, $R^5$, $R^6$, $R^7$, $R^8$, $R^{10}$, $R^{12}$, $R^{13}$, $X^1$ and $X^2$ have the meanings given above and free functional groups, with the exception of the groups participating in the reaction, may be in protected form, and removing any protecting groups present in a resulting compound of the formula I and, if desired, carrying out additional process steps.

If $=M^1$ represents a pair of electrons and $M^2$ represents hydrogen, the phosphorus group in a radical of the formula Iec may also be in tautomeric form as a group of the formula

The group $R_z$ may, in addition to hydroxy, also represent hydroxy that is present in salt form or reactive etherified or esterified hydroxy, as described above.

A removable group $M^2$ represents a radical etherifying an organic hydroxy group and is especially lower alkyl, such as methyl or ethyl, and also phenyl.

In a derivative of a compound of the formula XIV or XV the hydroxy group is in reactive derivatised form, for example in the form of a reactive esterified hydroxy group or in the form of a metal oxy group, for example an alkali metal oxy group.

Protecting groups for functional groups which may be present in the starting materials are, for example, the protecting groups mentioned above.

The reaction is carried out in a manner known per se, for example as described above, and if in a starting material $=M^1$ represents a pair of electrons, the operation is carried out in the presence of an oxidising agent, for example one of those mentioned above.

The starting materials may be manufactured in a manner known per se, for example analogously to the processes described herein.

The compounds of the formula I according to the invention in which $R^1$ represents hydrogen, $X^1$ represents —NH—, $R^2$ represents the radical of an organic carboxylic acid, the radical of the formula —$X^2$—$R^{13}$ represents hydroxy and $R^{12}$ represents hydrogen, and in which the pyranose ring has the configuration of glucopyranose, or salts thereof, may also be manufactured as follows: in a glucofuranose compound of the formula XX

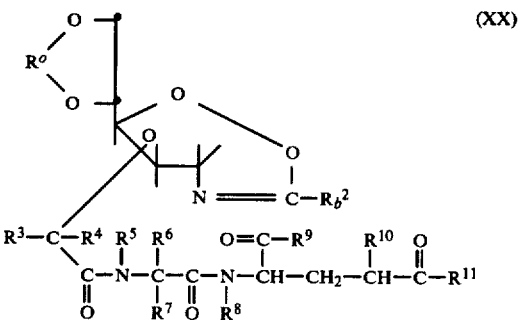

in which $R_b{}^2$ represents the descarbonyl radical of an acyl radical $R^2$ of an organic carboxylic acid, and $R^0$ represents unsubstituted or substituted methylene, and in which $R^3$, $R^4$, $R^5$, $R^6$, $R^7$, $R^8$, $R^9$, $R^{10}$ and $R^{11}$ have the meanings given above, and free functional groups which may be present may be in protected form, the oxazoline ring and the dioxolane ring are cleaved acidically, and any protecting groups present in a resulting compound of the formula I are removed and, if desired, additional process steps are carried out.

In a starting material of the formula XX $R_b{}^2$ is especially an aromatic radical, for example a phenyl radical.

A methylene radical $R^0$ is preferably substituted, for example by lower alkyl, such as methyl, by lower alkylene, such as 1,5-pentylene, or by phenyl that is unsubstituted or substituted, for example as described above, and represents, for example, lower alkylidene, such as isopropylidene, cycloalkylidene, such as cyclohexylidene, or benzylidene.

Protecting groups for functional groups which may be present are, for example, the protecting groups mentioned above.

The cleaving is effected in a manner known per se, for example by treatment with an acidic ion-exchanger, especially an ion-exchanger containing sulphonic acid groups, such as an acidic styrene resin having sulpho groups (for example Amberlite IR-120), or an acidic polystyrenesulphonic acid resin (for example Dowex 50), or with a strong inorganic or organic acid, such as a mineral acid, for example hydrochloric acid, hydrobromic acid or sulphuric acid, or an organic sulphonic acid, such as an aliphatic sulphonic acid, for example methanesulphonic acid, or a benzenesulphonic acid that is unsubstituted or substituted in the aromatic ring, such as p-toluenesulphonic acid, or a strong organic carboxylic acid, such as a halo-substituted lower alkanecarboxylic acid, for example trifluoroacetic acid. The operation is carried out in the presence of water and there are thus obtained compounds of the formula I in which $X^1$ and $X^2$ represent a group of the formula —O— and $R^1$, $R^{12}$ and $R^{13}$ represent hydrogen.

The starting materials may be manufactured according to processes known per se, inter alia analogously to the processes described herein.

In a resulting compound of the formula I, if desired, one or more of the following additional process steps is (are) carried out.

In a resulting compound of the formula I in which one or more functional groups are protected, these, for example protected carboxyl, amino, hydroxy and/or mercapto groups, can be freed, in a manner known per se, by means of solvolysis, especially hydrolysis, alcoholysis or acidolysis, or by means of reduction, especially hydrogenolysis or chemical reduction, optionally stepwise or simultaneously.

Thus, tert.-lower alkoxycarbonyl, or lower alkoxycarbonyl substituted in the 2-position by an organic silyl group or in the 1-position by lower alkoxy or lower alkylthio, or optionally substituted diphenylmethoxycarbonyl can be converted into free carboxyl, for example, by treatment with a suitable acid, such as formic acid or trifluoroacetic acid, optionally with the addition of a nucleophilic compound, such as phenol or anisole. Optionally substituted benzyloxycarbonyl can be freed, for example, by means of hydrogenolysis, i.e. by treatment with hydrogen in the presence of a metallic hydrogenation catalyst, such as a palladium catalyst. Furthermore, suitably substituted benzyloxycarbonyl, such as 4-nitrobenzyloxycarbonyl, can be converted into free carboxyl also by chemical reduction, for example by treatment with an alkali metal dithionite, for example sodium dithionite, or with a reducing metal, for example zinc, or metal salt, such as a chromium(II) salt, for example chromium(II) chloride, usually in the presence of a hydrogen-yielding agent which, together with the metal, is capable of producing nascent hydrogen, such as an acid, especially a suitable carboxylic acid, such as a lower alkanecarboxylic acid optionally substituted, for example by hydroxy, for example acetic acid, formic acid, glycolic acid, diphenylglycolic acid, lactic acid, mandelic acid, 4-chloromandelic acid or tartaric acid, or an alcohol or thiol, water preferably being added. By treatment with a reducing metal or metal salt it is also possible, as described above, to convert 2-halo-lower alkoxycarbonyl, (optionally after converting a 2-bromo-lower alkoxycarbonyl group into a corresponding 2-iodo-lower alkoxycarbonyl group), or aroylmethoxycarbonyl into free carboxyl, it being possible to cleave aroylmethoxycarbonyl likewise by treatment with a nucleophilic, preferably salt-forming, reagent, such as sodium thiophenolate or sodium iodide. Substituted 2-silylethoxycarbonyl can also be converted into free carboxyl by treatment with a salt of hydrofluoric acid which yields the fluoride anion, such as an alkali metal fluoride, for example sodium or potassium fluoride, in the presence of a macrocyclic polyether ("Crown ether"), or with a fluoride of an organic quaternary base, such as tetralower alkylammonium fluoride or tri-lower alkyl-arylammonium fluoride, for example tetraethylammonium fluoride or tetrabutylammonium fluoride, in the presence of an aprotic polar solvent, such as dimethyl sulphoxide or N,N-dimethylacetamide. A carboxyl group esterified by an organic silyl group, such as tri-lower alkylsilyl, for example trimethylsilyl, can be freed in the usual manner by solvolysis, for example by treatment with water, an alcohol or an acid.

A protected amino group is freed in a manner known per se and, depending on the type of protecting group, in various ways, preferably by means of solvolysis or reduction. 2-halo-lower alkoxycarbonylamino, (optionally after converting a 2-bromo-lower alkoxycarbonylamino group into a 2-iodo-lower alkoxycarbonylamino group), aroylmethoxycarbonylamino or 4-nitrobenzyloxycarbonylamino can be cleaved, for example by treatment with a suitable chemical reducing agent, such as zinc in the presence of a suitable carboxylic acid, such as aqueous acetic acid. Aroylmethoxycarbonylamino can also be cleaved by treatment with a nucleophilic, preferably salt-forming, reagent, such as sodium thiophenolate, and 4-nitrobenzyloxycarbonylamino also by treatment with an alkali metal dithionite, for example sodium dithionite. Optionally substituted diphenylmethoxycarbonylamino, tert.-lower alkoxycarbonylamino or 2-trisubstituted silylethoxycarbonylamino can be freed by treatment with a suitable acid, for example formic or trifluoroacetic acid, optionally substituted benzyloxycarbonylamino, for example by means of hydrogenolysis, i.e. by treatment with hydrogen in the presence of a suitable hydrogenation catalyst, such as a palladium catalyst, optionally substituted triarylmethylamino or formylamino, for example by treatment with an acid, such as a mineral acid, for example hydrochloric acid, or an organic acid, for example formic, acetic or trifluoroacetic acid, optionally in the presence of water, and an amino group protected by an organic silyl group, for example by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate, of thiourea, and by subsequent solvolysis, such as alcoholysis or hydrolysis, of the resulting condensation product. An amino group protected by 2-substituted silylethoxycarbonyl can also be converted into the free amino group by treatment with a salt of hydrofluoric acid which yields fluoride anions, as stated above in connection with the freeing of a correspondingly protected carboxyl group.

Amino protected in the form of an azido group is converted into free amino, for example by reduction, for example by catalytic hydrogenation with hydrogen in the presence of a hydrogenation catalyst, such as platinum oxide, palladium or Raney nickel, or alternatively by treatment with zinc in the presence of an acid, such as acetic acid. Catalytic hydrogenation is preferably carried out in an inert solvent, such as a halogenated hydrocarbon, for example methylene chloride, or alternatively in water or a mixture of water and an organic solvent, such as an alcohol or dioxan, at approximately from 20° C. to 25° C., or alternatively while cooling or heating.

A hydroxy or mercapto group protected by a suitable acyl group, an organic silyl group or by optionally substituted 1-phenyl-lower alkyl is freed analogously to a correspondingly protected amino group. A hydroxy or mercapto group protected by 2,2-dichloroacetyl is freed, for example, by basic hydrolysis, a hydroxy or mercapto group etherified by tert.-lower alkyl or by a 2-oxa- or 2-thiaaliphatic or a 2-oxa- or 2-thia cycloaliphatic hydrocarbon radical is freed by acidolysis, for example by treatment with a mineral acid or a strong carboxylic acid, for example trifluoroacetic acid. Two hydroxy groups that are together protected by means of a preferably substituted methylene group, such as by lower alkylidene, for example isopropylidene, cycloalkylidene, for example cyclohexylidene, or benzylidene, can be freed by acid solvolysis, especially in the presence of a mineral acid or a strong organic acid.

When several protected functional groups are present, the protecting groups are preferably so chosen that more than one such group can be removed simultaneously, for example by acidolysis, such as by treatment with trifluoroacetic acid or formic acid, or by reduction, such as by treatment with zinc and acetic acid, or with hydrogen and a hydrogenation catalyst, such as a palladium-carbon catalyst.

Compounds of the formula I obtainable according to the invention may, if desired, be converted into different compounds of the formula I. Thus, for example, acid groups, such as carboxyl groups, may be esterified, hydroxy and mercapto groups may, for example, be etherified or esterified, or amino groups may, for example, be acylated. These additional reactions may be carried out in a manner known per se, for example analogously to the processes described herein.

Salts of compounds of the formula I can be manufactured in a manner known per se. Thus, salts of compounds of the formula I may be formed, for example, by treatment with metal compounds, such as alkali metal salts of suitable organic carboxylic acids, for example the sodium salt of α-ethylcaproic acid, or with inorganic alkali metal or alkaline earth metal compounds, such as corresponding hydroxides, carbonates and bicarbonates, such as sodium or potassium hydroxide, carbonate or bicarbonate, or corresponding calcium compounds, or with ammonia or suitable organic amines, there being used preferably stoichiometric quantities or a slight excess of the salt-forming agent. Acid addition salts of compounds of the formula I containing salt-forming basic groups are obtained in customary manner, for example by treatment with an acid or a suitable anion-exchange reagent. Internal salts of compounds of the formula I that contain acid and basic salt-forming groups may be formed, for example, by neutralisation of salts, such as acid addition salts, to the isoelectric point, for example with weak bases, or by treatment with liquid ion exchangers.

Salts may be converted into the free compounds in customary manner; metal and ammonium salts can be converted, for example, by treatment with suitable acids, and acid addition salts, for example, by treatment with a suitable basic agent.

Mixtures of isomers can be separated in a manner known per se into the individual isomers, for example by fractional crystallisation, chromatography etc., and racemates may be separated, for example with the formation of derivatives with optically active compounds and separation of the diastereoisomeric mixtures obtainable in this manner into the optically active antipodes.

The processes described above, including the processes for removing protecting groups and the additional process steps, are carried out in a manner known per se, for example in the presence or absence of solvents or diluents, if necessary in the presence of condensation agents or catalysts, at reduced or elevated temperature, for example in a temperature range of from approximately −20° C. to approximately 150° C., in a closed vessel and/or in an inert gas atmosphere, for example a nitrogen atmosphere.

Taking into consideration all the substituents present in the molecule, if necessary, for example if readily hydrolysable radicals are present, especially mild reaction conditions should be used, such as short reaction times, the use of mild acid or basic agents in low concentrations, stoichiometric quantity ratios and the selection of suitable catalysts, solvents, temperature and/or pressure conditions.

The invention relates also to those forms of the process in which a compound obtainable as intermediate at any stage of the process is used as starting material and the remaining process steps are carried out, or the process is discontinued at any stage, or a starting material is formed under the reaction conditions or is used in the form of a reactive derivative or salt. Preferably the starting materials used are those which according to the process result in the compounds described above as being especially valuable.

The invention relates likewise to novel intermediates, especially novel compounds of the formula V, in which $R^5$, $R^6$, $R^7$, $R^8$, $R^9$, $R^{10}$ and $R^{11}$ have the meanings given above, or salts thereof, and also to the compounds of the formula V in which $R^5$, $R^6$, $R^7$, $R^8$, $R^9$, $R^{10}$ and $R^{11}$ have the meanings given above, or pharmaceutically acceptable salts thereof for pharmacological use, especially as immunomodulating, for example immunostimulating, agents, and pharmaceutical preparations containing compounds of the formula V or pharmaceutically acceptable salts thereof. It has become apparent that intermediates also, especially those of the formula V, have immunomodulating action, and may therefore be used analogously to the compounds of the formula I.

The invention relates also to pharmaceutical preparations which contain a pharmacologically active amount of the active substance, optionally together with pharmaceutically acceptable carriers which are suitable for enteral, for example oral, or parenteral administration, and may be inorganic or organic and solid or liquid. Thus, tablets or gelatin capsules are used which contain the active substance together with diluents, for example lactose, dextrose, sucrose, mannitol, sorbitol, cellulose and/or glycerine, and/or lubricants, for example silica, talc, stearic acid or salts thereof, such as magnesium or calcium stearate, and/or polyethylene glycol. Tablets may also contain binders, for example magnesium aluminium silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescing mixtures, or absorbents, colouring substances, flavourings and sweeteners. The pharmacologically active compounds of the present invention can also be used in the form of parenterally administrable preparations or infusion solutions. Such solutions are preferably isotonic aqueous solutions or suspensions, it being possible to manufacture these before use, for example in the case of lyophilised preparations which contain the active substance alone or together with a carrier, for example mannitol. The pharmaceutical preparations can be sterilised and/or contain adjuncts, for example preservatives, stabilisers, wetting agents and/or emulsifiers, solubilisers, salts for regulating the osmotic pressure and/or buffers. The present pharmaceutical preparations which may, if desired, contain further pharmacologically active substances, such as antibiotics, are manufactured in a manner known per se, for example by means of conventional mixing, granulating, confectioning, dissolving or lyophilising processes, and contain from approximately 1% to 100%, especially from approximately 5% to approximately 50%, and, in the case of lyophilisates, up to 100%, of the active substance(s).

The dosage may depend on various factors, such as the manner of administration, species, age and/or individual condition. Thus, the daily doses to be administered in the case of oral administration to warm-blooded animals of approximately 70 kg are preferably between approximately 0.001 and 0.1 g.

The following examples illustrate the invention but do not restrict it in any way. The $R_f$ values are determined on silica gel thin layer plates by Merck. The relationship of eluants to one another in the eluant mixtures used is given in proportions by volume (v/v) and temperatures are given in degrees Centigrade. Although it is not stated in each individual case in the following, the phosphoryl compounds are usually obtained in the form of or in admixture with their salts, for example sodium salts, such as mono- or bis-sodium salts.

EXAMPLE 1

1.5 mmol of the N-hydroxysuccinimide ester of N-acetyl-6-O-succinoylnormuramyl-L-alanyl-D-isoglutamine-γ-diphenylmethyl ester, dissolved in 5 ml of dimethylacetamide, are added dropwise at room temperature to a solution of 1 mmol of 2-(1,2-dipalmitoyl-sn-glycero-3-hydroxyphosphoryloxy)-ethylamine and 2 mmol of triethylamine in 20 ml of a mixture of chloroform:methanol:water = 65:25:4. After stirring for 20 hours at room temperature, the solution is concentrated to approximately 15 ml under reduced pressure; an emulsion is formed. This emulsion is diluted with 200 ml of water and freeze-dried. The residue is suspended in 25 ml of water and dialysed for 24 hours against 0.1 molar sodium phosphate buffer, pH 7, and then for 2 days against water. The inner dialysate, which contains the desired product (mixture with 40–55% of the sodium salt), is freeze-dried. In order to remove the diphenylmethyl radical, the freeze-dried residue is dissolved in 50 ml of a mixture (1:1) of 1,2-dimethoxyethane and methanol and hydrogenated over Pd/BaSO$_4$ (10% strength). The catalyst is filtered off and the solvent is distilled off under reduced pressure.

The N-acetyl-6-O-{[N-2-(1,2-dipalmitoyl-sn-glycero-3-hydroxyphosphoryloxy)-ethyl]-succinamoyl}-normuramyl-L-alanyl-D-isoglutamine, which is present partly in sodium salt form, is purified by chromatography over a Sephadex LH-20 column, elution mixture chloroform:methanol:acetic acid:water = 25:15:4:2, R$_f$ = 0.36 (chloroform:methanol:water = 65:25:4), R$_f$ = 0.66 (chloroform:methanol:acetic acid:water = 25:15:4:2).

The novel compound is characterised analytically by determining quantitatively the building blocks, viz. N-acetylmuramic acid, palmitic acid, phosphate, L-alanine and D-glutamic acid; N-acetylmuramic acid is determined spectrophotometrically by means of the Morgan-Elson reaction according to the modification of J. M. Ghuysen et al. [in "Methods in Enzymology" 8, 629 (1966)].

Phosphate is determined quantitatively according to Lowry et al. [J. Biol. Chem. 207, 1 (1954)].

Palmitic acid and the amino acids are determined quantitatively in a total hydrolysate (6 N HCl, 24 hours 110° C.) by gas chromatography or by means of an amino acid analyser using pentadecanoic acid or norleucine, respectively, as internal standards.

The molar ratios found, based on phosphate, are as follows:

PO$_4'''$: N-acetylmuramic acid:alanine:glutamic acid:palmitic acid = 1:0.90:0.93:0.95:2.16.

The starting materials can be obtained as follows:

2 mmol of N-acetyl-6-O-succinoylnormuramyl-L-alanyl-D-isoglutamine-γ-diphenylmethyl ester, 2.1 mmol of N-hydroxysuccinimide and 2.1 mmol of dicyclohexyl carbodiimide are dissolved in 6.6 ml of dimethylacetamide and stirred for 18 hours at 20° C. The precipitated dicyclohexylurea is separated off and the solution, which contains the N-hydroxysuccinimide ester of N-acetyl-6-O-succinoylnormuramyl-L-alanyl-D-isoglutamine-γ-diphenylmethyl ester, is used directly for the condensation with the phospholipid.

2-(1,2-dipalmitoyl-sn-glycero-3-hydroxyphosphoryloxy)ethylamine is a commercially available synthetic preparation.

5.1 g (7.8 mmol) of N-acetylnormuramyl-L-alanyl-D-isoglutamine-γ-diphenylmethyl ester are dissolved in 40 ml of absolute pyridine and 2.34 g (23.4 mmol) of succinic acid anhydride, dissolved in 40 ml of absolute ethyl acetate, are added dropwise at −5° in the course of 20 minutes. After standing for 2 days at 0°, the mixture is acidified to pH = 4 with 4 N acetic acid and, after stirring for one hour, is concentrated by evaporation. The residue is dissolved in 100 ml of acetonitrile:water = 1:4, poured over 100 g of silica gel UPC$_{12}$ (ANTEC) and then first the succinic acid is eluted with acetonitrile:water = 1:1 and then the main portion of the product with acetonitrile:water = 3:1. 3.1 g of N-acetyl-6-O-succinoylnormuramyl-L-alanyl-D-isoglutamine-γ-diphenylmethyl ester are obtained in the form of an amorphous powder, $[\alpha]_D^{20} = +16°$ (c = 0.243; methanol), R$_f$ = 0.43 (n-butanol:acetic acid:water = 75:7.5:21), R$_f$ = 0.70 (ethyl acetate:n-butanol:pyridine:acetic acid:water = 42:21:21:6:10).

11.6 g (60 mmol) of diphenyldiazomethane are added to a solution of 22.8 g (40 mmol) of N-acetylnormuramyl-L-alanyl-D-isoglutamine in 500 ml of a 1:1 mixture of 1,2-dimethoxyethane and methanol and the solution is stirred for 16 hours at room temperature. The red suspension is concentrated by evaporation under reduced pressure at 20° and the residue is triturated several times with diethyl ether until an almost colourless product is obtained. This product is dissolved in 100 ml of methanol and caused to crystallise by adding in portions a 2:1 mixture of diethyl ether/petroleum ether. After stirring for several hours at room temperature, the crystal mass is filtered off in an ice bath and dried under reduced pressure. In this manner the N-acetylnormuramyl-L-alanyl-D-isoglutamine diphenylmethyl ester is obtained in the form of cubic crystals, m.p. 170° (with decomposition), $[\alpha]_D^{20} \pm 14 \pm 1°$ (c = 1.5; methanol), R$_f$ = 0.40 (chloroform:methanol:water = 70:30:5), R$_f$ = 0.66 (ethyl acetate:n-butanol:pyridine:glacial acetic acid:water = 42:21:21:6:10).

EXAMPLE 2

Analogously to Example 1, the following compounds are obtained which are present in sodium salt form or in admixture therewith:

N-Acetyl-6-O-{N-[2-(1,2-dipalmitoyl-sn-glycero-3-hydroxyphosphoryloxy)-ethyl]-succinamoyl}-muramyl-L-α-aminobutyryl-D-isoglutamine, N-Acetyl-6-O- N-[2-(tetradecyloxyhydroxyphosphoryloxy)ethyl]-succinamoyl}-muramyl-L-α-aminobutyryl-D-isoglutamine, N-Propionyl-6-O-{N-[2-(1,2-dipalmitoyl-sn-glycero-3-hydroxyphosphoryloxy)-ethyl]-succinamoyl}-normuramyl-L-alanyl-D-isoglutamine, N-Propionyl-6-O-{N-[2-(tetradecyloxyhydroxyphosphoryloxy)ethyl]-succinamoyl}-normuramyl-L-alanyl-D-isoglutamine, N-Acetyl-6-O-{N-[2-(1,2-dipalmitoyl-sn-glycero-3-hydroxyphosphoryloxy)-ethyl]-succinamoyl}-muramyl-L-valyl-D-isoglutamine, N-Acetyl-6-O-{N-[2-(tetradecyloxyhydroxyphosphoryloxy)ethyl]-succinamoyl}-muramyl-L-valyl-D-isoglutamine, N-Acetyl-6-O-{N-[2-(1,2-dipalmitoyl-sn-glycero-3-hydroxyphosphoryloxy)-ethyl]-succinamoyl}-normuranyl-L-alanyl-D-glutamylglycineamide, N-Acetyl-6-O-{N-[2-(tetradecyloxyhydroxyphosphoryloxy)ethyl]-succinamoyl}-normuramyl-L-alanyl-D-glutamylglycineamide, N-Benzoyl-6-O-{N-[1,2-dipalmitoyl-sn-glycero-3-hydroxyphosphoryloxy)-ethyl]succinamoyl}-muramyl-L-alanyl-D-isoglutamine, N-Benzoyl-6-O-{N-[2-(tetradecyloxyhydroxyphosphoryloxy)ethyl]-succinamoyl}-muramyl-L-alanyl-D-isoglutamine, N-Benzoyl-6-O-{N-[2-(1,2-dipalmitoyl-sn-glycero-3-hydroxyphosphoryloxy)-ethyl]-succinamoyl}-normuramyl-L-α-aminobutyryl-D-isoglutamine, N-Benzoyl-6-O-{N-[2-(tetradecyloxyhydroxyphosphoryloxy)ethyl]-succinamoyl}-normuramyl-L-α-aminobutyryl-D-isoglutamine, N-Acetyl-6-O-{N-[2-(1,2-dipalmitoyl-sn-glycero-3-hydroxyphosphoryloxy)-ethyl]-succinamoyl}-muramyl-L-alanyl-D-(γ-carboxy)-isoglutamine, N-Acetyl-6-O-{N-[2-(tetradecyloxyhydroxyphosphoryloxy)ethyl]-succinamoyl}-muramyl-L-alanyl-D-(γ-carboxy)isoglutamine, 2-Acetylamino-2-desoxy-6-O-{N-[2-(1,2-dipalmitoyl-sn-glycero-3-hydroxyphosphoryloxy)-ethyl]-succinamoyl}-D-mannopyranosyl-(3-O)-D-propionyl-L-alanyl-D-isoglutamine, N-Acetyl-6-O-{N-[2-(1,2-dipalmitoyl-sn-glycero-3-hydroxyphosphoryloxy)-ethyl]-succinamoyl}-muramyl-L-α-aminobutyryl-D-isoglutamine-γ-n-butyl ester, 2-Acetylamino-2-desoxy-6-O-{N-[2-(tetradecyloxyhydroxyphosphoryloxy)-ethyl]-succinamoyl}-D-mannopyranosyl(3-O)-D-propionyl-L-alanyl-D-isoglutamine, 2-Acetylamino-2-desoxy-6-O-{N-[2-(1,2-dipalmitoyl-sn-glycero-3-hydroxyphosphoryloxy)-ethyl]-succinamoyl}-D-galactopyranosyl-(3-O)-D-propionyl-L-alanyl-D-isoglutamine, 2-Acetylamino-2-desoxy-6-O-{N-[2-(tetradecyloxyhydroxyphosphoryloxy)-ethyl]-succinamoyl}-D-galactopyranosyl(3-O)-D-propionyl-L-alanyl-D-isoglutamine, N-Acetyl-6-O{N-[2-(1,2-dipalmitoyl-sn-glycero-3-hydroxyphosphoryloxy)-ethyl]-succinamoyl}-muramyl-L-prolyl-D-isoglutamine, N-Acetyl-6-O-{N-[2-(tetradecyloxyhydroxyphosphoryloxy)ethyl]-succinamoyl}-muramyl-L-prolyl-D-isoglutamine, N-Acetyl-6-O-{N-[2-(1,2-dipalmitoyl-sn-glycero-3-hydroxyphosphoryloxy)-ethyl]-succinamoyl}-normuramyl-L-α-aminobutyryl-D-isoglutamine, N-Acetyl-6-O-{N-[2-(tetradecyloxyhydroxyphosphoryloxy)ethyl]-succinamoyl}-normuramyl-L-α-aminobutyryl-D-isoglutamine, N-Acetyl-6-O-{N-[2-(1,2-dipalmitolyl-sn-glycero-3-hydroxyphosphoryloxy)-ethyl]-succinamoyl}-muramyl-D-α-aminobutyryl-D-isoglutamine, N-Acetyl-6-O-{N-[2-(tetradecyloxyhydroxyphosphoryloxy)ethyl]-succinamoyl}-muramyl-D-α-aminobutyryl-D-isoglutamine, N-Acetyl-6-O-{N-[2-(1,2-dipalmitoyl-sn-glycero-3-hydroxyphosphoryloxy)-ethyl]-succinamoyl}-muramyl-α-aminoisobutyryl-D-isoglutamine, N-Acetyl-6-O-{N-[2-(tetradecyloxyhydroxyphosphoryloxy)ethyl]-succinamoyl}-muramyl-α-aminoisobutyryl-D-isoglutamine.

EXAMPLE 3

In a manner analogous to that described in Example 1, N-acetylnormuramyl-L-O-{N-[2-(tetradecyloxyhydroxyphosphoryloxy)-ethyl]-succinamoyl}-seryl-D-isoglutamine is obtained partly in sodium salt form starting from 2-(tetradecyloxyhydroxyphosphoryloxy)-ethylamine and the N-hydroxysuccinimide ester of N-acetyl-normuramyl-L-O-(succinoyl)-seryl-D-isoglutamine-γ-diphenylmethyl ester.

EXAMPLE 4

A solution of 1.5 mmol of N-acetyl-6-O-(N-stearoylglycyl)-normuramyl-L-alanyl-D-isoglutamine-N-hydroxysuccinimide ester in 5 ml of 1,2-dimethoxyethane is added dropwise at room temperature to a solution of 1 mmol of 2-[{(3'R)-hydroxy-(2'S)-palmitoylaminooctadecyloxy}-hydroxyphosphoryloxy]-ethylamine and 2 mmol of triethylamine in 200 ml of a mixture of chloroform:methanol:water=65:25:4. After stirring for 20 hours at room temperature, the solution is concentrated under reduced pressure to approximately 15 ml; an emulsion is formed. This emulsion is diluted with 200 ml of water and freeze-dried. The residue is suspended in 50 ml of water and dialysed for 24 hours against 0.1 M sodium phosphate buffer, pH=7, and then for 3 days against water. The inner dialysate, which contains N-acetyl-6-O-(N-stearoylglycyl)-normuramyl-L-alanyl-D-isoglutamine-2-[{(3'R)-hydroxy-(2'S)-palmitoylaminooctadecyloxy}-hydroxyphosphoryloxy]-ethylamide in the form of or in admixture with its sodium salt, is freeze-dried and purified by chromatography over a Sephadex LH-20 column. Elution mixture:- chloroform:methanol:water=65:25:4).

The novel compound is characterised analytically by determining the building blocks (stearic acid, palmitic acid, glycine, alanine, glutamic acid and phosphate) in a manner analogous to that described in Example 1.

The molar ratios found, based on phosphate, are as follows: $PO_4'''$:glycine:alanine:glutamic acid:palmitic acid:stearic acid = 1:0.89:0.92:0.95:1.09:0.98.

2-[{(3'R)-hydroxy-(2'S)-palmitoylaminooctadecyloxy}hydroxyphosphoryloxy]-ethylamine, which is used as starting material, is a commercially available synthetic preparation.

N-acetyl-6-O-(N-stearoylglycyl)-normuramyl-L-alanyl-D-isoglutamine-N-hydroxysuccinimide ester, which is used as starting material, can be manufactured, for example, as follows:

2 mmol of N-acetyl-6-O-(N-stearoylglycyl)-normuramyl-L-alanyl-D-isoglutamine, 2.1 mmol of N-hydroxysuccinimide and 2.1 mmol of dicyclohexyl carbodiimide are dissolved in 6.6 ml of 1,2-dimethoxyethane and stirred for 18 hours at 20° C. The precipitated dicyclohexylurea is separated off and the solution is used directly for the condensation with the phospholipid.

The starting material is manufactured as follows:

0.60 g (0.7 mmol) of N-acetyl-6-O-(N-stearoylglycyl)normuramyl-L-alanyl-D-isoglutamine-γ-tert.-butyl ester is dissolved at 0° in 7 ml of 95% trifluoroacetic acid and left to stand for 20 minutes at that temperature. The clear solution is concentrated by evaporation and the residue is dried under a high vacuum over sodaasbestos (Merck). The residue is dissolved in 15 ml of a mixture of tert.-butanol:water=9:1, filtered over 40 ml of purified strongly acidic ion exchanger (H-form) and then washed with 80 ml of the above mixture. The filtrate is concentrated to approximately 20 ml, filtered through a millipore filter (0.45µ) and lyophilised. 0.265 g of N-acetyl-6-O-(N-stearoylglycyl)normuramyl-L-alanyl-D-isoglutamine is obtained in the form of a colourless powder, $[\alpha]_D^{20} = +5\pm1°$ (c=0.40; methanol), $R_f=0.26$ (chloroform:methanol:water=70:30:5), $R_f=0.40$ (n-butanol:acetic acid:water=75:75:21).

The starting material is obtained as follows:

0.90 g (1.01 mmol) of N-acetyl-1α-O-benzyl-6-O-(N-stearoylglycyl)-normuramyl-L-alanyl-D-isoglutamine-γ-tert.-butyl ester, dissolved in 40 ml of 1,2-dimethoxyethane:water=20:1 is treated for 39 hours with hydrogen in the presence of 1.8 g of palladium-on-carbon (10% strength). The catalyst is filtered off, the filtrate is concentrated by evaporation and the residue is extracted four times with 20 ml of water each time after being taken up in a mixture of 80 ml of chloroform:ethyl acetate=1:5. After drying over sodium sulphate and concentrating by evaporation, 0.65 g of N-acetyl-6-O-(N-stearoylglycyl)normuramyl-L-alanyl-D-isoglutamine-γ-tert.-butyl ester remains in the form of a colourless foam. $R_f=0.62$ (chloroform:methanol:water=70:30:5), $R_f=0.52$ (n-butanol:acetic acid:water=75:7.5:21).

The starting material is obtained as follows:

A suspension of 0.70 g (1 mmol) of N-acetyl-1α-O-benzyl-6-O-glycylnormuramyl-L-alanyl-D-isoglutamine-γ-tert.-butyl ester hydrochloride, 0.446 g (1.15 mmol) of stearic acid p-nitrophenyl ester and 0.111 g (1 mmol) of N-methylmorpholine in 2 ml of dimethylformamide is stirred for 16 hours at room temperature, then concentrated to dryness by evaporation under reduced pressure. The residue is dissolved in chloroform and washed several times at a low temperature with a 1 N citric acid solution, then with water. The dried organic phase is concentrated by evaporation and purified over silica gel in the system chloroform/isopropanol=7:3. The N-acetyl-1α-O-benzyl-6-O-(N-stearoylglycyl)-normuramyl-L-alanyl-D-isoglutamine-γ-tert.-butyl ester is obtained in the form of an amorphous, strongly hygroscopic powder, $R_f=0.86$ (chloroform:methanol:water=70:30:5), $R_f=0.11$ (chloroform:isopropanol:acetic acid=70:8:2).

The starting material used is obtained as follows:

After the addition of 4.8 g of a palladium-on-carbon catalyst (10% strength), a solution of 16.8 g (20 mmol) of N-acetyl-1α-O-benzyl-6-O-(N-benzyloxycarbonylglycyl)normuramyl-L-alanyl-D-isoglutamine-tert.-butyl ester in 200 ml of a 20:1 mixture of 1,2-dimethoxyethane and water is treated with hydrogen. The pH value of the solution is maintained at 3 during the hydrogenation by the addition of 2 N aqueous hydrochloric acid by means of pH-Stat. The suspension is filtered, the filtrate is concentrated by evaporation under reduced pressure at room temperature, and the white residue is purified by chromatography over 400 g of silica gel (Merck AG, 0.06-0.2 mm) in the system chloroform/isopropanol=7:3. Preliminary washing is carried out with 2 fractions to every 1000 ml of the solvent mixture and elution is then carried out with 190 fractions to every 10 ml, followed by 4 fractions to every 800 ml; the pure product is obtained in these last 4 fractions. The residue from these is dissolved in a 10:1 mixture of 1,2-dimethoxyethane and water; the pH value of the solution is adjusted to 4.5 by the addition of 2 N hydrochloric acid while cooling and the solution is concentrated by evaporation under reduced pressure at a low temperature. The residue is dried over soda-asbestos (Merck AG) and yields N-acetyl-1α-O-benzyl-6-O-glycylnormuramyl-L-alanyl-D-isoglutamine-tert.-butyl ester hydrochloride in the form of a white foam, $R_f=0.47$ (chloroform:methanol:water=70:30:5), $R_f=0.10$ (chloroform:isopropanol=7:3).

The starting material is manufactured as follows:

A solution of 13.74 g (22 mmol) of N-acetyl-1α-O-benzylnormuramyl-L-alanyl-D-isoglutamine-tert.-butyl ester, 4.2 g (20 mmol) of N-benzyloxycarbonylglycine, 5.4 g (40 mmol) 1-hydroxybenztriazole and 2.44 g (20 mmol) of 4-dimethylaminopyridine in 100 ml of dimethylformamide is cooled to 0° and 5.0 g (24 mmol) of dicyclohexyl carbodiimide are added. After stirring for 24 hours at room temperature, the suspension is filtered and the filtrate is concentrated by evaporation under reduced pressure. The residue is taken up in 800 ml of ethyl acetate and washed at a low temperature three times with 100 ml of water each time and three times with 100 ml of 2 N aqueous citric acid solution each time. The organic phase is washed neutral with water and dried over sodium sulphate. On concentrating to a volume of approximately 100 ml, crystallisation begins. After stirring for several hours while cooling in an ice bath, the crystal mass is filtered off, washed and recrystallised from ethyl acetate. In this manner the N-acetyl-1α-O-benzyl-6-O-(N-benzyloxycarbonylglycyl)-normuramyl-L-alanyl-D-isoglutamine-tert.-butyl ester is obtained in the form of colourless needles, m.p. 155°-160°; $[\alpha]_D^{20} = +60\pm1°$ (c=1.2; dimethylformamide), $R_f=0.86$ (chloroform:methanol:water=70:30:5), $R_f=0.93$ (n-butanol:glacial acetic acid:water=75:7.5:21).

The above compound can also be obtained using the symmetrical anhydride of N-benzyloxycarbonylglycine in the presence of pyridine.

The above-mentioned protected N-acetyl-6-O-glycylnormuramyl-L-alanyl-D-isoglutamine can be manufactured with other protecting groups as follows:

6.8 g (7.2 mmol) of N-acetyl-6-O-[{2-(p-biphenylyl)isopropoxycarbonyl}-glycyl]-normuramyl-L-alanyl-D-isoglutamine-γ-diphenylmethyl ester, dissolved in 100 ml of 90% trifluoroethanol, are cleaved at room temperature with 0.1 N HCl in 90% trifluoroethanol at pH=0.5 (pH-Stat) in the course of one hour. The solvent is evaporated, the residue, after being dried, is triturated several times with 1,2-dimethoxyethane and the supernatant liquid is decanted off. 4.7 g (88% strength) of amorphous N-acetyl-6-O-glycylnormuramyl-L-alanyl-D-isoglutamine-γ-diphenylmethyl ester hydrochloride are obtained, $[\alpha]_D^{20} = +17°$ (c=0.396; methanol), $R_f=0.17$ (isopropanol:water=80:20), $R_f=0.27$ (ethyl acetate:n-butanol:pyridine:acetic acid:water=42:21:21:6:10).

The starting material used is obtained as follows:

After the addition of 3.2 g (24 mmol) of hydroxybenztriazole, 1.44 g (12 mmol) of 4-dimethylaminopyridine and 2.72 g (13.2 mmol) of dicyclohexyl carbodiimide, 3.77 g (12 mmol) of 2-(p-biphenylyl)-isopropoxycarbonylglycine and 7.33 g (12 mmol) of N-acetylnormuramyl-L-alanyl-D-isoglutamine-γ-diphenylmethyl ester, dissolved in 100 ml of dimethylformamide, are condensed as described above. The residue (9.8 g) formed after customary working up is purified by countercurrent partitioning according to Craig in the system methanol:water:chloroform:tetrachloromethane=13.5:3.5:4.5:8 in order to remove the 4,6-diacyl compound. After 600 stages, the pure material is collected. 6.9 g (61% strength) of N-acetyl-6-O-[{-2-(p-biphenylyl)-isopropoxycarbonyl}-glycyl]normuramyl- L-alanyl-D-isoglutamine-γ-diphenylmethyl ester are obtained, $[α]_D^{20} = +16°$ (c=0.837; methanol), $R_f = 0.72$ (chloroform:methanol:water = 70:30:5).

EXAMPLE 5

In a manner analogous to that described in Example 4, starting from 2-[{(3'R)-hydroxy-(2'S)-palmitoylaminooctadecyloxy}-hydroxyphosphoryloxy]-ethylamine or 2-(1,2-dipalmitoyl-sn-glycero-3-hydroxyphosphoryloxy)-ethylamine and N-acetyl-4,6-O-distearoylnormuramyl-L-alanyl-D-isoglutamine-N-hydroxysuccinimide ester or N-acetyl-1,4,6-O-triacetylmuramyl-L-alanyl-D-isoglutamine-N-hydroxysuccinimide ester, there are obtained

- N-acetyl-4,6-O-distearoylnormuramyl-L-alanyl-D-isoglutamine-2-[{(3'R)-hydroxy-(2'S)-palmitoylaminooctadecyloxy}hydroxyphosphoryloxy]-ethylamide
- N-acetyl-4,6-O-distearoylnormuramyl-L-alanyl-D-isoglutamine-2-(1',2'-dipalmitoyl-sn-glycero-3'-hydroxyphosphoryloxy)-ethylamide,
- N-acetyl-1,4,6-O-triacetylmuramyl-L-alanyl-D-isoglutamine-2-[{(3'R)-hydroxy-(2'S)-palmitoylaminooctadecyloxy}hydroxyphosphoryloxy]-ethylamide and
- N-acetyl-1,4,6-O-triacetylmuramyl-L-alanyl-D-isoglutamine-2-(1',2'-dipalmitoyl-sn-glycero-3'-hydroxyphosphoryloxy)ethylamide, respectively, in each case in the form of or in admixture with the sodium salt.

The starting materials are manufactured as follows:

A solution of 3.63 g (12 mmol) of stearic acid chloride in 30 ml of absolute tetrahydrofuran is added dropwise at a low temperature, while stirring and with the exclusion of moisture, to a solution of 3.29 g (5 mmol) of N-acetyl-1α-O-benzylnormuramyl-L-alanyl-D-isoglutamine-γ-benzyl ester in 40 ml of absolute pyridine. After standing for 16 hours at room temperature, the mixture is poured onto ice water, the precipitated product is collected and purified over silica gel (1:40) with a mixture of chloroform:ethyl acetate = 1:1.

1.6 g of the material that is uniform in a thin layer chromatogram are dissolved in 40 ml of a mixture of tert.-butanol:water = 98:2 and hydrogenated for 30 hours in the presence of 0.4 g of palladium-on-carbon (10% strength). The catalyst is filtered off, extracted several times at 40° with the above-mentioned solvent mixture and the combined filtrates are concentrated by evaporation. The residue is dissolved in 6 ml of chloroform, filtered through a PTFE millipore filter (0.2μ) and the product is precipitated by the addition of 80 ml of ether:petroleum ether = 4:1 at a low temperature (−10°). 1.2 g of N-acetyl-4,6-O-distearoylnormuramyl-L-alanyl-D-isoglutamine are obtained in the form of an amorphous powder, $[α]_D^{20} = +23±1°$ (c=1; chloroform), $R_f = 0.37$ (chloroform:methanol:water = 70:30:5), $R_f = 0.77$ (ethyl acetate:n-butanol:pyridine:acetic acid:water = 42:21:21:6:10).

3.69 g (5.6 mmol) of N-acetylmuramyl-L-alanyl-D-isoglutamine-γ-diphenylmethyl ester are dissolved in 40 ml of absolute pyridine, 2.04 g (20 mmol) of acetic anhydride are added and the whole is left to stand for one hour. The clear solution is concentrated at 30°, diluted with 200 ml of ethyl acetate and the ethyl acetate phase is extracted 4 times with 50 ml of water each time. The residue remaining after drying and concentrating by evaporation is dissolved in 40 ml of methanol:tetrahydrofuran = 1:1 and treated for one hour with hydrogen after the addition of 0.8 g of a palladium-on-carbon catalyst (10% strength). The catalyst is filtered off with suction, the filtrate is evaporated to dryness and partitioned between n-butanol and water (6 times). The phases that are uniform in a thin layer chromatogram are combined and greatly concentrated at 30°. Water is added several times and the whole is again concentrated. Finally, dilution is effected to a total of 100 ml with distilled water, the solution is filtered through a millipore filter (0.45μ) and lyophilised. 2 g of N-acetyl-1,4,6-O-triacetylmuramyl-L-alanyl-D-isoglutamine in the form of a colourless powder remain, $[α]_D^{20} = +57±1°$ (c=0.92; water), $R_f = 0.4$ (dichloromethane:methanol:acetic acid = 20:5:1).

The diphenylmethyl ester required as starting material is obtained as follows:

2.9 g of diphenyldiazomethane are added to a solution of 5.1 g of N-acetylmuramyl-L-alanyl-D-isoglutamine in 130 ml of 1,2-dimethoxyethane:water = 1:1 and stirred for 24 hours at 40°. A further 1.5 g of reagent are added to the decolorised solution and stirring is continued for a further 24 hours at the above temperature. The cooled suspension is filtered, the precipitate is triturated with ether and washed colourless. The solid residue is suspended in 50 ml of water, filtered off after 30 minutes and dried. 5 g of N-acetylmuramyl-L-alanyl-D-isoglutamine-γ-diphenylmethyl ester remain, $R_f = 0.5$ (dichloromethane:methanol:water = 14:6:1).

EXAMPLE 6

In a manner analogous to that described in Example 4, starting from the N-hydroxysuccinimide ester of succinic acid 2-(1'-palmitoyl-2'-oleoyl-sn-glycero-3'-hydroxyphosphoryloxy)-ethylamide and N-acetylnormuramyl-L-(O-glycyl)-seryl-D-isoglutamine-γ-diphenylmethyl ester hydrochloride, there is obtained, after cleaving the diphenylmethyl ester, N-acetylnormuramyl-L-O-{N-[2-(1'-palmitoyl-2'-oleoyl-sn-glycero-3'-hydroxyphosphoryloxy)ethyl]-succinamoyl)-glycyl}-seryl-D-isoglutamine, which is present partly in sodium salt form.

The following compounds, which are present partly in sodium salt form, are manufactured in an analogous manner:

- N-Acetylmuramyl-L-O-{(N-[2-(1'-palmitoyl-2'-oleoyl-sn-glycero-3'-hydroxyphosphoryloxy)-ethyl]-succinamoyl)glycyl}-seryl-D-isoglutamine,
- N-Acetylmuramyl-D-O-{(N-[2-(1'-palmitoyl-2'-oleoyl-sn-glycero-3'-hydroxyphosphoryloxy)-ethyl]-succinamoyl)glycyl}-seryl-D-isoglutamine,
- N-Acetylmuramyl-D-O-{(N-[2-(1'-palmitoyl-2'-oleoyl-sn-glycero-3'-hydroxyphosphoryloxy)-ethyl]-succinamoyl)-leucyl}seryl-D-isoglutamine,
- 2-Acetylamino-2-desoxy-D-glucopyranosyl-(3)-L-propionyl-D-O-{N-[2-(1'-palmitoyl-2'-oleoyl-sn-glycero-3'-hydroxyphosphoryloxy)-ethyl]-succinamoyl)-glycyl}-seryl-D-isoglutamine,
- 2-Acetylamino-2-desoxy-D-mannopyranosyl-(3)-D-propionyl-L-O-{(N-[2-(1'-palmitoyl-2'-oleoyl-sn-glycero-3'-hydroxyphosphoryloxy)-ethyl]-succinamoyl)-glycyl}-seryl-D-isoglutamine,
- 2-Acetylamino-2-desoxy-D-galactopyranosyl-(3)-D-propionyl-L-O-{(N-2-(1'-palmitoyl-2'-oleoyl-sn-glycero-3'-hydroxyphosphoryloxy)-ethyl]-succinamoyl)-glycyl}seryl-D-isoglutamine,
- N-Acetylnormuramyl-L-O-{(N-[2-(1'-palmitoyl-2'-oleoyl-sn-glycero-3'-hydroxyphosphoryloxy)- ethyl]-succinamoyl)glycyl}-seryl-D-glutamic acid diamide,

N-Propionylnormuramyl-L-O-{(N-[2-(1'-palmitoyl-2'-oleoyl-sn-glycero-3'-hydroxyphosporyloxy)-ethyl]-succinamoyl)glycyl}-seryl-D-isoglutamine, N-Benzoylnormuramyl-L-O-{(N-[2-(1'-palmitoyl-2'-oleoyl-sn-glycero-3'-hydroxyphosphoryloxy)-ethyl]-succinamoyl)glycyl}-seryl-D-glutamic acid dimethyl ester, N-Acetylmuramyl-L-O-{(N-[2-(1'-palmitoyl-2'-oleoyl-sn-glycero-3'-hydroxyphosphoryloxy)-ethyl]-succinamoyl)alanyl}-threonyl-D-isoglutamine, N-Acetylmuramyl-L-O-{(N-[2-(1'-palmitoyl-2'-oleoyl-sn-glycero-3'-hydroxyphosphoryloxy)-ethyl]-succinamoyl)-alanyl}-hydroxyprolyl-D-isoglutaminylalanine, N-Acetylmuramyl-L-O-{(N-[2-(1'-palmitoyl-2'-oleoyl-sn-glycero-3'-hydroxyphosphoryloxy)-ethyl]-succinamoyl)glycyl}-(N-methyl)-seryl-D-isoglutamine, N-Acetylmuramyl-L-O-{(N-[2-(1'-palmitoyl-2'-oleoyl-sn-glycero-3'-hydroxyphosphoryloxy)-ethyl]-succinamoyl)glycyl}-seryl-D-(γ-carboxy)-isoglutamine, N-Acetylmuramyl-L-O-{(N-[2-(1'-palmitoyl-2'-oleoyl-sn-glycero-3'-hydroxyphosphoryloxy)-ethyl]-succinamoyl)glycyl}-seryl-D-(γ-carboxy)-glutamylglycineamide.

EXAMPLE 7

N-acetyl-1α-O-benzyl-4,6-O-isopropylidenenormuramyl-L-seryl-D-isoglutaminebenzyl ester is reacted in the presence of pyridine and 2,4-6-triisopropylbenzenesulphonyl chloride with the di-sodium salt of (1,2-dipalmitoyl-rac-glycero-3)-phosphoric acid ester to form N-acetyl-1α-O-benzyl-4,6-O-isopropylidenenormuramyl-L-O-(1,2-dipalmitoyl-rac-glycero-3-hydroxyphosphoryl)-seryl-D-isoglutamine, which is present partly in salt form, from which first the isopropylidene group is removed by acid hydrolysis and then the benzyl radical by catalytic hydrogenation, in each case as described above, after which N-acetylnormuramyl-L-O-(1,2-dipalmitoyl-rac-glycerol-3-hydroxyphosphoryl)-seryl-D-isoglutamine is obtained, which is present partly in sodium salt form.

EXAMPLE 8

The benzyloxycarbonyl group is removed in customary manner from N-benzyloxycarbonyl-1α-O-benzyl-muramyl-L-alanyl-D-isoglutamine-tert.-butyl ester. The resulting product, which has a free 2-amino group, is reacted with 2-(1,2-dipalmitoyl-rac-glycero-3-hydroxyphosphoryloxy)acetic acid N-succinimide ester to form 1α-O-benzyl-N-(1,2-dipalmitoyl-rac-glycero-3-hydroxyphosphoryloxy)acetylmuramyl-L-alanyl-D-isoglutamine-tert.-butyl ester. After hydrolysing the tert.-butyl ester with trifluoroacetic acid in methylene chloride and then removing the benzyl protecting group with hydrogen in the presence of a palladium catalyst, N-(1,2-dipalmitoyl-rac-glycero-3-hydroxyphosphoryloxy)-acetylmuramyl-L-alanyl-D-isoglutamine is obtained.

EXAMPLE 9

N-acetyl-1α-O-benzylnormuramyl-L-alanyl-D-isoglutaminebenzyl ester is reacted according to the Steglich method (dimethylaminopyridine, dicyclohexyl carbodiimide and pyridine) with (1,2-dipalmitoyl-rac-glycero-3-hydroxyphosphoryloxy)-acetic acid N-succinimide ester. After removing the benzyl protecting groups with hydrogen in the presence of a palladium catalyst, N-acetyl-6-O-([1,2-dipalmitoyl-rac-glycero-3-hydroxyphosphoryloxy]acetyl)-normuramyl-L-alanyl-D-isoglutamine is obtained.

EXAMPLE 10

N-acetylnormuramyl-1α-O-benzyl-L-alanyl-D-isoglutaminebenzyl ester is reacted in the presence of pyridine and 2,4,6-triisopropylbenzenesulphonyl chloride with the di-sodium salt of (1,2-dipalmitoyl-rac-glycero-3)phosphoric acid ester. There is obtained from the resulting product, after removing the benzyl protecting groups with hydrogen in the presence of a palladium catalyst, N-acetyl-6-O-(1,2-dipalmitoyl-rac-glycero-3-hydroxyphosphoryloxy)-normuramyl-L-alanyl-D-isoglutamine.

EXAMPLE 11

N-acetyl-1α-O-benzyl-4,6-O-benzylidenemuramic acid ethyl ester is hydrolysed with boiling potassium hydroxide solution to form the potassium salt of 1α-O-benzyl-4,6-O-benzylidenemuramic acid. After reacting the resulting product with benzyloxycarbonyl chloride at pH 8, N-benzyloxycarbonyl-1α-O-benzyl-4,6-O-benzylidenemuramic acid is obtained which is reacted with L-alanyl-D-isoglutamine-tert.-butyl ester in the presence of dicyclohexyl carbodiimide and N-hydroxysuccinimide to form N-benzyloxycarbonyl-1α-O-benzyl-4,6-O-benzylidenemuramyl-L-alanyl-D-isoglutamine-tert.-butyl ester. The benzyloxycarbonyl radical and the benzylidene group are removed selectively by gentle brief hydrogenation on a palladium-on-carbon catalyst. The resulting product is acylated at the free 2-amino group with succinic acid monobenzyl ester in the presence of dicyclohexyl carbodiimide and N-hydroxysuccinimide to form N-benzyloxysuccinyl-1α-O-benzyl-muramyl-L-alanyl-D-isoglutamine-tert.-butyl ester. From this, the 1α-O-benzyl protecting group is removed by relatively long hydrogenation with palladium-on-carbon contact. The resulting product is reacted with 2-(1,2-dipalmitoyl-sn-glycero-3-hydroxyphosphoryloxy)-ethylamine in the presence of dicyclohexyl carbodiimide and N-hydroxysuccinimide to form N-(2-[1,2-dipalmitoyl-sn-glycerohydroxyphosphoryloxy]-ethyl)-succinamoylmuramyl-L-alanyl-D-isoglutamine-tert.-butyl ester from which, after the acidic removal of the tert.-butyl group, N-(2-[1,2-dipalmitoyl-sn-glycerohydroxyphosphoryloxy]ethyl)-succinamoylmuramyl-L-alanyl-D-isoglutamine is obtained.

EXAMPLE 12

Manufacture of 1000 capsules each containing 260 mg of the active ingredients:

| Composition: | |
|---|---|
| rifampicin | 250 g |
| N—(2-[1,2-dipalmitoyl-sn-glycero-hydroxyphosphoryloxy]-ethyl)-succinamoylmuramyl-L-alanyl-D-isoglutamine which is partly in sodium salt form | 10 g |
| talc | 36 g |
| wheat starch | 24 g |
| magnesium stearate | 16 g |
| lactose | 4 g |

-continued

| Composition: | |
|---|---|
| | 340 g |

Preparation

The pulverulent substances are beaten through a sieve having a mesh width of 0.6 mm and mixed thoroughly. Using a capsule-filling machine, gelatin capsules are prepared with 340 g of this mixture each.

EXAMPLE 13

Manufacture of 1000 capsules each containing 105 mg of the active ingredients.

| Composition: | |
|---|---|
| rifampicin | 100 g |
| N—acetylnormuramyl-L-O—(1,2-dipalmitoyl-rac-glycero-3-hydroxyphosphoryl)-seryl-D-isoglutamine which is partly in sodium salt form | 5 g |
| ethylcellulose | 3 g |
| stearic acid | 3 g |
| | 111 g |

Preparation

The ethylcellulose and the stearic acid are dissolved in 120 ml of methylene chloride, the antibiotic is added and the substance is beaten through a sieve having a mesh width of 0.6 mm at a temperature of approximately 40°, the methylene chloride evaporating. 156 mg of the resulting granulate are introduced into 0.5 ml gelatin capsules by means of a capsule-filling machine.

EXAMPLE 14

Manufacture of an animal feed containing 0.005% of the active ingredients:

| Pre-mix: | |
|---|---|
| rifampicin or chlorotetracyclin | 30 g |
| N—acetyl-6-O—{N—[2-(1,2-dipalmitoyl-sn-glycero-3-hydroxyphosphoryloxy)-ethyl]-succinamoyl}-normuramyl-L-alanyl-D-isoglutamine which is partly in sodium salt form | 10 g |
| powdered sugar | 50 g |
| soya bean feed (extracted with solvents) | 275 g |
| | 365 g |
| Additives: | |
| maize meal | 500.0 kg |
| soya bean meal, 44% protein | 300.0 kg |
| alfalfa meal | 13.5 kg |
| dicalcium phosphate | 18.0 kg |
| calcium carbonate (ground) | 4.5 kg |
| salt | 2.3 kg |
| fish meal, 60% protein | 18.0 kg |
| stabilised fat | 27.0 kg |
| dry whey residue | 18.0 kg |
| manganese sulphate | 0.2 kg |
| zinc oxide | 1.3 kg |
| d,l-methionine | 0.7 kg |
| vitamin pre-mix | 4.5 kg |
| | 908.0 kg |

The vitamin pre-mix contains in 4.5 kg: 16,000,000 I.U. vit. A, 1,000,000 I.U. vit. $D_3$, 5,000 I.U. vit. E acetate, 6 g vit. $K_3$, 6 mg vit. $B_{12}$, 3 g riboflavin, 30 g niacin, 5 g calcium pantothenate and 100 g ethoxyquin (1,2-dihydro-6-ethoxy-2,2,4-trimethylquinoline) and maize meal to make up to 4.5 kg.

Method of manufacture

The active ingredients and sugar are mixed thoroughly with one another, beaten through a sieve having a mesh width of 0.6 mm and then mixed with the soya bean meal. The pre-mix is then added to the feed in the quantity corresponding to the final concentration desired and homogenised in a horizontal drum mixer.

EXAMPLE 15

120 mg of the sodium salt of N-{N-[2-(1',2'-dipalmitoyl-sn-glycero-3'-hydroxyphosphoryloxy)-ethyl]succinamoyl}-muramyl-L-alanyl-D-isoglutamine-tert.-butyl ester are dissolved in 12 ml of a mixture of 3 ml of trifluoroacetic acid and 9 ml of methylene chloride and the solution is left to stand for 3 hours at room temperature. It is then evaporated to dryness in vacuo at 40°, the residue is triturated several times with ether and the colourless crystalline residue is purified over silica gel in the eluant chloroform:methanol:sodium phosphate buffer (pH = 7) = 55:45:2.

A colourless crystallisate of N-{N-[2-(1',2'-dipalmitoyl-sn-glycero-3'-hydroxyphosphoryloxy)-ethyl]succinamoyl}-muramyl-L-alanyl-D-isoglutamine is obtained which is present partly in sodium salt form and has the decomposition point: 196°–197°; $R_f$=0.23 (chloroform:methanol:water = 60:40:2), $[\alpha]_D^{20}$ = +15° (c=0.9; chloroform:methanol = 1:1).

The substance reacts positively with phosphorus spray [V. E. Vaskovsky et al., J. Lipid Research 9, 396 (1968)], with aniline hydrogen phthalate, with dilute sulphuric acid and with sodium hypochlorite/N,N-tetramethyl-4,4'-diaminodiphenylmethane (TDM). 360 MHz-$^1$H-NMR spectrum ( ):

$\delta$ = 1.40 ($CH_3$ of alanine and the propionyl group), 0.88, 1.27 and 1.60 (methyl and methylene groups [apart from $\alpha$-methylene groups] of the palmitoyl radicals), 2.32 ($\alpha$-methylene groups of the palmitoyl radicals), 1.9–2.2 (methylene groups of the succinamoyl and isoglutamine radicals), 4.15 ($\gamma$-H of the glycero radical), 5.22 ($\beta$-H of the glycero radical), 5.36 (1-H of the muramyl radical).

The starting material is obtained as follows:

404.6 mg (0.733 mmol) of the formic acid addition salt of muramyl-L-alanyl-D-isoglutamine-$\gamma$-tert.-butyl ester, 720 mg (0.807 mmol) of the sodium salt of N-[2-(1',2'-dipalmitoyl-sn-glycero-3'-hydroxyphosphoryloxy)ethyl]-succinamide, 118 mg (1.026 mmol) of N-hydroxysuccinimide, 211 mg (1.026 mmol) of dicyclohexyl carbodiimide and 142 ml (1.026 mmol) of triethylamine are dissolved in a mixture of 12 ml of dimethylacetamide and 4 ml of chloroform and the whole is left to react for 18 hours at room temperature. After the addition of 1 ml of water, the reaction solution is concentrated by evaporation in vacuo, taken up in chloroform and the crystals (dicyclohexylurea) are filtered off with suction. The filtrate is chromatographed over silica gel, Merck. Elution is carried out in succession with in each case 200 ml of the solvent mixtures chloroform:methanol = 9:1, chloroform:methanol = 8:2, chloroform:methanol = 7:3, chloroform:methanol:water = 70:30:1 and chloroform:methanol:water = 70:30:10.

The fractions of the desired substance that react positively with phosphorus spray, aniline hydrogen phthalate, dilute sulphuric acid and sodium hypochlorite/TDM are collected and, after concentration by evaporation, yield a colourless powder having a decomposition range of 144°-152° (anomer mixture) and $R_f=0.455$ (chloroform:methanol:water=70:30:3).

The muramyl peptide used as the starting material for the above experiment is obtained as follows:

1.6 g of N-tert.-butoxycarbonyl-4,6-O-isopropylidene-muramyl-L-alanyl-D-isoglutamine-γ-tert.-butyl ester are dissolved in a mixture of 1 ml of dimethoxyethane and 25 ml of 40% aqueous formic acid. After 36 hours at room temperature (25°) and 18 hours at 4° the solution is diluted with 75 ml of distilled water and lyophilised. A colourless amorphous powder is obtained which is chromatographed over silica gel, Merck, there being used in succession elution mixtures of chloroform:methanol:water in the following quantitative ratios: 90:10:1; 80:20:1; 70:30:1 and 60:40:1.

After concentrating the pure fractions by evaporation, there is obtained a colourless amorphous powder of the formic acid addition salt of muramyl-L-alanyl-D-isoglutamine-γ-tert.-butyl ester with $R_f=0.31$ (chloroform:methanol:water=60:40:2), $[\alpha]_D^{20}=+57°$ (c=0.956, methanol) and a decomposition range of 70°-90° (anomer mixture). The substance reacts positively with ninhydrin, aniline hydrogen phthalate, dilute sulphuric acid and sodium hypochlorite/TDM.

The succinoylcephalin used as starting material is obtained as follows:

4 g of 2-(1',2'-dipalmitoyl-sn-glycero-3'-hydroxyphosphoryloxy)-ethylamine (cephalin) and 1.16 g of succinic acid anhydride are suspended in 150 ml of a mixture of chloroform:methanol:water=8:10:4, and 2.4 ml of triethylamine are added while stirring. A clear colourless solution is obtained to which, after 2 hours at room temperature, a further 0.3 g of succinic acid anhydride and 0.6 ml of triethylamine are added. After a further one hour at room temperature, the solution is concentrated by evaporation in vacuo. The residue is dissolved in a little tetrahydrofuran, the solution is adjusted to pH=2 with 1 N hydrochloric acid and the phospholipid is extracted with ethyl acetate. The organic phase is washed with water and then with sodium chloride solution. After drying the ethyl acetate phase with sodium sulphate there is obtained by chromatography pure N-[2-(1',2'-dipalmitoyl-sn-glycero-3'-hydroxyphosphoryloxy)-ethyl]succinamide, which is partly in sodium salt form, with $R_f=0.3$ (chloroform:methanol:water=70:30:3; for comparison: $R_f$ of cephalin=0.535).

The melting point is not clear (82°-110°) since the compound is, according to a thin layer test, partially converted into a lipophilic compound when heated.

The N-tert.-butoxycarbonyl-4,6-O-isopropylidenemuramyl-L-alanyl-D-isoglutamine-γ-tert.-butyl ester is obtained by catalytic hydrogenation of the corresponding α-benzyl glycoside:

3.6 g of benzyl glycoside are hydrogenated at normal pressure in 90 ml of a mixture of dimethoxyethane:methylene chloride=8:2 with the addition of 2.2 g of 10% palladium-on-carbon. After 90 hours, hydrogenation is complete; the catalyst is filtered off and the filtrate is concentrated to dryness by evaporation in vacuo. There results a colourless amorphous powder having a melting point of 180°-188° and $R_f=0.36$ (chloroform:methanol=9:1; for comparison: $R_f$ of benzyl glycoside=0.6). The compound reacts positively with aniline hydrogen phthalate, dilute sulphuric acid and sodium hypochlorite/TDM.

The benzyl glycoside used as starting material is obtained as follows:

6 g (12.5 mmol) of 1α-O-benzyl-N-tert.-butoxycarbonyl-4,6-O-isopropylidenemuramic acid, 4.6 g (15 mmol) of the hydrochloride of L-alanyl-D-isoglutamine-γ-tert.-butyl ester, 3.1 g (15 mmol) of dicyclohexyl carbodiimide, 1.7 g of N-hydroxysuccinimide and 2.07 ml (15 mmol) of triethylamine are dissolved in 120 ml of a mixture of dimethylformamide:methylene chloride=3:2.

The clear colourless solution is stirred for 5 hours at room temperature in the course of which dicyclohexylurea precipitates. The precipitate is filtered off with suction and the filtrate is evaporated to dryness in vacuo. The residue is taken up in methylene chloride and extracted by shaking once with 0.1 N hydrochloric acid and then immediately several times with water until the result of a test for chloride ions is negative. The organic phase is dried over sodium sulphate and the solution is evaporated to dryness. The residue is extracted with ethyl acetate at room temperature, the undissolved dicyclohexylurea is filtered off with suction and petroleum ether is added to the filtrate. The 1α-O-benzyl-N-tert.-butoxycarbonyl-4,6-O-isopropylidenemuramyl-L-alanyl-D-isoglutamine-γ-tert.-butyl ester having a melting point of 93°-97° and $[\alpha]_D^{20}=+80°$ (c=0.98; chloroform) precipitates in the form of colourless crystals.

The potassium salt of 1α-O-benzyl-N-tert.-butoxycarbonyl-4,6-O-isopropylidenemuramic acid is obtained as follows:

22.7 g of 1α-O-benzyl-N-acetyl-4,6-O-isopropylidenemuramic acid ethyl ester are left to stand for 12 hours at room temperature in a solution of 5.1 g of potassium hydroxide in 200 ml of methanol and 5 ml of water. At the end of this period the ethyl ester has been hydrolysed. Concentration is effected in vacuo, 80 ml of hydrazine hydrate are added to the residue and the mixture is allowed to react for 48 hours at 80°. The solution is then concentrated by evaporation at 0.1 torr and the residue is partitioned between saturated potassium chloride solution and tetrahydrofuran. The potassium salt of 1α-O-benzyl-4,6-O-isopropylidenemuramic acid with $R_f=0.5$ (chloroform:methanol=3:1) is in the organic phase together with a small amount of unhydrolysed N-acetyl compound with $R_f=0.6$.

The resulting crude amine is reacted directly with di-O-tert.-butylcarbonic acid anhydride:

9.4 g of the crude amine are dissolved in a mixture of 35 ml of dioxan and 25 ml of water, a solution of 3.2 g of potassium carbonate in 20 ml of water is added and to this mixture a solution of di-O-tert.-butylcarbonic acid anhydride in 20 ml of dioxan is added dropwise at 10°. The mixture is then left for a further 2 hours at room temperature in order to complete the reaction. The pH value of the solution is maintained at a constant 9-10 by the addition of potassium carbonate solution. The resulting suspension is adjusted to pH=7 with 2 N hydrochloric acid, the aqueous phase is saturated with potassium chloride and extracted with ethyl acetate. The organic phase is washed with water, dried over sodium sulphate and concentrated by evaporation. The resulting residue is purified chromatographically over silica gel, Merck, with the solvent mixtures ether:ethyl acetate=1:1 and chloroform:acetone=8:2 in succession.

The resulting potassium salt of 1α-O-benzyl-N-tert.-butoxycarbonyl-4,6-O-isopropylidenemuramic acid decomposes at 250°-255°; $R_f=0.82$ (ether:tetrahydrofuran=9:1), $R_f$=0.64 (methylene chloride:methanol=9:1), $[\alpha]_D^{20}$= +105° (c=1.07; chloroform).

EXAMPLE 16

828 mg (1.494 mmol) of the formic acid addition salt of muramyl-L-alanyl-D-isoglutamine-γ-tert.-butyl ester described in Example 15, 726 mg (0.996 mmol) of the monosodium salt of 2-(1',2'-dipalmitoyl-rac-glycero-3'-hydroxyphosphoryloxy)-acetic acid and 620 mg (2.49 mmol) of 2-ethoxy-N-ethoxycarbonyl-1,2-dihydroquinoline (EEDQ) are dissolved in 17 ml of a mixture of chloroform:methanol:water=75:25:4 and the pH value is adjusted to 7 with 138 μl of N-ethylmorpholine. After 24 hours at room temperature the reaction is complete according to a thin layer test. The mixture is concentrated to a syrup by evaporation in vacuo and purified by chromatography over silica gel, Merck, with the solvent mixture chloroform:methanol:water=70:30:1. The monosodium salt of N-{2-[1',2'-dipalmitoyl-rac-glycero-3'-hydroxyphosphoryloxy]-acetyl}-muramyl-L-alanyl-D-isoglutamine-γ-tert.-butyl ester is obtained in the form of a colourless amorphous powder with $R_f$=0.68 (chloroform:methanol:water=70:30:1) and $[\alpha]_D^{20}$= +10° (c=0.8; chloroform:methanol=1:1). 200 mg of the resulting tert.-butyl ester are dissolved in 16 ml of a mixture of trifluoroacetic acid:methylene chloride=1:3. After 3 hours at room temperature, the mixture is evaporated to dryness in vacuo and the residue is extracted several times with ether. In this manner there is obtained a colourless amorphous powder of the monosodium salt of N-{2-[1',2'-dipalmitoyl-rac-glycero-3'-hydroxyphosphoryloxy]acetyl}-muramyl-L-alanyl-D-isoglutamine with $R_f$=0.095 (chloroform:methanol:water=70:30:1) and $R_f$=0.25 (chloroform:methanol:water=55:45:1).

The substance reacts positively with aniline hydrogen phthalate, phosphorus spray, sodium hypochlorite/TDM and dilute sulphuric acid.

The sodium salt of 2-(1,2-dipalmitoyl-rac-glycero-3-hydroxyphosphoryloxy)-acetic acid used as starting material is obtained by catalytic hydrogenation of the corresponding benzyl ester with 10% palladium-on-carbon in a mixture of dimethoxyethane:chloroform=1:1. The compound is formed as a colourless crystallisate with $R_f$=0.1 (chloroform:methanol:water=70:30:3) and m.p. 105°-108°.

The benzyl ester of this compound used as starting material is manufactured as follows:

To 0.704 ml (7.7 mmol) of phosphoryl chloride (POCl$_3$) in 10 ml of tetrahydrofuran there are added dropwise at 10° 4.0 g (7 mmol) of 1,2-O-dipalmitoyl-rac-glycerin in 20 ml of tetrahydrofuran and then at 0°-5° 1.06 ml of triethylamine in 10 ml of tetrahydrofuran. After 1 hour at room temperature the mixture is cooled again to 5° and a further 1.06 ml of triethylamine in 10 ml of tetrahydrofuran and 1.28 g (7.7 mmol) of glycolic acid benzyl ester in 20 ml of tetrahydrofuran are added dropwise at that temperature. After 1.5 hours at room temperature, the mixture is cooled again to 0° and 10 ml of water and a solution of 2.03 ml of triethylamine in 10 ml of tetrahydrofuran are added dropwise.

After a further 2 hours at room temperature, the solution is concentrated by evaporation in vacuo, the residue is taken up in chloroform and thoroughly shaken several times with saturated sodium chloride solution. After drying the chloroform phase over sodium sulphate and concentrating by evaporation, the crude product is obtained in the form of the monosodium salt which is purified by chromatography over silica gel, Merck, in methylene chloride:methanol=9:1. The diastereoisomeric mixture of 2-(1,2-dipalmitoyl-rac-glycero-3-hydroxyphosphoryloxy)acetic acid benzyl ester is obtained in the form of the monosodium salt having a melting point of 65°-68°. By chromatographing a second time, a partial quantity is isolated having an identical $R_f$ value (0.3, methylene chloride:methanol=9:1) and an identical elementary analysis but a melting point of 160°-165°. The 1:1 diastereoisomeric mixture was used for the further reactions.

EXAMPLE 17

0.277 g (1.1 mmol) of dicyclohexyl carbodiimide is added to a solution of 0.322 g (1.0 mmol) of phosphoric acid hexadecyl ester in 10 ml of absolute pyridine and the whole is stirred for 1 hour at room temperature under argon. 0.673 g (1.0 mmol) of N-acetyl-1α-O-benzylmuramyl-L-alanyl-D-isoglutamine-γ-benzyl ester, dissolved in 10 ml of a mixture of dimethylacetamide:pyridine=1:1, and 0.061 g (0.5 mmol) of 4-dimethylaminopyridine are then added and the mixture is stirred for a further 18 hours at room temperature under argon. The resulting suspension is then concentrated by evaporation at 30° in a high vacuum. The solid white residue is suspended in 50 ml of methanol, filtered off from a portion of unreacted γ-benzyl ester derivative and concentration by evaporation is carried out again.

The resulting residue is then dissolved in 50 ml of chloroform and this solution is extracted by shaking with 25 ml of 10% sodium chloride solution. The chloroform phase is dried over sodium sulphate, filtered and concentrated by evaporation.

The resulting crude product consisting of the monosodium salt of N-acetyl-1α-O-benzyl-6-O-hexadecyloxyhydroxyphosphorylmuramyl-L-alanyl-D-isoglutamine-γ-benzyl ester and the disodium salt of N-acetyl-1α-O-benzyl-4,6-O-di-hexadecyloxyhydroxyophosphorylmuramyl-L-alanyl-D-isoglutamine-γ-benzyl ester is freed of impurities by column chromatography over silica gel 60 (1:50; 0.063–0.002 mm, Merck) in the system chloroform:methanol=9:1 and then the desired products are eluted with chloroform:methanol=6:1. The appropriate fractions are collected and concentrated by evaporation in a high vacuum.

There are obtained the disodium salt of N-acetyl-1α-O-benzyl-4,6-O-di-hexadecyloxyhydroxyphosphorylmuramyl-L-alanyl-D-isoglutamine-γ-benzyl ester with $R_f$=0.52 (chloroform:methanol:water=70:30:5) and the monosodium salt of N-acetyl-1α-O-benzyl-6-O-hexadecyloxyhydroxyphosphorylmuramyl-L-alanyl-D-isoglutamine-γ-benzyl ester with $R_f$=0.71 (chloroform:methanol:water=70:30:5), both in the form of an amorphous colourless powder.

0.25 g (0.25 mmol) of the monosodium salt of N-acetyl-1α-O-benzyl-6-O-hexadecyloxyhydroxyphosphorylmuramyl-L-alanyl-D-isoglutamine-γ-benzyl ester is hydrogenated for 60 hours at room temperature and under normal pressure in 25 ml of chloroform:1,2-dimethoxyethane:water=1:10:1 in the presence of a total of 0.25 g of 10% palladium-on-carbon. Afterwards the catalyst is filtered off and the filtrate is evaporated to dryness at 40° in a high vacuum. The resulting solid white residue is dissolved in 50 ml of twice distilled water and this solution is filtered through a PTFE (polytetrafluoroethylene, Teflon) millipore filter (0.2μ) and lyophilised.

0.2 g of the monosodium salt of N-acetyl-6-O-hexadecyloxyhydroxyphosphorylmuramyl-L-alanyl-D-isoglutamine is obtained in the form of an amorphous colourless powder with $R_f$=0.7 (chloroform:methanol:water=5:5:1).

0.4 g (0.31 mmol) of the disodium salt of N-acetyl-1α-O-benzyl-4,6-O-di-hexadecyloxyhydroxyphosphorylmuramyl-L-alanyl-D-isoglutamine-γ-benzyl ester is hydrogenated for 60 hours at room temperature and under normal pressure in 40 ml of chloroform:1,2-dimethoxyethane:water=1:10:1 in the presence of a total of 0.4 g of 10% palladium-on-carbon. The catalyst is then filtered off and the filtrate is evaporated to dryness at 40° in a high vacuum. The resulting solid white residue is dissolved in 60 ml of twice distilled water and this solution is filtered through a PTFE millipore filter (0.2μ) and lyophilised. 0.3 g of the disodium salt of N-acetyl-4,6-O-di-hexadecyloxyhydroxyphosphorylmuramyl-L-alanyl-D-isoglutamine is obtained in the form of an amorphous colourless powder with $R_f$=0.48 (chloroform:methanol:water=5:5:1).

EXAMPLE 18 0.454 g (2.2 mmol) of dicyclohexyl carbodiimide is added to a solution of 0.644 g (2.0 mmol) of phosphoric acid hexadecyl ester in 20 ml of absolute pyridine and the mixture is stirred for 1 hour at room temperature under argon.

0.673 g (1.0 mmol) of N-acetyl-1α-O-benzylmuramyl-L-alanyl-D-isoglutamine-γ-benzyl ester, dissolved in 10 ml of a mixture of dimethylacetamide:pyridine=1:1, and 0.061 g (0.5 mmol) of 4-dimethylaminopyridine are then added and the mixture is stirred for a further 22 hours at room temperature under argon. The resulting cloudy solution is then concentrated by evaporation at 30° in a high vacuum.

The residue is taken up in 100 ml of chloroform, the insoluble portion is filtered off and the chloroform solution is twice extracted by shaking with 25 ml of 10% sodium chloride solution each time. The chloroform phase is dried over sodium sulphate, filtered and concentrated by evaporation.

The resulting crude disodium salt of N-acetyl-1α-O-benzyl-4,6-O-di-hexadecyloxyhydroxyphosphorylmuramyl-L-alanyl-D-isoglutamine-γ-benzyl ester is purified of the small amount of the monosodium salt of N-acetyl-1α-O-benzyl-6-O-hexadecyloxyhydroxyphosphorylmuramyl-L-alanyl-D-isoglutamine-γ-benzyl ester, starting materials and impurities by column chromatography over silica gel 60 (1:50; 0.063-0.002 mm, Merck).

First the impurities are eluted with chloroform: methanol=9:1 and then the desired product with chloroform: methanol=6:1. The appropriate fractions are collected and concentrated by vaporation in a high vacuum.

0.97 g of the disodium salt of N-acetyl-1α-O-benzyl-4,6-O-di-hexadecyloxyhydroxyphosphorylmuramyl-L-alanyl-D-isoglutamine-γ-benzyl ester is obtained in the form of an amorphous colourless powder with $R_f$=0.52 (chloroform:methanol:water=70:30:5) from which the protecting groups are removed by catalytic hydrogenation in a manner analogous to that described in Example 17.

EXAMPLE 19

5 ml (50 mmol) of acetic anhydride (purissimum) are added to a solution of 0.5 g (0.38 mmol) of the sodium salt of N-acetylmuramyl-L-alanyl-D-isoglutaminyl-L-alanyl-2-(1',2'-dipalmitoyl-sn-glycero-3'-hydroxyphosphoryloxy)-ethylamide, which contains 3 mol of water, in 10 ml of absolute pyridine and the whole is stirred for 24 hours at room temperature. The resulting solution is then concentrated by evaporation at 40° in a high vacuum and the white residue so obtained is suspended several times in 50 ml of water and lyophilised. The pure-white lyophilisate is dissolved in 100 ml of twice distilled water and this solution is first filtered over Hyflo and then through a PTFE (polytetrafluoroethylene) millipore filter (0.2μ) and again lyophilised.

The sodium salt of N-acetyl-1,4,6-O-triacetylmuramyl-L-alanyl-D-isoglutaminyl-L-alanyl-2-(1',2'-dipalmitoyl-sn-glycero-3'-hydroxyphosphoryloxy)-ethylamide is obtained in the form of a pure-white powder, which still contains 3 mol of water, with $[\alpha]_D^{20}$= +17.6±1° (c=0.165; water) and $R_f$=0.40 (chloroform:methanol:water=65:25:4).

EXAMPLE 20

0.176 g of N-acetyl-1α-O-benzyl-6-O-{N-[2-(1',2'-dipalmitoyl-sn-glycero-3'-hydroxyphosphoryloxy)-ethyl]-succinamoyl}-muramyl-L-α-aminobutyryl-D-isoglutamine-γ-benzyl ester, dissolved in 160 ml of dimethoxyethane:water=4:1, is treated with hydrogen in the presence of 0.2 g of palladium-on-carbon (10% strength) for 46 hours. The catalyst is filtered off, the filtrate is concentrated to dryness by evaporation and freeze-dried from tert.-butanol:water=4:1. The crude product is separated by thick-layer chromatography over silica gel (five 20×20 cm PSC prepared plates, silica gel 60, F 254, thickness: 2 mm, Merck). The layer, identified on the basis of UV fluorescence, that contains the product is extracted with chloroform:tert.-butanol=1:1 and, after filtration (PTFE-millipore, 0.2μ), is freeze-dried from tert.-butanol:water=20:1. After continuous diafiltration (Amicon filter YN 10, nominal separation limit 10,000 dalton) against a 1:1 mixture of 0.1 molar phosphate buffer, pH=7, and 0.1 molar sodium chloride solution and subsequent lyophilisation, N-acetyl-6-O-{N-[2-(1',2'-dipalmitoyl-sn-glycero-3'-hydroxyphosphoryloxy)ethyl]-succinamoyl}-muramyl-L-α-aminobutyryl-D-isoglutamine, partly in sodium salt form, is obtained as a colourless powder with $[\alpha]_D^{20}$= +11±1° (c=0.253; dimethylformamide), $R_f$=0.38 (chloroform:methanol:water=70:30:5) and $R_f$=0.72 (chloroform:methanol:acetic acid:water=25:15:4:2).

The starting material is obtained as follows:

0.234 g (0.3 mmol) of N-acetyl-1α-O-benzyl-6-O-succinoylmuramyl-L-α-aminobutyryl-D-isoglutamine-γ-benzyl ester and 0.092 g (0.36 mmol) of di-(N-succinimidyl)carbonate (Fluka purissimum) is dissolved in 10 ml of absolute dimethylformamide and, after the addition of 0.1 ml (1.2 mmol) of absolute pyridine, the solution is maintained at 35° for 3 hours with the exclusion of moisture. 0.208 g (0.30 mmol) of 2-(1',2'-dipalmitoyl-sn-glycero-3'-hydroxyphosphoryloxy)-ethylamine (=cephalin), dissolved in 3 ml of chloroform:methanol=7:3, is then added and the whole is allowed to react, while stirring, for 6 hours at 35°. For working up, the thin suspension is concentrated by evaporation. The crude product is washed in succession with water, aqueous acetonitrile and acetonitrile on an OPTI-UPC$_{12}$ column (silica gel treated with dodecyltrichlorosilane, 80 g, coated four times, 40-63 μm, ANTEC). Finally, the product is eluted with methanol:water=9:1. After concentration by evaporation and lyophilisation from tert.-butanol, N-acetyl-1α-O-benzyl-6-O-{N-[2-(1',2'-dipalmitoyl-sn-glycero-3'-hydroxyphosphoryloxy)-ethyl]-succinamoyl}muramyl-L-α-aminobutyryl-D-isoglutamine-γ-benzyl ester is obtained in the form of a loose powder with $[\alpha]_D^{20} = +8 \pm 1°$ (c=0.435; chloroform) and $R_f = 0.27$ (chloroform:methanol = 7:3).

The starting material is manufactured as follows:

0.80 g (7.85 mmol) of succinic acid anhydride in 15 ml of absolute ethyl acetate is added at a low temperature to 2.00 g (3.1 mmol) of N-acetyl-1α-O-benzyl-4,6-O-isopropylidenemuramyl-L-α-aminobutyryl-D-isoglutamine-γ-benzyl ester, dissolved in 30 ml of absolute pyridine, and the whole is left to stand for three days at room temperature. The clear solution is cooled to 0°, 50 ml of 0.5 N citric acid solution are added dropwise and the reaction solution is stirred for 2 hours. It is then concentrated to approximately 5 ml, 40 ml of tert.-butanol are added and the whole is lyophilised. The further purification process is carried out on a $UPC_{12}$ column (80 g), in a manner analogous to that described above, beginning with a mixture of acetonitrile:water = 1:3 (20 ml fractions). The product is eluted with acetonitrile:water = 3:1 and the combined fractions are greatly concentrated and lyophilised from tert.-butanol:water = 4:1.

N-acetyl-1α-O-benzyl-6-O-succinoylmuramyl-L-α-aminobutyryl-D-isoglutamine-γ-benzyl ester is obtained in the form of a colourless loose powder with $[\alpha]_D^{20} = +36 \pm 1°$ (c=0.618; dimethylformamide), $R_f = 0.45$ (chloroform:methanol:water = 70:30:5) and $R_f = 0.68$ (ethyl acetate:acetic acid:water:methanol = 67:10:23:12).

The starting material used is obtained in the following manner:

2.80 g (4.4 mmol) of N-acetyl-1α-O-benzyl-4,6-O-isopropylidenemuramyl-L-α-aminobutyryl-D-isoglutamine-γ-benzyl ester, dissolved in 30 ml of 60% acetic acid, are left to stand at room temperature for 24 hours. The reaction solution is concentrated in a rotary evaporator at 30° to approximately 5 ml and, after the addition of 35 ml of tert.-butanol, is lyophilised. 2.1 g of N-acetyl-1α-O-benzylmuramyl-L-α-aminobutyryl-D-isoglutamine-γ-benzyl ester with $[\alpha]_D^{20} = +44 \pm 1°$ (c=0.635; methanol), and $R_f = 0.62$ (acetonitrile:water = 3:1) and $R_f = 0.72$ (ethyl acetate:n-butanol:pyridine:acetic acid:water = 42:21:21:6:10) are obtained.

EXAMPLE 21

After the addition of 0.2 g of a palladium-on-carbon catalyst (10% strength), 0.20 g (0.21 mmol) of N-acetyl-1α-O-benzylnormuramyl-L-O-{N-[2-tetradecyloxyhydroxyphosphoryloxy)-ethyl]-succinamoyl}-seryl-D-isoglutamine-γ-tert.-butyl ester, dissolved in 50 ml of dimethoxyethane:water = 10:1, is hydrogenated in the normal manner. The catalyst is filtered off and the filtrate is concentrated to dryness by evaporation. The residue is purified by preparative layer chromatography in a manner analogous to that described below. In order to remove the tert.-butyl ester protecting group the residue is dissolved at a low temperature in 2 ml of 95% trifluoroacetic acid. After standing for one hour at room temperature, the trifluoroacetic acid is evaporated off at room temperature and the residue is freeze-dried twice from tert.-butanol:water = 10:1. After continuous diafiltration (Amicon filter YM 10) of the 1% solution against a 1:1 mixture of 0.1 molar phosphate buffer pH = 7 and 0.1 molar sodium chloride solution and subsequent lyophilisation, N-acetylnormuramyl-L-O-{N-[2-tetradecyloxyhydroxyphosphoryloxy)ethyl]-succinamoyl}-seryl-D-isoglutamine, which is partly in sodium salt form, is obtained with $R_f = 0.05$ (chloroform:methanol:water = 70:30:5) and $R_f = 0.11$ (ethyl acetate:n-butanol:pyridine:acetic acid:water = 42:21:21:6:10).

The starting material is obtained as follows:

0.370 g (0.5 mmol) of N-acetyl-1α-O-benzylnormuramyl-L-O-(succinoyl)-seryl-D-isoglutamine-γ-tert.-butyl ester and 0.115 g (1 mmol) of N-hydroxysuccinimide, both dried over phosphorus pentoxide in a high vacuum, are dissolved in a mixture of 2 ml of absolute dimethylacetamide (dried over a molecular sieve, Merck, 3 Å) and 1.5 ml of absolute chloroform. The solution is cooled to 0°, 0.124 g (0.6 mmol) of dicyclohexyl carbodiimide is added and the whole is stirred for 4 hours at room temperature. The dicyclohexylurea which separates out can be removed by centrifugation. 0.111 g (0.3 mmol) of 2-(tetradecyloxyhydroxyphosphoryloxy)-ethylamine, dissolved in a mixture of 6 ml of chloroform, 1.5 ml of isopropanol and 0.3 ml of water, are then added and, while stirring well, 0.084 ml (0.396 mmol) of triethylamine in 0.5 ml of chloroform is added dropwise at room temperature in the course of 2 hours during which period partially undissolved amine component slowly dissolves. After a further two hours, the clear solution is concentrated by evaporation in a high vacuum at 30°.

The oily residue is taken up in a little chloroform:methanol = 2:1 and separated by thick layer chromatography on silica gel (five 20×20 cm PSC prepared plates, silica gel 60, F 254, thickness 2 mm, Merck) in the system chloroform:methanol:water = 70:30:5 (15 cm). The layer containing the phospholipid derivative (detection on the edge of the plate with the aid of Phosspray[R] 3-3047, Supelco, CH-1299 Crans) is extracted three times with dimethylacetamide:chloroform = 1:1. The solution is concentrated by evaporation in vacuo at 30° and the residue is lyophilised from tert.-butanol:water = 9:1. N-acetyl-1α-O-benzylnormuramyl-L-O-{N-[2-(tetradecyloxyhydroxyphosphoryloxy)-ethyl]-succinamoyl}-seryl-D-isoglutamine-γ-tert.-butyl ester is obtained in the form of a colourless powder with $R_f = 0.26$ (chloroform:methanol:water = 70:30:5) and $R_f = 0.45$ (ethyl acetate:n-butanol:pyridine:acetic acid:water = 42:21:21:6:10).

The starting material is obtained in the following manner:

6.25 g (9.2 mmol) of N-acetyl-1α-O-benzyl-4,6-O-isopropylidenenormuramyl-L-seryl-D-isoglutamine-γ-tert.-butyl ester are dissolved in 40 ml of absolute pyridine, 3.00 g (30 mmol) of succinic acid anhydride are added at a low temperature and the whole is left to stand at room temperature for 48 hours. It is then cooled to 0° and 20 ml of methanol are added to decompose the excess anhydride. After standing for 2 hours in an ice bath, methanol and pyridine are removed in vacuo at 30°.

The oily residue, dissolved in 40 ml of acetonitrile:water = 1:3, is introduced onto a $UPC_{12}$ column (200 g; $UPC_{12}$ is silica gel treated with dodecyltrichlorosilane, 40–63 μm, trade mark of the firm Opti) having the same solvent mixture. Using acetonitrile:water = 1:1 (20 ml fractions), first the acidic impurities are eluted and then the product. The material contained in fractions 8–25 is collected. The crystalline material remaining after the evaporation of the solvents has a lower $R_f$ value than was originally established and proves to be the des-isopropylidene compound, N-acetyl-1α-O-benzylnormuramyl-L-O-(succinoyl)-seryl-D-isoglutamine-γ-tert.-butyl ester with $[\alpha]_D^{20} = +72 \pm 1°$ (c=0.811; methanol), $R_f=0.60$ (chloroform:methanol:water=70:30:5) and $R_f=0.61$ (acetonitrile:water=3:1).

The end product of the above-mentioned reaction sequence, N-acetylnormuramyl-L-O-{N-[2-tetradecyloxyhydroxyphosphoryloxy)-ethyl]-succinamoyl}-seryl-D-isoglutamine, which is partly in sodium salt form, can also be obtained starting from the N-acetyl-1α-O-benzylnormuramyl-L-O-(succinoyl)-seryl-D-isoglutamine-γ-tert.-butyl ester described above by, as described below, first removing the benzyl protecting group, reacting the resulting product in a manner analogous to that described above with N-hydroxysuccinimide/dicyclohexyl carbodiimide/2-(tetradecyloxyhydroxyphosphoryloxy)-ethylamine and removing acidically the tert.-butyl protecting group from the resulting product in a manner analogous to that described above:

2.00 g of N-acetyl-1α-O-benzylnormuramyl-L-O-(succinoyl)-seryl-D-isoglutamine-γ-tert.-butyl ester, dissolved in 100 ml of dimethoxyethane:water=20:1, are treated for 20 hours with hydrogen after the addition of 1 g of a palladium-on-carbon catalyst (10% strength). The catalyst is filtered off, the filtrate is concentrated to dryness by evaporation and the residue is freeze-dried after being dissolved in water. N-acetylnormuramyl-L-O-(succinoyl)-seryl-D-isoglutamine-γ-tert.-butyl ester is obtained in the form of an amorphous powder with $[\alpha]_D^{20} = +20° \pm 1°$ (c=0.199 water), and $R_f=0.15$ (chloroform:methanol:water=70:30:5) and $R_f=0.45$ (ethyl acetate:n-butanol:pyridine:acetic acid:water=42:21:21:6:10).

EXAMPLE 22

0.110 g (0.12 mmol) of succinic acid 2-(1'-palmitoyl-2'-oleoyl-sn-glycero-3'-hydroxyphosphoryloxy)ethylamide and 0.028 g (0.24 mmol) of N-hydroxysuccinimide are dissolved in a mixture of 1.2 ml of absolute dimethylacetamide (dried over a molecular sieve, Merck, 3 Å) and 0.4 ml of absolute chloroform. 0.030 g (0.144 mmol) of dicyclohexyl carbodiimide is added and the whole is stirred for 3 hours at room temperature. 0.054 g (0.08 mmol) of N-acetylmuramyl-L-O-(L-phenylalanyl)-seryl-D-isoglutamine is then added and in the course of two hours 0.028 ml (0.16 mmol) of triethylamine, dissolved in 0.4 ml of chloroform, is added dropwise. After a further two hours, the suspension is concentrated by evaporation in vacuo at 30°, taken up in a little chloroform-methanol mixture and separated by thick layer chromatography on silica gel (three 20×20 cm PSC prepared plates, silica gel 60, F 254, thickness 2 mm, Merck) in the system chloroform:methanol:water=70:30:5 (15 cm run). From the desired layer, after eluting three times with dimethylacetamide:chloroform=1:1 and dialysis of the residue against, in succession, 0.1 molar sodium phosphate buffer pH 7 and water, there is obtained N-acetylmuramyl-L-O-{[N-(1'-palmitoyl-2'-oleoyl-sn-glycero-3'-hydroxyphosphoryloxy)-ethyl]-succinamoyl-L-phenylalanyl}-seryl-D-isoglutamine, which is partly in sodium salt form, as a colourless powder with $R_f=0.27$ (chloroform:methanol:water=70:30:5).

The starting materials are obtained as follows:

2-(1'-palmitoyl-2'-oleoyl-sn-glycerol-3'-hydroxyphosphoryloxy)-ethylamine is converted, in a manner analogous to that described for cephalin in Example 15, by succinic acid anhydride in pyridine into succinic acid 2-(1'-palmitoyl-2'-oleoyl-sn-glycero-3'-hydroxyphosphoryloxy)-ethylamide with $R_f=0.35$ (chloroform:methanol:water=70:30:3).

The muramyl peptide derivative required can be obtained in the following manner:

0.40 g (0.36 mmol) of N-acetyl-1α-O-benzyl-4,6-O-isopropylidenemuramyl-L-O-{[2-(p-biphenylyl)-isopropoxycarbonyl]-L-phenylalanyl}-seryl-D-isoglutamine-γ-benzyl ester is dissolved in 6.4 ml of glacial acetic acid, 1.6 ml of water are added and the mixture is left to stand for 24 hours at room temperature. The clear solution is diluted with 8 ml of glacial acetic acid and lyophilised; the strongly hygroscopic residue is taken up in tert.-butanol and again lyophilised. In order to remove 2-(p-biphenylyl)-isopropanol, the residue is triturated several times with petroleum ether and the latter is decanted off. Finally, the residue [$R_f=0.55$ (chloroform:methanol:water=70:30:5)] is dissolved in 20 ml of glacial acetic acid and, after the addition of 0.2 g of a palladium-on-carbon catalyst, is treated with hydrogen for 28 hours. The catalyst is filtered off and the acetic acid is removed by freeze-drying twice. N-acetylmuramyl-L-O-(L-phenylalanyl)-seryl-D-isoglutamine is obtained in the form of a colourless strongly hygrosopic powder with $R_f=0.11$ (chloroform:methanol:water=70:30:5), $R_f=0.26$ (acetonitrile:water=3:1) and $R_f=0.24$ (ethyl acetate:n-butanol:pyridine:acetic acid:water=42:21:21:6:10).

The starting material used is obtained as follows: 1.895 g (2.6 mmol) of N-acetyl-1α-O-benzyl-4,6-O-isopropylidenemuramyl-L-seryl-D-isoglutamine-γ-benzyl ester, 1.05 g (2.6 mmol) of 2-(p-biphenylyl)-isopropoxycarbonyl-L-phenylalanine, 0.703 g (5.2 mmol) of N-hydroxybenztriazole monohydrate and 0.635 g (5.2 mmol) of 4-dimethylaminopyridine are dissolved in a mixture of 4.5 ml of absolute dimethylformamide and 1.5 ml of acetonitrile. The solution is cooled in an ice bath and 0.70 g (3.4 mmol) of dicyclohexyl carbodiimide is added. Stirring is effected for 24 hours at from 0° to 5° and for a further 24 hours at room temperature. The thick suspension is diluted with 50 ml of ethyl acetate, the undissolved portion is filtered off with suction and the filtrate is concentrated to dryness by evaporation. The residue is taken up in 200 ml of ethyl acetate, extracted several times with 10 ml of water each time, the organic phase is dried and the solvent is evaporated. Finally, the oily residue remaining (3.63 g) is purified over 200 g of silica gel (Merck AG, 0.06–0.2 mm diameter) in the system chloroform:methanol=98:2 (6 ml fractions).

The material contained in fractions 65-215 is collected. 2.3 g (80% of the theoretical yield) of N-acetyl-1α-O-benzyl-4,6-O-isopropylidenemuramyl-L-O-{[2-(p-biphenylyl)-isopropoxycarbonyl]-L-phenylalanyl}-seryl-D-isoglutamine-γ-benzyl ester are obtained in the form of a colourless foam with $[\alpha]_D^{20} = +62 \pm 1°$ (c=0.892; chloroform), $R_f=0.45$ (chloroform:isopropanol:acetic acid=70:8:2) and $R_f=0.85$ (acetonitrile:water=3:1).

The starting material is manufactured as follows:

8.01 g (16.1 mmol) of the sodium salt of N-acetyl-1α-O-benzyl-4,6-O-isopropylidenemuramic acid, 5.80 g (16.1 mmol) of L-seryl-D-isoglutamine-γ-benzyl ester hydrochloride and 2.78 g (24.2 mmol) of N-hydroxysuccinimide are dissolved in 60 ml of absolute dimethylformamide and, at a low temperature, 3.99 g (19.3 mmol) of dicyclohexyl carbodiimide are added. After stirring for 16 hours at room temperature, 100 ml of ethyl acetate are added to the suspension, stirring is effected for 30 minutes in an ice bath and the insoluble portion (dicyclohexylurea, sodium chloride) is filtered off. The filtrate is diluted with 400 ml of ethyl acetate, the solution is extracted 10 times with 100 ml of water each time, dried over sodium sulphate and concentrated by evaporation. The slightly yellowish residue is digested with a mixture of 150 ml of ethyl acetate, 30 ml of methanol and 20 ml of ether, in the course of which crystallisation occurs. Separation is completed by the addition, in portions, of a total of 300 ml of ether and by cooling. After filtering off and drying, there remain 8.4 g (71.5% of the theoretical yield) of N-acetyl-1α-O-benzyl-4,6-O-isopropylidenemuramyl-L-seryl-D-isoglutamine-γ-benzyl ester with m.p. 178°-179°, $[\alpha]_D^{20} = +96 \pm 1°$ (c=0.695; methanol), $R_f=0.77$ (chloroform:methanol:water=70:30:5) and $R_f=0.14$ (chloroform:isopropanol:acetic acid=70:8:2).

EXAMPLE 23

In a manner analogous to that described in Example 4, starting from the N-hydroxysuccinimide ester of succinic acid 2-(1',2'-dipalmitoyl-2'-oleoyl-sn-glycero-3'-hydroxyphosphoryloxy)-ethylamide and N-acetylmuramyl-L-O-(L-phenylalanyl)-seryl-D-isoglutamine-γ-diphenylmethyl ester hydrochloride, there is obtained, after cleaving the diphenylmethyl ester, N-acetylmuramyl-L-O-{N-[2-(1',2'-dipalmitoyl-sn-glycero-3'-hydroxyphosphoryloxy)-ethyl]-succinamoyl-L-phenylalanyl}-seryl-D-isoglutamine in the form of or in admixture with its sodium salt.

EXAMPLE 24

0.269 g (1.3 mmol) of dicyclohexyl carbodiimide is added to a solution of 0.387 g (1.2 mmol) of phosphoric acid hexadecyl ester in 20 ml of absolute pyridine and the whole is stirred for 1 hour at room temperature under argon.

0.583 g (0.8 mmol) of N-acetyl-1α-O-benzyl-4,6-O-isopropylidenemuramyl-L-seryl-D-isoglutamine-γ-benzyl ester, dissolved in 20 ml of absolute pyridine, and 0.098 g (0.8 mmol) of 4-dimethylaminopyridine are then added and the mixture is stirred for a further 65 hours at room temperature under argon.

The resulting suspension is then concentrated by evaporation at 40° in a high vacuum. The residue is taken up in 100 ml of chloroform, the insoluble portion is filtered off and the chloroform phase is extracted by shaking with a total of 50 ml of 10% sodium chloride solution. The chloroform phase is dried over sodium sulphate, filtered and concentrated again by evaporation. The resulting crude product is purified by thick layer chromatography over silica gel (PF 254, Merck) in the system chloroform:methanol:water=70:30:5. The desired fraction is detached from the carrier by chloroform:methanol=1:1 and the resulting solution is concentrated by evaporation at 30° in a high vacuum. The solid white residue is taken up in 50 ml of chloroform, the insoluble portion is filtered off and concentration is carried out again by evaporation. The monosodium salt of N-acetyl-1α-O-benzyl-4,6-O-isopropylidenemuramyl-L-O-(hexadecyloxyhydroxyphosphoryl)-seryl-D-isoglutamine-γ-benzyl ester is obtained in the form of a colourless amorphous powder with $R_f=0.49$ (chloroform:methanol:water=70:30:5).

The protecting groups are removed from the resulting product as follows:

0.4 g (0.38 mmol) of the monosodium salt of N-acetyl-1α-O-benzyl-4,6-O-isopropylidenemuramyl-L-O-(hexadecyloxyhydroxyphosphoryl)-seryl-D-isoglutamine-γ-benzyl ester is hydrogenated in 8 ml of chloroform:1,2-dimethoxyethane:water=1:10:1 in the presence of a total of 0.4 g of 10% palladium-on-carbon for 90 hours at room temperature and under normal pressure. The catalyst is then filtered off and the filtrate is concentrated to dryness by evaporation at 40° in a high vacuum.

In order to remove the isopropylidene group completely, the resulting solid white residue is left to stand for a further 12 hours in 10 ml of 50% acetic acid and then concentrated again by evaporation in a high vacuum. The residue is dissolved in 50 ml of twice distilled water and this solution is filtered through a PTFE millipore filter (0.2μ) and lyophilised.

0.25 g of the monosodium salt of N-acetylmuramyl-L-O-(hexadecyloxyhydroxyphosphoryl)-seryl-D-isoglutamine is obtained in the form of an amorphous colourless powder with $R_f=0.45$ (chloroform:methanol:water=5:5:1).

In an analogous manner there is obtained the monosodium salt of N-acetylmuramyl-L-O-(1,2-dipalmitoyl-3-sn-glycerohydroxyphosphoryl)-seryl-D-isoglutamine.

We claim:

1. Hexopyranose compounds of the formula I,

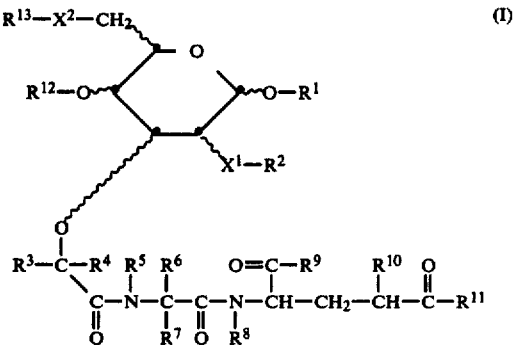

in which the hexopyranose is D-glucose, D-galactose or D-mannose, each of $X^1$ and $X^2$, independently of the other, represents a group of the formula —O— or —N($R^{14}$)—, $R^{14}$ representing hydrogen or lower alkyl, each of $R^1$, $R^2$, $R^{12}$ and $R^{13}$, independently of one another, represents a radical of the formula Ia

in which n represents 0 or 1, $Z^1$ represents carbonyl or thiocarbonyl, $Y^1$ represents unsubstituted or substituted alkylene which may be interrupted by iminocarbonyl or oxycarbonyl, $X^3$ represents a group of the formula —O— or —N($R^{14}$)—, wherein $R^{14}$ has the meaning given above, and $A^1$ represents a radical of the formula Ib,

in which $R^{15}$ represents an aliphatic or cycloaliphatic radical having at least 7 carbon atoms, or $A^1$ represents a group of the formula Ic,

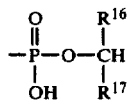 (Ic)

in which $R^{16}$ represents hydrogen and $R^{17}$ represents 2-hydroxyethyl or 1,2-dihydroxyethyl, wherein at least one hydroxy group is esterified or etherified by a radical having at least 7 carbon atoms, or wherein each of $R^{16}$ and $R^{17}$, independently of the other, represents esterified or etherified hydroxymethyl, the esterifying or etherifying radicals having at least 7 carbon atoms, or each of
$R^1$, $R^2$, $R^{12}$ and $R^{13}$, independently of one another, represents hydrogen, acyl other than a radical of the formula Ia in which n represents 1, or a radical that can be removed under physiological conditions, each of
$R^3$, $R^4$, $R^5$, $R^7$ and $R^8$, independently of one another, represents hydrogen or lower alkyl, $R^6$ represents hydrogen or lower alkyl that is unsubstituted or substituted by a group of the formula Id,

 (Id)

in which m represents 0 or 1, E represents a group of the formula —O—, —S— or —N($R^{14}$)—, $R^{14}$ having the meaning given above, $Z^2$ represents carbonyl or thiocarbonyl, $Y^2$ represents unsubstituted or substituted alkylene which may be interrupted by iminocarbonyl or oxycarbonyl, $X^4$ represents a group of the formula —O— or —N($R^{14}$)—, $R^{14}$ having the meaning given above, and $A^2$ represents a radical of the formula Ib or Ic; or by free or etherified hydroxy or mercapto, by esterified hydroxy or mercapto other than a group of the formula Id, by free amino or substituted amino other than a group of the formula Id, by free, esterified or amidated carboxy, by cycloalkyl, by carbocyclic aryl or by nitrogen-containing heteroaryl having 5 or 6 ring members in the heterocyclic ring, or $R^5$ and $R^6$ together represent unsubstituted or substituted 1,3- or 1,4-lower alkylene, each of
$R^9$ and $R^{11}$, independently of the other, represents a radical of the formula Ie,

 (Ie)

in which $X^5$ represents a group of the formula —O—, —S— or —N($R^{14}$)—, and $X^6$ represents a group of the formula —O— or —N($R^{14}$)—, in each case $R^{14}$ having the meaning given above, $Y^3$ represents unsubstituted or substituted alkylene which may be interrupted by iminocarbonyl or oxycarbonyl, and $A^3$ represents a radical of the formula Ib or Ic, or free hydroxy or mercapto, etherified hydroxy or mercapto other than a radical of the formula Ie, or free amino, or substituted amino other than a radical of the formula Ie, and $R^{10}$ represents hydrogen or free, esterified or amidated carboxy, it being possible for free functional groups to be present in protected form, wherein an asymmetric carbon atom bearing the $R^3$ group has the D configuration, an asymmetric carbon atom bearing the $R^6$ group has the L configuraton and the asymmetric carbon atom bearing the N—$R^8$ group has the D configuration, with the proviso that the compounds of the formula I have at least one radical $A^1$, $A^2$ or $A^3$, and with the further proviso that in compounds of the formula I in which at least one of the radicals $R^9$ and $R^{11}$ represents a group of the formula Ie, the pyranose ring is other than D-glucopyranose ring, or $R^1$ is other than hydrogen, or $X^1$ is other than the radical of the formula —N($R^{14}$)— and $R^2$ is other than acyl, or $R^{12}$ is other than hydrogen, or the radical of the formula —$X^2$—$R^{13}$ is other than hydroxy, or $R^4$ is other than hydrogen, or $R^6$ is other than hydrogen or than lower alkyl that is unsubstituted or substituted by free of etherified hydroxy or mercapto, by esterified hydroxy or mercapto other than a group of the formula Id, or by free amino or substituted amino other than a group of the formula Id, by cycloalkyl, by carbocyclic aryl or by nitrogen-containing heteroaryl having 5 or 6 ring members in the heterocyclic ring, or $R^7$ is other than hydrogen, and pharmaceutically acceptable salts of such compounds.

2. Compounds of the formula I according to claim 1 in which $R^1$ represents a radical of the formula Ia according to claim 1, each of
$R^2$, $R^{12}$ and $R^{13}$, independently of one another, represents hydrogen, acyl other than a radical of the formula Ia in which n represents 1, or a group that can be removed under physiological conditions, $R^5$ represents hydrogen or lower alkyl, $R^6$ represents hydrogen or lower alkyl that is unsubstituted or substituted by free or etherified hydroxy or mercapto, by esterified hydroxy or mercapto other than a group of the formula Id according to claim 1, by free amino or substituted amino other than a corresponding group of the formula Id, by free, esterified or amidated carboxy, by cycloalkyl, by carbocyclic aryl or by nitrogen-containing heteroaryl having 5 or 6 ring members in the heterocyclic ring, or $R^5$ and $R^6$ together represent unsubstituted or substituted 1,3- or 1,4-lower alkylene, and in which each of $R^9$ and $R^{11}$, independently of the other, represents free hydroxy or mercapto, etherified hydroxy or mercapto other than a radical of the formula Ie according to claim 1, or free amino or substituted amino other than a radical of the formula Ie, it being possible for free functional groups to be in protected form, and salts of such compounds.

3. Compounds of the formula I according to claim 1 in which $R^2$ represents a radical of the formula Ia according to claim 1, each of
$R^1$, $R^{12}$ and $R^{13}$, independently of one another, represents hydrogen, acyl other than a radical of the formula Ia in which n represents 1, or a group that can be removed under physiological conditions, $R^5$ represents hydrogen or lower alkyl, $R^6$ represents hydrogen or lower alkyl that is unsubstituted or substituted by free or etherified hydroxy or mercapto, by esterified hydroxy or mercapto other than a corresponding group of the formula Id according to claim 1, by free amino or substituted amino other than a group of the formula Id, by free, esterified or amidated carboxy, by cycloalkyl, by carbocyclic aryl or by nitrogen-containing heteroaryl having 5 or 6 ring members in the heterocyclic ring, or $R^5$ and $R^6$ together represent unsubstituted or substituted 1,3- or 1,4-lower alkylene, and in which each of $R^9$ and $R^{11}$, independently of the other, represents free hydroxy or mercapto, etherified hydroxy or mercapto other than a radical of the formula Ie according to claim 1, or free amino or substituted amino other than a radical of the formula Ie, it being possible for free functional groups to be in protected form, and salts of such compounds.

4. Compounds of the formula I according to claim 1 in which $R^{13}$ represents a radical of the formula Ia according to claim 1, each of $R^1$, $R^2$ and $R^{12}$, independently of one another, represents hydrogen, acyl other than a radical of the formula Ia in which n represents 1, or a group that can be removed under physiological conditions, $R^5$ represents hydrogen or lower alkyl, $R^6$ represents hydrogen or lower alkyl that is unsubstituted or substituted by free or etherified hydroxy or mercapto, by esterified hydroxy or mercapto other than a group of the formula Id according to claim 1, by free amino or substituted amino other than a corresponding group of the formula Id, by free, esterified or amidated carboxy, by cycloalkyl, by carbocyclic aryl or by nitrogen-containing heteroaryl having 5 or 6 ring members in the heterocyclic ring, or $R^5$ and $R^6$ together represent unsubstituted or substituted 1,3- or 1,4-lower alkylene, and in which each of $R^9$ and $R^{11}$, independently of the other, represents free hydroxy or mercapto, etherified hydroxy or mercapto other than a radical of the formula Ie according to claim 1, or free amino or substituted amino other than a radical of the formula Ie, it being possible for free functional groups to be in protected form, and salts of such compounds.

5. Compounds of the formula I according to claim 1 in which each of $R^1$, $R^2$, $R^{12}$ and $R^{13}$, independently of one another, represents hydrogen, acyl other than a radical of the formula Ia according to claim 1 in which n represents 1, or a group that can be removed under physiological conditions, $R^6$ represents lower alkyl substituted by a radical of the formula Id or Ida

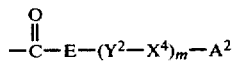

(Ida)

in which m, E, $Z^2$, $Y^2$, $X^4$ and $A^2$ have the meanings given in claim 1, and each of $R^9$ and $R^{11}$, independently of the other, represents free hydroxy or mercapto, etherified hydroxy or mercapto other than a radical of the formula Ie according to claim 1, or free amino or substituted amino other than a radical of the formula Ie, it being possible for free functional groups to be in protected form, and salts of such compounds.

6. Compounds of the formula I according to claim 1 in which each of $R^1$, $R^2$, $R^{12}$, and $R^{13}$, independently of one another, represents hydrogen, the acyl radical of an aliphatic, cycloaliphatic, aromatic or araliphatic carboxylic acid having up to 90 carbon atoms, tri-lower alkylsilyl or a radical of the formula Ia in which n and $X^3$ have the meanings given in claim 1, $Z^1$ represents carbonyl, $Y^1$ represents lower alkylene which may be interrupted by iminocarbonyl or oxycarbonyl, and $A^1$ represents a radical of the formula Ib or Ic, in which $R^{15}$ represents an aliphatic radical having at least 7 carbon atoms, $R^{16}$ represents hydrogen and $R^{17}$ represents 2-hydroxyethyl or 1,2-dihydroxyethyl, in which at least one hydroxy group is etherified by an aliphatic radical having at least 7 and up to 90 carbon atoms or is esterified by a corresponding aliphatic acyl radical, or each of $R^{16}$ and $R^{17}$, independently of the other, represents hydroxymethyl etherified by an aliphatic radical having at least 7 and up to 90 carbon atoms or esterified by a corresponding aliphatic acyl radical, $R^6$ represents hydrogen or lower alkyl that is unsubstituted or substituted by a radical of the formula Id in which m, E and $X^4$ have the meanings given above, $Z^2$ represents carbonyl, $Y^2$ represents lower alkylene which may be interrupted by iminocarbonyl or oxycarbonyl, and $A^2$ represents a radical of the formula Ib or Ic in which $R^{15}$ represents an aliphatic radical having at least 7 carbon atoms, $R^{16}$ represents hydrogen and $R^{17}$ represents 2-hydroxyethyl or 1,2-dihydroxyethyl, in which at least one hydroxy grouup is esterified by an aliphatic radical having at least 7 and up to 90 carbon atoms or by a corresponding aliphatic acyl radical, or each of $R^{16}$ and $R^{17}$, independently of the other, represents hydroxymethyl esterified by an aliphatic acyl radical having at least 7 and up to 90 carbon atoms, or $R^6$ represents lower alkyl substituted by hydroxy or mercapto, by hydroxy or mercapto etherified by an aliphatic radical containing up to 90 carbon atoms, by hydroxy or mercapto that is esterified by an aliphatic acyl radical containing up to 90 carbon atoms and is other than the group of the formula Id, by amino, by amino that is substituted by an acyl radical containing up to 90 carbon atoms and is other than a radical of the formula Id, by free carboxy, by lower alkoxycarbonyl, by carbamoyl, by lower alkylaminocarbonyl, by carboxylower alkylaminocarbonyl or by amidated carboxyl of the formula Ida according to claim 5, by phenyl that is unsubstituted or substituted by hydroxy, lower alkoxy or halogen, or by imidazolyl or indolyl, or $R^5$ and $R^6$ together represent 1,3- or 1,4-lower alkylene, each of $R^9$ and $R^{11}$, independently of the other, represents hydroxy, lower alkoxy, amino, lower alkylamino, carboxy-lower alkylamino, or a radical of the formula Ie, in which $X^5$ and $X^6$ have the meanings given above, $Y^3$ represents lower alkylene which may be interrupted by iminocarbonyl or oxycarbonyl, and $A^3$ represents a radical of the formula Ib or Ic, in which $R^{15}$ represents an aliphatic radical having at least 7 carbon atoms, $R^{16}$ represents hydrogen and $R^{17}$ represents 2-hydroxyethyl or 1,2-dihydroxyethyl, in which at least one hydroxy group is etherified by an aliphatic radical having at least 7 and up to 90 carbon atoms or is esterified by a corresponding aliphatic acyl radical, or each of $R^{16}$ and $R^{17}$, independently of the other, represents hydroxymethyl etherified by an aliphatic radical having at least 7 and up to 90 carbon atoms or esterified by a corresponding aliphatic acyl radical, and $R^{10}$ represents hydrogen, carboxy, lower alkoxycarbonyl, carbamoyl, lower alkylaminocarbonyl or carboxy-lower alkylaminocarbonyl, it being possible for free functional groups to be in protected form, with the proviso that the compounds of the formula I have at least one radical $A^1$, $A^2$ or $A^3$, and with the further proviso that in compounds of the formula I in which at least one of the radicals $R^9$ and $R^{11}$ represents a group of the formula Ie, the pyranose ring is other than a D-glucopyranose ring, or $R^1$ is other than hydrogen, or $X^1$ is other than the radical of the formula —$N(R^{14})$— and $R^2$ is other than the acyl radical of an aliphatic, cycloaliphatic, aromatic or araliphatic carboxylic acid having up to 90 carbon atoms, or $R^{12}$ is other than hydrogen, or the radical of the formula —$X^2$—$R^{13}$ is other than hydroxy, or $R^4$ is other than hydrogen, or $R^6$ is other than hydrogen or than lower alkyl that is unsubstituted or substituted by free hydroxy or mercapto, by hydroxy or mercapto etherified by an aliphatic radical containing up to 90 carbon atoms, by esterified hydroxy or mercapto other than a group of the formula Id, by free amino or amino that is substituted by an acyl radical containing up to 90 carbon atoms and is other than a group of the formula Id, by free carboxy, by lower alkylaminocarbonyl, by phenyl that is unsubstituted or substituted by hydroxy, lower alkoxy or halogen, or by imidazolyl or indolyl, or $R^7$ is other than hydrogen, and salts of such compounds.

7. Compounds of the formula I according to claim 6, in which each of $R^1$, $R^2$, $R^{12}$ and $R^{13}$, independently of one another, represents hydrogen, the acyl radical of an alkanecarboxylic acid containing up to 90 carbon atoms that is unsubstituted or substituted by hydroxy, amino and/or alkanoylamino, tri-lower alkylsilyl or a radical of the formula Ia according to claim 6.

8. Compounds of the formula I according to claim 6, in which the sugar moiety is derived from D-glucose, and $X^1$ represents the group NH, and
$X^2$ represents oxygen,
$R^1$ represents hydrogen, lower alkanoyl or a group of the formula Ia in which n represents 1, $Z^1$ represents carbonyl, $Y^1$ represents lower alkylene which may be interrupted by iminocarbonyl, $X^3$ represents a group of the formula —O— or —NH—, and $A^1$ represents a radical of the formula Ib or Ic, in which $R^{15}$ represents an alkyl radical having from 7 to 30 carbon atoms that is unsubstituted or substituted by hydroxy, amino and/or alkanoylamino having up to 30 carbon atoms, $R^{16}$ represents hydrogen and $R^{17}$ represents 2-hydroxyethyl or 1,2-dihydroxyethyl, the hydroxy groups in a radical $R^{17}$ being etherified by an alkyl radical having from 7 to 30 carbon atoms that is unsubstituted or substituted by hydroxy, amino and/or alkanoylamino having up to 30 carbon atoms or being esterified by an alkanoyl radical having from 7 to 90 carbon atoms that is unsubstituted or substituted by hydroxy, amino and/or alkanoylamino having up to 30 carbon atoms, or each of $R^{16}$ and $R^{17}$, independently of the other, represents hydroxymethyl in which the hydroxy group is etherified by an alkyl radical having from 7 to 30 carbon atoms that is unsubstituted or substituted by hydroxy, amino and/or alkanoylamino having up to 30 carbon atoms or is esterified by an alkanoyl radical having from 7 to 90 carbon atoms that is unsubstituted or substituted by hydroxy, amino and/or alkanoylamino having up to 30 carbon atoms, $R^2$ represents lower alkanoyl, hydroxy-lower alkanoyl, benzoyl or a group of the formula Ia, in which n, $Z^1$, $Y^1$, $X^3$ and $A^1$ have the meanings given earlier in this claim, $R^{12}$ represents hydrogen or lower alkanoyl, $R^{13}$ represents hydrogen, alkanoyl or hydroxyalkanoyl having up to 90 carbon atoms, alkanoylaminoalkanoyl having up to 30 carbon atoms or a group of the formula Ia in which n, $Z^1$, $Y^1$, $X^3$ and $A^1$ have the meanings given earlier in this claim, $R^3$ and $R^7$ represent hydrogen or methyl, $R^4$, $R^5$, $R^8$ and $R^{10}$ represent hydrogen, $R^6$ represents hydrogen or lower alkyl that is unsubstituted or substituted by free hydroxy or mercapto, lower alkoxy, lower alkylthio, alkanoyloxy or hydroxyalkanoyloxy having up to 90 carbon atoms, phenyl, imidazolyl, indolyl or by a group of the formula Id, in which m represents 1, E represents a group of the formula —O— or —S—, $Z^2$ represents carbonyl, $Y^2$ represents lower alkylene which may be interrupted by iminocarbonyl, $X^4$ represents a group of the formula —O—, and $A^2$ represents a radical of the formula Ib or Ic, in which $R^{15}$ represents an alkyl radical having from 7 to 30 carbon atoms that is unsubstituted or substituted by hydroxy, amino and/or alkanoylamino having up to 30 carbon atoms, $R^{16}$ represents hydrogen and $R^{17}$ represents 2-hydroxyethyl or 1,2-dihydroxyethyl, the hydroxy groups in a radical $R^{17}$ being etherified by an alkyl radical having from 7 to 30 carbon atoms that is unsubstituted or substituted by hydroxy, amino and/or alkanoylamino having up to 30 carbon atoms or being esterified by an alkanoyl radical having from 7 to 90 carbon atoms that is unsubstituted or substituted by hydroxy, amino and/or alkanoylamino having up to 30 carbon atoms, or each of $R^{16}$ and $R^{17}$, independently of the other, represents hydroxymethyl in which the hydroxy group is etherified by an alkyl radical having from 7 to 30 carbon atoms that is unsubstituted or substituted by hydroxy, amino and/or alkanoylamino having up to 30 carbon atoms, or is esterified by an alkanoyl radical having from 7 to 90 carbon atoms that is unsubstituted or substituted by hydroxy, amino and/or alkanoylamino having up to 30 carbon atoms, and each of the radicals $R^9$ and $R^{11}$, independently of the other, represents hydroxy, lower alkoxy, amino, lower alkylamino, carboxy-lower alkylamino or a radical of the formula Ie in which $X^5$ represents a group of the formula —O— or —NH—, $Y^3$ represents lower alkylene which may be interrupted by iminocarbonyl, $X^6$ represents a group of the formula —O—, and $A^3$ represents a radical of the formula Ib or Ic, in which $R^{15}$ represents an alkyl radical having from 7 to 30 carbon atoms that is unsubstituted or substituted by hydroxy, amino and/or alkanoylamino having up to 30 carbon atoms, $R^{16}$ represents hydrogen and $R^{17}$ represents 2-hydroxyethyl or 1,2-dihydroxyethyl, the hydroxy groups in a radical $R^{17}$ being etherified by an alkyl radical having from 7 to 30 carbon atoms that is unsubstituted or substituted by hydroxy, amino and/or alkanoylamino having up to 30 carbon atoms, or being esterified by an alkanoyl radical having from 7 to 90 carbon atoms that is unsubstituted or substituted by hydroxy, amino and/or alkanoylamino having up to 30 carbon atoms, or each of $R^{16}$ and $R^{17}$, independently of the other, represents hydroxymethyl in which the hydroxy group is etherified by an alkyl radical having from 7 to 30 carbon atoms that is unsubstituted or substituted by hydroxy, amino and/or alkanoylamino having up to 30 carbon atoms, or is esterified by an alkanoyl radical having from 7 to 90 carbon atoms that is unsubstituted or substituted by hydroxy, amino and/or alkanoylamino having up to 30 carbon atoms, with the proviso that the compounds have at least one radical selected from the group $A^1$, $A^2$ or $A^3$, and with the further proviso that in compounds of the formula I in which at least one of the radicals $R^9$ and $R^{11}$ represents a group of the formula Ie, $R^1$ is other than hydrogen, or $R^2$ is other than lower alkanoyl, hydroxy-lower alkanoyl or benzoyl, or $R^{12}$ is other than hydrogen, or $R^{13}$ is other than hydrogen, or $R^6$ is other than hydrogen or lower alkyl that is unsubstituted or substituted by free hydroxy or mercapto, by lower alkoxy, lower alkylthio, alkanoyloxy or hydroxyalkanoyloxy having up to 90 carbon atoms, phenyl, imidazolyl or by indolyl, or $R^7$ is other than hydrogen, and salts of these compounds.

9. Compounds of the formula I according to claim 6, in which $X^1$ represents a group of the formula —N($R^{14}$)—, $R^{14}$ denoting hydrogen or $C_{1-4}$-alkyl, $X^2$ represents oxygen, $R^1$ represents hydrogen, lower alkanoyl or a group of the formula Ia in which n represents 0 or 1, $Z^1$ represents carbonyl, $Y^1$ represents lower alkylene which may be interrupted by iminocarbonyl, $X^3$ represents oxygen, and $A^1$ represents a radical of the formula Ib or Ic in which $R^{15}$ represents an alkyl or alkenyl radical having from 7 to 30 carbon atoms that is unsubstituted or substituted by hydroxy, amino and/or alkanoylamino having up to 22 carbon atoms, $R^{16}$ represents hydrogen and $R^{17}$ represents 2-hydroxyethyl or 1,2-dihydroxyethyl, at least one hydroxy group in a radical $R^{17}$ being etherified by an alkyl or alkenyl radical having from 7 to 30 carbon atoms or being esterified by an alkanoyl or alkenoyl radical having from 7 to 30 carbon atoms, or each of $R^{16}$ and $R^{17}$, independently of the other, represents hydroxymethyl, the hydroxy group being etherified by an alkyl or alkenyl radical having from 7 to 30 carbon atoms or being esterified by an alkanoyl or alkenoyl radical having from 7 to 30 carbon atoms, $R^2$ represents lower alkanoyl, hydroxy-lower alkanoyl, benzoyl or, independently of $R^1$, $R^{12}$ and $R^{13}$, represents a group of the formula Ia as defined earlier in this claim, each of $R^3$, $R^4$, $R^5$, $R^7$ and $R^8$, independently of one another, represents hydrogen, methyl or ethyl, $R^6$ represents hydrogen or lower alkyl that is unsubstituted or substituted by free hydroxy, free mercapto, lower alkoxy, lower alkylthio, alkanoyloxy having from 2 to 30 carbon atoms, alkenoyloxy having from 6 to 30 carbon atoms, phenyl, 4-hydroxyphenyl or by a group of the formula Id in which m represents 0 or 1, E represents oxygen or sulphur, $Z^2$ represents carbonyl, $Y^2$ represents lower alkylene that is unsubstituted or substituted by phenyl and may be interrupted by iminocarbonyl, $X^4$ represents oxygen, and $A^2$, independently of $A^1$ and $A^3$, represents a radical of the formula Ib or Ic as defined earlier in this claim, each of $R^9$ and $R^{11}$, independently of the other, represents hydroxy, lower alkoxy, amino, lower alkylamino, carboxy-lower alkylamino, lower alkoxycarbonyl-lower alkylamino, carbamoyl-lower alkylamino or a radical of the formula Ie, in which $X^5$ represents oxygen or NH, $Y^3$ represents lower alkylene which may be interrupted by iminocarbonyl, $X^6$ represents oxygen and $A^3$, independently of $A^1$ and $A^2$, represents a radical of the formula Ib or Ic as defined earlier in this claim, $R^{10}$ represents hydrogen, $R^{12}$ represents hydrogen, lower alkanoyl or the same radical as $R^{13}$, and $R^{13}$ represents hydrogen, or alkanoyl or alkenoyl, each having up to 30 carbon atoms, or, independently of $R^1$ and $R^2$, represents a radical of the formula Ia as defined earlier in this claim, with the proviso that the compounds have at least one and at most two radicals selected from the group consisting of $A^1$, $A^2$ and $A^3$, and with the further proviso that in those compounds in which at least one radical selected from the group consisting of $R^9$ and $R^{11}$ represents a group of the formula Ie, $R^1$ is other than hydrogen, or $R^2$ is other than lower alkanoyl, hydroxy-lower alkanoyl or benzoyl, or $R^4$ is other than hydrogen or $R^6$ is other than hydrogen or than lower alkyl that is unsubstituted or substituted by free hydroxy, free mercapto, lower alkoxy, lower alkylthio, alkanoyloxy, alkenoyloxy, phenyl or by 4-hydroxyphenyl, or $R^7$, $R^{12}$ or $R^{13}$ is different from hydrogen, and salts of these compounds.

10. Compounds of the formula I according to claim 9, in which $X^1$ represents the group NH, $X^2$ represents oxygen, $R^1$ represents hydrogen or lower alkanoyl, $R^2$ represents lower alkanoyl, benzoyl or a group of the formula Ia, in which n represents 0 or 1, $Z^1$ represents carbonyl, $Y^1$ represents lower alkylene which may be interrupted by one or two iminocarbonyl groups, $X^3$ represents oxygen, and $A^1$ represents a radical of the formula Ib or Ic in which $R^{15}$ represents an alkyl radical having from 7 to 22 carbon atoms, $R^{16}$ represents hydrogen and $R^{17}$ represents 1,2-dihydroxyethyl, each of the two hydroxy groups, independently of the other, being esterified by an alkanoyl or alkenoyl radical having from 10 to 22 carbon atoms, $R^3$ represents hydrogen or methyl, $R^4$, $R^5$, $R^7$ and $R^8$ represent hydrogen, $R^6$ represents hydrogen or lower alkyl that is unsubstituted or substituted by free hydroxy, alkanoyloxy having from 2 to 22 carbon atoms, alkenoyloxy having from 6 to 22 carbon atoms, phenyl or by a group of the formula Id, in which m represents 0 or 1, E represents oxygen, $Z^2$ represents carbonyl, $Y^2$ represents lower alkylene that is unsubstituted or substituted by phenyl and may be interrupted by iminocarbonyl, $X^4$ represents oxygen and $A^2$, independently of $A^1$ and $A^3$, represents a radical of the formula Ib or Ic as defined above, each of $R^9$ and $R^{11}$, independently of the other, represents hydroxy, lower alkoxy, amino, lower alkylamino, α-carboxy-lower alkylamino, α-lower alkoxycarbonyl-lower alkylamino, α-carbamoyl-lower alkylamino or a radical of the formula Ie, in which $X^5$ represents the group NH, $Y^3$ represents lower alkylene which may be interrupted by one or two iminocarbonyl groups, $X^6$ represents oxygen and $A^3$, independently of $A^1$ and $A^2$, represents a radical of the formula Ib or Ic defined above, $R^{10}$ represents hydrogen, $R^{12}$ represents hydrogen, lower alkanoyl or the same radical as $R^{13}$, and $R^{13}$ represents hydrogen, alkanoyl having from 2 to 22 carbon atoms, alkenoyl having from 6 to 22 carbon atoms or, independently of $R^2$, represents a radical of the formula Ia as defined above, and salts of these compounds.

11. Compounds of the formula I according to claim 10, in which $X^1$ represents the group NH, $X^2$ represents oxygen, $R^1$ represents hydrogen or $C_{2-4}$-alkanoyl, $R^2$ represents $C_{2-4}$-alkanoyl or a group of the formula Ia in which n represents 0 or 1, $Z^1$ represents carbonyl, $Y^1$ represents lower alkylene which may be interrupted by one or two iminocarbonyl groups, $X^3$ represents oxygen and $A^1$ represents a radical of the formula Ib or Ic, wherein $R^{15}$ represents an unbranched alkyl radical having from 12 to 18 carbon atoms, $R^{16}$ represents hydrogen and $R^{17}$ represents 1,2-dipalmitoyloxyethyl or 2-oleoyloxy-1-palmitoyloxyethyl, $R^3$ represents hydrogen or methyl, $R^4$, $R^5$, $R^7$, $R^8$ and $R^{10}$ represent hydrogen, $R^6$ represents methyl, ethyl or isopropyl that is unsubstituted or substituted by a radical of the formula Id wherein m represents 0 or 1, E represents oxygen, $Z^2$ represents carbonyl, $Y^2$ represents lower alkylene that is unsubstituted or substituted by phenyl and may be interrupted by one or two iminocarbonyl groups, $X^4$ represents oxygen and $A^2$, independently of $A^1$ and $A^3$, represents a radical of the formula Ib or Ic defined above, $R^9$ represents amino, $R^{11}$ represents hydroxy or a radical of the formula Ie in which $X^5$ represents the group NH, $Y^3$ represents lower alkylene which may be interrupted by one or two iminocarbonyl groups, $X^6$ represents oxygen and $A^3$, independently of $A^1$ and $A^2$, represents a radical of the formula Ib or Ic defined above, $R^{12}$ represents hydrogen, acetyl or the same radical is $R^{13}$, and $R^{13}$ represents hydrogen, acetyl or, independently of $R^2$, a radical of the formula Ia as defined above, and salts of these compounds.

12. Compounds of the formula I according to any one of claims 1 to 11 in which the radicals $A^1$, $A^2$ and $A^3$ if present represent a radical of the formula Ic, and salts thereof.

13. Compounds of the formula I according to any one of claims 1–7 and 9–11 in which the sugar moiety is derived from (D)-glucose, and salts thereof.

14. Compounds of the formula I according to any one of claims 1 to 11 which contain a radical of the formula Ia in which n represents 1, or a radical of the formula Id in which m represents 1, and salts thereof.

15. Compounds of the formula I according to any one of claims 1 to 11 which contain a radical of the formula Ia in which n represents 0, or a radical of the formula Id in which m represents 0, and salts thereof.

16. Compounds of the formula I according to any one of claims 1, 4, and 6–11 which carry only one phosphoryl substituent, this being in the radical $R^{13}$, and salts thereof.

17. Compounds of the formula I according to any one of claims 1 and 5–11 which carry only one phosphoryl substituent, this being in the radical $R^6$, and salts thereof.

18. Compounds of the formula I according to any one of claims 1 and 6–11 which carry only one phosphoryl substituent, this being in the radical $R^{11}$, and salts thereof.

19. The compounds of the formula I according to claim 1 which are N-(2-[1',2'-dipalmitoyl-rac-glycero-3'-hydroxyphosphoryloxy]-acetyl)-muramyl-L-alanyl-D-isoglutamine or N-acetyl-1,4,6-O-triacetylmuramyl-L-alanyl-D-isoglutaminyl-L-alanyl-2-(1',2'-dipalmitoyl-sn-glycero-3'-hydroxyphosphoryloxy)-ethylamide.

20. Sodium salts of compounds of the formula I according to claim 1.

21. Pharmaceutical compositions that contain an immunomodulating effective amount of at least one compound of the formula I and/or at least one pharmaceutically acceptable salt of such a compound according to any one of claims 1 to 11 together with a pharmaceutically acceptable carrier.

22. A method of modulating the immune response in humans or other animals comprising administering to said humans or other animals an effective amount of a compound according to any one of claims 1 to 11.

23. Pharmaceutical preparations comprising an antibiotically effective amount of a combination of at least one antibiotic and an amount of a compound according to any one of claims 1–11 capable of increasing the activity of the antibiotic, together with a pharmaceutically acceptable carrier.

24. A method for increasing the activity of an antibiotic in mammals comprising administering the antibiotics to mammals together with a compound according to any one of claims 1 to 11, the compound being administered 24 hours before or after the antibiotics.

* * * * *